US012612602B2

(12) United States Patent　　　　　(10) Patent No.:　US 12,612,602 B2
Cortiella et al.　　　　　　　　　　　(45) Date of Patent:　　Apr. 28, 2026

(54) PRODUCTION OF A BIOENGINEERED LUNG

(71) Applicant: THE BOARD OF REGENTS OF THE UNIVERSITY OF TEXAS SYSTEM, Austin, TX (US)

(72) Inventors: Joaquin Cortiella, Galveston, TX (US); Joan E. Nichols, Galveston, TX (US); Jean Niles, Galveston, TX (US); Saverio Lafrancesca, Galveston, TX (US); Jason Sakamoto, Manvel, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 868 days.

(21) Appl. No.: 17/047,516

(22) PCT Filed: Apr. 18, 2019

(86) PCT No.: PCT/US2019/028162
§ 371 (c)(1),
(2) Date: Oct. 14, 2020

(87) PCT Pub. No.: WO2019/204631
PCT Pub. Date: Oct. 24, 2019

(65) Prior Publication Data
US 2021/0155904 A1　　May 27, 2021

Related U.S. Application Data

(60) Provisional application No. 62/659,321, filed on Apr. 18, 2018.

(51) Int. Cl.
*C12N 5/071*　　　(2010.01)
*A61K 35/42*　　　(2015.01)

(52) U.S. Cl.
CPC ............ *C12N 5/0697* (2013.01); *A61K 35/42* (2013.01); *C12N 5/0688* (2013.01); *C12N 2501/115* (2013.01); *C12N 2501/117* (2013.01); *C12N 2501/165* (2013.01); *C12N 2502/1107* (2013.01); *C12N 2502/1114* (2013.01); *C12N 2502/1157* (2013.01); *C12N 2533/90* (2013.01)

(58) Field of Classification Search
None
See application file for complete search history.

(56) References Cited

U.S. PATENT DOCUMENTS

2009/0227025 A1　9/2009　Nichols et al.
2011/0045045 A1　2/2011　Cortiella

FOREIGN PATENT DOCUMENTS

WO　　WO 2017070392　　*　4/2017

OTHER PUBLICATIONS

Zevan et al ( J of Materials Science, 2009,v.20 pp. 235-247).*
Bonvillain, et al., "A Nonhuman Primate Model of Lung Regeneration: Detergent-Mediated Decellularization and Initial In Vitro Recellularization with Messenchymal Stem Cells," Tissue Eng. Part A, 18, 2437-2452, 2012.
Abreu, et al., "Extracellular Vesicles Derived from Mesenchymal Stromal Cells: A Therapeutic Option in Respiratory Disease?" *Stem Cell Research & Therapy*, 7(1): 53, 2016.
Anders, et al., "HTSeq—A Python Framework to Work with High-Throughput Sequencing Data," *Bioinformatics* 31: 166-169, 2015.
Auton, et al., "Predicting the energetics of osmolyte-induced protein folding/unfolding," *Proc. Natl. Acad. Sci. U. S. A.* 102: 15065-15068, 2005.
Barnett, et al., "BamTools: a C++ API and Toolkit for Analyzing and Managing BAM Files," *Bioinformatics* 27: 1691-1692, 2011.
Bergmark, et al., "Assessment of the Specificity of Burkholderia and Pseudomonas qPCR Assays for Detection of These Genera in Soil Using 454 Pyrosequencing," *FEMS Microbiol. Lett.* 333: 77-84, 2012.
Bernasconi, et al., "Airway Microbiota Determines Innate Cell Inflammatory or Tissue Remodeling Profiles in Lung Transplantation," *American Journal of Respiratory and Critical Care Medicine*, 194(10): 1252-1263, 2016.
Birdsey, et al., "The Endothelial Transcription Factor ERG Promotes Vascular Stability and Growth Through wnt/β-Catenin Signaling," *Developmental Cell*, 32(1): 82-96, 2015.
Bolger, et al., "Trimmomatic: A Flexible Trimmer for Illumina Sequence Data," *Bioinformatics* 30: 2114-2120, 2014.
Bonvillain, et al., "A Nonhuman Primate Model of Lung Regeneration: Detergent-Mediated Decellularization and Initial In Vitro Recellularization with Messenchyrnal Stem Cells," *Tissue Eng. Part A*, 18: 2437-2452, 2012.
Brasile, et al., "NOS: The Underlying Mechanism Preserving Vascular Integrity and During Ex Vivo Warm Kidney Perfusion," *American Journal of Transplantation*, 3: 674-679, 2003.
Cho, et al., "Mesenchymal Stem Cells Reciprocally Regulate the M1/M2 Balance in Mouse Bone Marrow-Derived Macrophages," *Experimental & Molecular Medicine* 46: e70, 2014.

(Continued)

*Primary Examiner* — Michail A Belyavskyi

(57)　　　　ABSTRACT

The present invention provides processes for producing a bioengineered lung (BEL) from an acellular lung matrix that has been treated with growth hormones, seeded with primary lung cells, and cultured in a bioreactor. Also provided are BELs and methods of transplanting the BEL into a subject in need of a lung transplant, and methods for using BELs for the study of the lung microbiome and its role in lung development and remodeling.

20 Claims, 35 Drawing Sheets

(56) References Cited

OTHER PUBLICATIONS

Cortiella, et al., "Influence of Acellular Natural Lung Matrix on Murine Embryonic Stem Cell Differentiation and Tissue Formation," *Tissue Eng Part A.*, 16: 2565-2580, 2010.

Crosby, et al., "Epithelial Repair Mechanisms in the Lung," *Am. J. Physiol. Lung Cell Mol. Physiol.* 298: L715-L731, 2010.

Des Rieux, et al., "Vascular Endothelial Growth-Factor-Loaded Injectable Hydrogel Enhances Plasticity in the Injured Spinal Cord," *J. Biomed. Mater. Res. Part A* 102: 2345-2355, 2014.

Dickson, et al., The Microbiome and the Respiratory Tract, *Annual Review of Physiology.* 78: 481-504, 2016.

Dimitrievska, et al., "Historical Perspective and Future Direction of Blood Vessel Development," *Cold Spring Harb. Perspect. Med.* A025742, 2017.

Dobin, et al., "Star: Ultrafast Universal RNA-seq Aligner," *Bioinformatics* 29: 15-21, 2013.

Fernandez-Moure, et al., "Porcine Acellular Lung Matrix for Wound Healing and Abdominal Wall Reconstruction: A Pilot Study," *Tissue Engineering and Regenerative Medicine*, 7:1-8, 2016.

Fish, et al., "The Molecular Regulation of Arteriovenous Specification and Maintenance," *Developmental Dynamics*, 2(44): 391-409, 2015.

Fishman, et al., "The Clinical Significance of the Pulmonary Collateral Circulation," *Circulation*, 24: 677-690, 1961.

Friis, et al., "Mycoplasm Suipneumoniae and Mycoplasma Flocculare in Comparative Pathogenicity Studies," *Acta Vet. Scand.* 15: 507-518, 1974.

Fukuda, et al., "An Unclassified Microorganism: Novel Pathogen Candidate Lurking in Human Airways," *PLoS ONE* 9: e103646, 2014.

Fukumura, et al., "Predominant Role of Endothelial Nitric Oxide Synthase in Vascular Endothelial Growth Factor-Induced Angiogenesis and Vascular Permeability," *PNAS,*. 98: 2604-2609, 2001.

Gallacher, et al., "Respiratory Microbiome of New-Born Infants," *Frontiers in Pediatrics,.* 4: 10, 2016.

Godin, et al., "Discoidal Porous Silicon Particles: Fabrication and Biodistribution in Breast Cancer Bearing Mice," *Advanced Functional Materials*, 22(20): 4225-4235, 2012.

Guimaraes, et al., "A Quantitative TaqMan PCR Assay for the Detection of Mycoplasma suis," *Journal of Applied Microbiology*, 111: 417-425, 2011.

Guo, et al., "Mesenchymal Stem Cells for Inducing Tolerance in Organ Transplantation," *Frontiers in Cell and Developmental Biology*, 2(202): 8, 2014.

Haugland, et al., "Comparison of Enterococcus Measurements in Freshwater at Two Recreational Beaches by Quantitative Polymerase Chain Reaction and Membrane Filter Culture Analysis," *Water Research*, 39: 559-568, 2005.

Herold, et al., "Acute Lung Injury: How Macrophages Orchestrate Resolution of Inflammation and Tissue Repair," *Frontiers in Immunology*, 2: 65, 2011.

International Search Report and Written Opinion Issued in Corresponding PCT Patent Application No. PCT/US2019/028162, dated Jul. 12, 2019.

Ionescu, et al., "Stem cell conditioned medium improves acute lung injury in mice: in vivo evidence for stem cell paracrine action," *Am. J. Physiol. Lung Cell. Mol. Physiol.* 303: L967-L977 (2012).

Jiang, et al., "VEGF-Loaded Nanoparticle-Modified BAMAS Enhance Angiogenesis and Inhibit Graft Shrinkage in Tissue-Engineered Bladder," *Annals of Biomedical Engineering*, 10: 2577-2586, 2015.

Judge, et al., "Anatomy and Bronchoscopy of the Porcine Lung: A Model for Translational Respiratory Medicine," *American Journal of Respiratory Cell and Molecular Biology*, 51(3): 334-343, 2014.

Kaur et al., "Identifying a Site for Maximum Delivery of Oxygen to Transplanted Cells," *Tissue Engineering* 6(3): 229-232, 2000.

Kelly, et al., "Respiratory Mechanics and Gas Exchange in Postobstructive Pulmonary Vasculopathy," *European Respiratory Journal*, 8: 202-208, 1995.

Khatri, et al., "Porcine Lung Mesenchymal Stromal Cells Possess Differentiation and Immunoregulatory Properties," *Stem Cell Research and Therapy*, 6: 222-232, 2015.

Lee, et al., "Concise Review: Mesenchymal Stem Cells for Acute Lung Injury: Role of Paracrine Soluble Factors," *Stem Cells* 29: 913-919, 2011.

Lindskog, et al., "The Lung-Specific Proteome Defined by Integration of Transcriptomics and Antibody-Based Profiling," *FASEB J.* 28: 5184-5196, 2014.

Love, et al., "Moderate Estimation of Fold Change and Dispersion for RNA-seq Data with DEeq2," *Genome Biol.* 15: 550-571, 2014.

Macchi, et al., "The Effect of Osmolytes on Protein Fibrillation," *Int J. Mol. Sci.* 13: 3801-3819, 2012.

Martinu, et al., "Acute Rejection and Humoral Sensitization in Lung Transplant Recipients," *Proc. Am. Thorac. Soc.*, 6(1): 54-65, 2009.

Matar, et al., "Two-step PCR-based assay for identification of bacterial etiology of otitis media with effusion in infected Lebanese children," *J. Clin. Microbiol.* 36: 1185-1188 (1998).

Minutti, et al., "Tissue-specific contribution of macrophages to wound healing," *Semi. Cell Dev. Biol.* 61: 3-11 (2017).

Mohammadi, et al., "Optimization of Real-time PCR Assay for Rapid and Sensitive Detection of Eubacterial 16S Ribosomal DNA in Platelet Concentrates," *J. Clin. Microbiol.* 41: 4796-4798, 2003.

Mondrinos, et al., "In Vivo Pulmonary Tissue Engineering: Contribution of Donor-Derived Endothelial Cells to Construct Vascularization," *Tissue Eng. Part A*, 14(3): 361-368, 2008.

Morrell, et al., "Angiotensin Converting Enzyme Expression is Increased in Small Pulmonary Arteries of Rats with Hypoxia-Induced Pulmonary Hypertension," *J. Clin. Invest.* 96: 1823-1833, 1995.

Morrell, et al., "Developmental Regulation of Angiotensin Converting Enzyme and Angiotensin Type 1 Receptor in the Rat Pulmonary Circulation," *Am. J. Respir. Cell Mol. Biol.* 14: 526-537, 1996.

Morrisey & Hogan, "Preparing for the First Breath: Genetic and Cellular Mechanisms in Lung Development," *Dev Cell*, 18: 8-23, 2010.

Mortazavi, et al., "Mapping and Quantifying Mammalian Transcriptomes by RNA-Seq," *Nat. Methods* 5: 621-628, 2008.

Mouraux, et al., "Airway Microbiota Signals Anabolic and Catabolic Remodeling in the Transplanted Lung," *Journal of Allergy and Clinical Immunology*, 141(2): 718-729, 2017.

Nichols, et al., "Giving New Life to Old Lungs: Methods to Produce and Assess Whole Human Paediatric Bioengineered Lungs," *J. Tissue Eng. Regen. Med.*, 1(7): 2136-2152, 2017.

Nichols, et al., "Neurogenic and Neuro-Protective Potential of a Novel Subpopulation of Peripheral Blood-Derived CD133+ ABCG2+ CXCR4+ Mesenchymal Stem Cells: Development of Autologous Cell-Based Therapeutics for Traumatic Brain Injury," *Stem Cell Res. Ther.* 4: 3-26, 2013.

Nichols, et al., "Production and Assessment of Decellularized Pig and Human Lung Scaffolds," *Tissue Eng. Part A* 19: 2045-2062, 2013.

Nichols, et al., "Production and Transplantation of Bioengineered Lung Into a Large-Animal Model," *Science Translational Medicine*, 10: eaao3926, 2018.

Nichols, et al., "Use of FITC Labeled Influenza Virus and Flow Cytometry to Assess Binding and Internalization of Virus by Monocytes-Macrophages and Lymphocytes," *Arch. Virol.* 130: 441-455, 1992.

Niederwerder, et al., "Role of the Microbiome in Swine Respiratory Disease," *Vet. Microbiol.* 209: 97-106, 2017.

Ott, et al., "Regeneration and Orthotopic Transplantation of a Bioartificial Lung," *Nat. Med.* 16: 927-933, 2010.

Petersen, et al., "Tissue-Engineered Lungs for In Vivo Implantation," *Science*, 329: 538-541, 2010.

Quillien, et al., "Distinct Notch Signaling Outputs Pattern the Developing Arterial System," *Development* 141: 1544-1552, 2014.

R Core Team, "R: A Language and Environment for Statistical Computing," R Foundation for Statistical Computing, Vienna, Austria, (2016).

Remy, et al., "Bronchial Arteries in the Pig Before and After Permanent Pulmonary Artery Occlusion," *Invest. Radiol.* 32: 218-224, 1997.

Ren, at al., "Engineering Pulmonary Vasculature in Decellularized Rat and Human Lungs," *Nat. Biotechnol.* 33: 1097-1102, 2015.

(56)     References Cited

OTHER PUBLICATIONS

Rizvi & Saleh, "Applications of Nanoparticle Systems in Drug Delivery Technology," *Saudi Pharmaceutical Journal*, 26: 64-70, 2018.

Robinson, et al., "A Novel Platelet Lysate Hydrogel for Endothelial Cell and Mesenchymal Stem Cell-Directed Neovascularization," *Acta Biomater*. 36: 86-98, 2016.

Shah, et al., "Regulation of Endothelial Homeostasis, Vascular Development and Angiogenesis by the Transcription Factor ERG," *Vascular Pharmacology*, 86: 3-13, 2016.

Song, et al., "Enhanced In Vivo Function of Bioartificial lungs in rats," *Ann. Thorac. Surg*. 92: 998-1005 (2011).

Stabler, et al., "Enhanced Re-Endothelialization of Decellularized Rat Lungs," *Tissue Eng. Part C Methods* 22: 439-450, 2016.

Tao, et al., "Proangiogenic Features of Mesenchymal Stem Cells and Their Therapeutic Applications," *Stem Cells International.*, Article ID 1314709, 2016.

Tasciotti, et al., "Mesoporous Silicon Particles as a Multistage Delivery System for Imaging and Therapeutic Applications," *Nature Nanotechnology*, 3: 151-157, 2008.

Thakker, et al., "Mesenchymal Stem Cell Therapy for Cardiac Repair," *Curr. Treat. Options Cardiovasc. Med*. 16: 323, 2014.

Tocqueville, et al., "Multilocus Sequence Typing of Mycoplasma Hyorhinis Strains Identified by Real-Time TaqMan PCR Assay," *J. Clin Microbiol*. 52: 1664-1671, 2014.

Turni, et al., "Validation of a Real-time PCR for Haemophilus Parasuis," *J. Appl. Microbiol*. 108: 1323-1331, 2010.

Willner, et al., "Reestablisment of Recipient-Associated Microbiota in the Lung Allograft is Linked to Reduced Risk of Bronchiolitis Obliterans Syndrome," *Am. J. Clin. Resp. Care Med*. 187: 640-647, 2013.

Wolk, et al., "Pathogen Profiling: Rapid Molecular Characterization of *Staphylococcus aureus* by PCR/electrospray Ionization-Mass Spectrometry and Correlation with Phenotype," *J. Clin. Microgiol*. 47: 3129-3137, 2009.

Zozaya-Hinchliffe, et al., "Quantitative PCR Assessments of Bacterial Species in Women With and Without Bacterial Vaginosis," *J. Clin. Microbial*. 48: 1812-1819, 2010.

Zuo, et al., "P63+ KRT5+ Distal Airway Stem Cells are Essential for Lung Regeneration," *Nature* 517: 616-620, 2015.

* cited by examiner

A

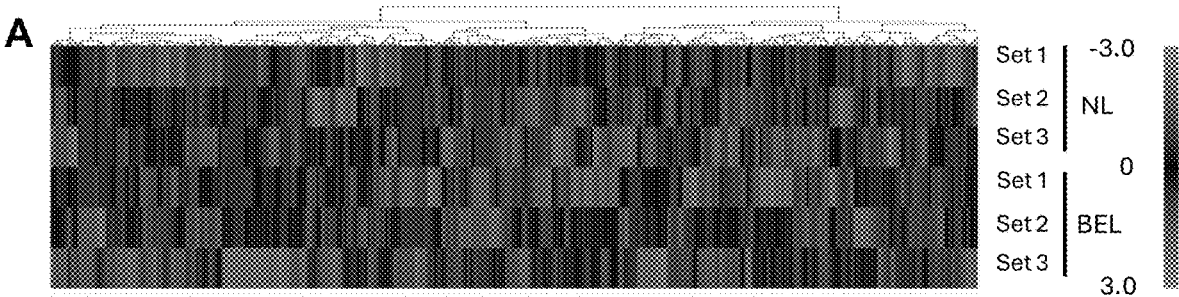

| | |
|---|---|
| Set 1 | -3.0 |
| Set 2 | NL |
| Set 3 | |
| Set 1 | 0 |
| Set 2 | BEL |
| Set 3 | 3.0 |

B     Summary of FCs for Bioengineered Lungs Compared to Native Lung

| Comparison | Number (%) | | |
|---|---|---|---|
| | 0<FC<=0.5 | 0.5<FC<2 | FC>=2 |
| Set 1: Bioengineered Lung *VS* Native | 545 (13.20%) | 2597 (62.91%) | 986 (23.89%) |
| Set 2: Bioengineered Lung *VS* Native | 523 (12.67%) | 3197 (77.45%) | 408 (9.88%) |
| Set 3: Bioengineered Lung *VS* Native | 392 (9.50%) | 3157 (76.48%) | 579 (14.03%) |
| TOTAL | 1460 (11.79%) | 8951 (72.28%) | 1973 (15.93%) |

C

| FOLD INCREASE | GENE ID | GENE NAME | DESCRIPTION |
|---|---|---|---|
| 5 | ENSSSCG00000001556 | MAPK14 | Map Kinase 14 |
| 5 | ENSSSCG00000010816 | TGFB2 | Transforming Growth Factor Beta 2 |
| 3 | ENSSSCG00000024960 | PDGFC | Platelet Derived Growth Factor C |
| 3 | ENSSSCG00000006862 | VCAM1 | Vascular cell adhesion molecule 1 |
| 3 | ENSSSCG00000012135 | VEGFD | Vascular endothelium growth factor D |
| 3 | ENSSSCG00000006159 | HEY1 | Hes Related Family BHLT Transcription Factor with YRPW Motif 1 |
| 3 | ENSSSCG0000001725 | SRY-Box-9 | Sex-determining region 9 (SOX 9) |
| 2.5 | ENSSSCG00000024651 | HEYL | Hes Related Family BHLT Transcription Factor with YRPW Motif-Like |
| 2.5 | ENSSSCG00000008841 | PDGFRA | Platelet Derived Growth Factor Receptor Alpha |
| 2.25 | ENSSSCG00000016416 | SHH | Sonic Hedgehog |
| 2 | ENSSSCG0000001795 | SRY-Box-15 | Sex determining factor 15 (SOX 15) |
| 2 | ENSSSCG0000001581 | FGFR1 | Fibroblast Growth Factor Receptor 1 |
| 2 | ENSSSCG0000000610 | SELP | Selectin P |
| 2 | ENSSSCG0000000182 | WNT10B | WNT family member 10B |
| 2 | ENSSSCG00000002906 | ETV2 | ETS Variant 2 |
| 2 | ENSSSCG00000013655 | ICAM1 | Intracellular adhesion molecule 1 |
| 1.55 | ENSSSCG000000884 | KDR/VEGFR2 | Kinase Insert Domain Receptor |
| 1.33 | ENSSSCG0000001041 | CXCL 12/SDF-1 | Stromal Derived Factor 1 |
| 1.29 | ENSSSCG00000022318 | ERG | ETS-related gene |
| 1.28 | ENSSSCG00000011102 | NRP1 | Neuropilin 1 |
| 1.25 | ENSSSCG0000000108 | SRY-Box 4 | Sex determining factor 4 (SOX 4) |
| 1.17 | ENSSSC0000001568 | CXCR4 | C-X-C Motif Chemokine receptor 4 |

FIG. 3A-3C

| Day of Installation | Cell type or Reagent installed | Number of Installations | Method of Installation | Flow rate for installation |
|---|---|---|---|---|
| 1 | VEGF-MP in FGF2-Hydrogel | 1 | pumped into PA | 0.5 ml/hr |
| 1 | PRP | 2-60 minutes apart | pumped into PA | 0.5 ml/hr |
| 1 | Primary Vascular Cells | 2-3 hrs apart | pumped into PA | 0.5 ml/hr |
| 2 | EGM+PRP | 2-60 minutes apart | pumped into PA | 0.5 ml/hr |
| 2 | Primary Vascular Cells | 2-60 minutes apart | pumped into PA | 0.5 ml/hr |
| 3 | EGM+PRP | 2-60 minutes apart | pumped into PA | 0.5 ml/hr |
| 5 | Primary Vascular Cells | 2-3 hrs apart | pumped into PA | 0.5 ml/hr |
| 6 | EGM+PRP | 2-60 minutes apart | pumped into PA | 0.5 ml/hr |
| 7 | Primary Vascular Cells | 2-3 hrs apart | pumped into PA | 0.5 ml/hr |
| 9 | EGM+PRP | 2-60 minutes apart | pumped into PA | 1 ml/hr |
| 10 | Primary Vascular Cells | 2-3 hrs apart | pumped into PA | 1 ml/hr |
| 11 | EGM+PRP | 2-60 minutes apart | pumped into PA | 1 ml/hr |
| 11 | MNL | 2-60 minutes apart | pumped into PA | 0.5 ml/hr |
| 12 | Primary Vascular Cells | 2-60 minutes apart | pumped into PA | 1 ml/hr |
| 15 | SAGM+PRP | 2-3 hrs apart | pumped into trachea | 0.5 ml/hr |
| 16 | KGF-Hydrogel | 1 | pumped into trachea | 0.5 ml/hr |
| 16 | Primary Lung Cells | 2-60 minutes apart | pumped into trachea | 1 ml/hr |
| 16 | M2 Sup | 2-60 minutes apart | pumped into trachea | 1 ml/hr |
| 18 | PRP+MSC Sup | 2-60 minutes apart | pumped into trachea | 1 ml/hr |
| 19 | Lung cells | 2-3 hrs apart | pumped into trachea | 0.5 ml/hr |
| 20 | M2 Sup | 2- 2 hours apart | pumped into trachea | 1 ml/hr |
| 21 | Primary Lung Cells | 2-3 hrs apart | pumped into trachea | 0.5 ml/hr |
| 22 | SAGM+PRP | 2- 2 hours apart | pumped into trachea | 1 ml/hr |
| 23 | Primary Lung Cells | 2-3 hrs apart | pumped into trachea | 0.5 ml/hr |
| 24 | Primary Lung Cells | 2-3 hrs apart | pumped into trachea | 0.5 ml/hr |
| 25 | Primary Tracheal-Bronchial Cells | 2- 2 hours apart | pumped into trachea | 0.5 ml/hr |
| 26 | M2 Cell Sup | 2-3 hrs apart | pumped into trachea and PA | 0.5 ml/hr |
| 27 | M2 Cells | 2- 2 hours apart | pumped into trachea and PA | 0.5 ml/hr |
| 28 | MSC | 2- 2 hours apart | pumped into trachea and PA | 0.5 ml/hr |
| 30 | MNLs + Serum | 1 installation | pumped into PA | 1 ml/hr |
| 30 | Alveolar Macrophages | 1 installation | pumped into trachea | 1 ml/hr |

Figure 12. Cell Installation Information.

| Day | Cell Type Installed | Pig 1 | Pig 2 | Pig 3 | Pig 4 | Pig 5 | Pig 6 |
|---|---|---|---|---|---|---|---|
| 1 | PV | 131 | 118 | 125 | 280 | 123 | 97 |
| 2 | PV | 120 | 36 | 61 | 171 | 25 | 103 |
| 5 | PV | 116.8 | 168.2 | 82.5 | 167 | 129 | 54 |
| 7 | PV | 12.8 | 5.2 | 12.2 | 18 | 17 | 69 |
| 10 | PV | 20.6 | 44 | 35.7 | 39 | 37 | 57 |
| | Total PV Installed | 401.2 | 371.4 | 316.4 | 675 | 331 | 380 |
| 11 | PBMC | 135 | 197 | 116 | 215 | 218 | 145 |
| 16 | PL | 125 | 144 | 69 | 142 | 110 | 122 |
| 19 | PL | 122 | 127 | 83 | 131 | 128 | 97 |
| 21 | PL | 113 | 114 | 61 | 124 | 131 | 92 |
| 23 | PL | 134 | 132 | 72 | 131 | 141 | 104 |
| 24 | PL | 32 | 45 | 49 | 18 | 27 | 53 |
| | Total PL Installed | 644 | 682 | 515 | 707 | 689 | 699 |
| 25 | Trachea/ Bronchiole | 112 | 195 | 186 | 148 | 138 | 127 |
| 27 | M2 cells | 35 | 27 | 25 | 29 | 41 | 32 |
| 28 | MSC | 45 | 35 | 37 | 31 | 37 | 39 |
| 30 | Alv Macs | 9 | 8 | 11 | 14 | 16 | 17 |
| 30 | MNL | 257 | 370 | 275 | 289 | 271 | 223 |

Figure 13. Number of Cells Installed in Scaffolds.

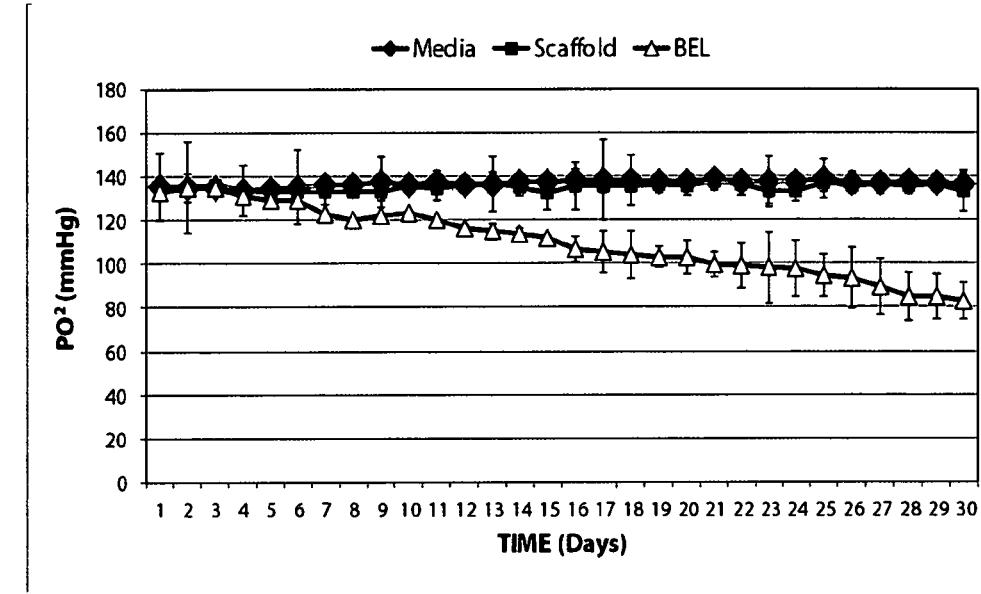
Figure 14. Bioreactor Culture BEL PO₂ measurements.

A
| Animal | Sex | Weight Pre (TX) | Weight Post (TX) | CFSE-Labeled Cells | Survival Time |
|---|---|---|---|---|---|
| Pig 1 | Male | 25 KG | 31.2 KG | NA | 2 Weeks |
| Pig 2 | Female | 40.5 KG | 40.5 KG | MNLs | 10 Hours |
| Pig 3 | Female | 30.1 KG | 39 KG | Primary Lung | SC |
| Pig 4 | Male | 28.5 KG | 38 KG | Primary Vascular | 1 Month |
| Pig 5 | Male | 66 KG | 75 KG | NA | 2 Month |
| Pig 6 | Male | 29 KG | 40.5 KG | Primary Vascular | SC |
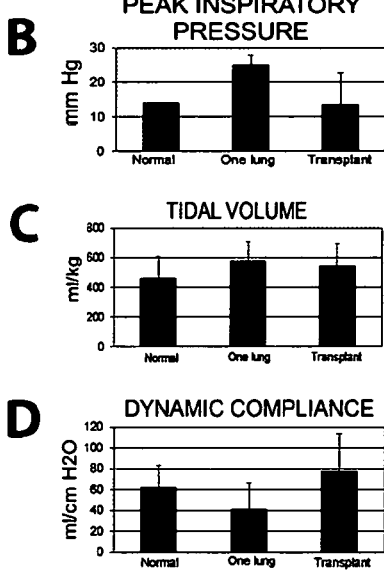
B PEAK INSPIRATORY PRESSURE
C TIDAL VOLUME
D DYNAMIC COMPLIANCE
Figure 16. Information Regarding Study Animals.

Genes Expressed in BEL compared to NL Related to Angiogenesis

| FOLD INCREASE | GENE ID | GENE NAME | DESCRIPTION |
|---|---|---|---|
| 5 | ENSSSCG00000001556 | MAPK14 | Map Kinase 14 |
| 5 | ENSSSCG00000010816 | TGFB2 | Transforming Growth Factor Beta 2 |
| 3 | ENSSSCG00000024960 | PDGFC | Platelet Derived Growth Factor C |
| 3 | ENSSSCG00000006862 | VCAM1 | Vascular cell adhesion molecule 1 |
| 3 | ENSSSCG00000012135 | VEGFD | Vascular endothelium growth factor D |
| 3 | ENSSSCG00000006159 | HEY1 | Hes Related Family BHLT Transcription Factor with YRPW Motif 1 |
| 3 | ENSSSCG0000001725 | SRY-Box-9 | Sex-determining region 9 (SOX 9) |
| 2.5 | ENSSSCG00000024651 | HEYL | Hes Related Family BHLT Transcription Factor with YRPW Motif-Like |
| 2.5 | ENSSSCG00000008841 | PDGFRA | Platelet Derived Growth Factor Receptor Alpha |
| 2.25 | ENSSSCG00000016416 | SHH | Sonic Hedgehog |
| 2 | ENSSSCG0000001795 | SRY-Box-15 | Sex determining factor 15 (SOX 15) |
| 2 | ENSSSCG0000001581 | FGFR1 | Fibroblast Growth Factor Receptor 1 |
| 2 | ENSSCCG0000000610 | SELP | Selectin P |
| 2 | ENSSSCG0000000182 | WNT10B | WNT family member 10B |
| 2 | ENSSSCG00000002906 | ETV2 | ETS Variant 2 |
| 2 | ENSSSCG00000013655 | ICAM1 | Intracellular adhesion molecule 1 |
| 1.55 | ENSSSCGC000000884 | KDR/VEGFR2 | Kinase Insert Domain Receptor |
| 1.33 | ENSSSCG0000001041 | CXCL12/SDF-1 | Stromal Derived Factor1 |
| 1.29 | ESSSCG00000022318 | ERG | ETS-related gene |
| 1.28 | ENSSSCG00000011102 | NRP1 | Neuropilin 1 |
| 1.25 | ENSSSCG0000000108 | SRY-Box 4 | Sex determining factor 4 (SOX 4) |
| 1.17 | ENSSSC0000001568 | CXCR4 | C-X-C Motif Chemokine receptor 4 |
| 1.00 | ENSSSCG0000001735 | ITGA2B/CD41 | Integrin subunit alpha 2b |
| 1 | ENSSSCG00000015235 | ETS1 | ETS proto-oncogene 1, transcription factor |
| 1 | ENSSSCG00000003017 | TGFB1 | Transforming Growth Factor Beta 1 |
| 1 | ENSSSCG00000004223 | HEY2 | Hes Related Family BHLT Transcription Factor with YRPW Motif 2 |
| 1 | ENSSSCG00000015584 | PROX1 | Prospero homeobox 1 |
| 1 | ENSSSCG00000015770 | VEGFC | Vascular endothelium growth factor C |
| 1 | ENSSSCG00000017277 | PECAM1 | Platelet and endothelial adhesion molecule 1 |
| 1 | ENSSSCG00000017755 | NOS2 | Inducible nitric oxide synthase |
| 1 | ENSSSCG00000009856 | NOS1 | Neuronal nitric oxide synthase |
| 1 | ENSSSCG00000006286 | SELE | Selectin E |

FIG. 17

| FOLD INCREASE | Gene ID | GENE NAME | DESCRIPTION |
|---|---|---|---|
| Epithelial Lineage | | | |
| 1.4 | ENSSSCG00000001945 | NKX2-1 | NK2 homeobox 1 or TTF-1 |
| AEC Type I Cells | | | |
| 2 | ENSSSCG00000000211 | AQP5 | Aquaporin-1 |
| 2 | ENSSSCG00000007836 | SCNN1G | Sodium Channel Epithelial 1 Gamma Subunit |
| 1.23 | ENSSSCG00000016634 | CAV1 | Caveolin-1 |
| 1 | ENSSSCG00000001437 | Rage/Ager | Receptor for advanced glycation end product |
| AEC Type II Cells | | | |
| 1.15 | ENSSSCG00000009619 | SFTPC | Surfactant Protein C |
| 1 | ENSSSCG00000008229 | SFTPB | Surfactant Protein b |
| 0.82 | ENSSSCG00000010334 | SFTPD | Surfactant Protein D |
| 0.48 | ENSSSCG00000010336 | SFTPA1 | Surfactant Protein A1 |
| Epithelial Cell Related Genes | | | |
| 2 | ENSSSCG00000000253 | KRT18 | Cytokeratin 18* |
| 1 | ENSSSCG00000011851 | MUC20 | Mucin 20, Cell Surface Associated |
| 1 | ENSSSCG00000011862 | MUC13 | Mucin 13, Cell Surface Associated |
| 1 | ENSSSCG00000013340 | MUC15 | Mucin 15, Cell Surface Associated |
| 1 | ENSSSCG00000025592 | TP63 | Tumor Protein P63 |
| 0.5 | ENSSSCG00000006525 | MUC1 | Mucin 1, Cell Surface Associated |
| 0.5 | ENSSSCG00000000248 | KRT5 | Keratin 5 |
| Neuroendocrine Cell Related Genes | | | |
| 1 | ENSSSCG00000002456 | CHGA | Chromogranin A |
| 0.83 | ENSSSCG00000028373 | ENO2 | Enolase 2 |
| 05 | ENSSSCG00000000992 | FOXF2 | Forkhead box 2 |
| Clara Cell Related Genes | | | |
| 0.83 | ENSSSCG00000024111 | SCGβ3A2 | Secretoglobin Family 3A Member 2 |
| Muscle Cell Related Genes | | | |
| 3.5 | ENSSSCG00000008294 | ACTG2 | Smooth Muscle Actin |
| 1.8 | ENSSSCG00000010190 | ACTA1 | Skeletal Muscle Actin |
| 0.51 | ENSSSCG00000007585 | ACTB | Encodes Actin Proteases |
| 0.5 | ENSSSCG00000010447 | ACTA2 | Smooth Muscle Actin |

Figure 18. RNA Sequence Data, Cell Lineage.

| Antibody Description | Animal Source | Abbreviation | Dilution | Clone | Company | Secondary Antibody | Company |
|---|---|---|---|---|---|---|---|
| Pro-surfactant protein C | rabbit | P-SPC | 1:200 | | Novus Biologicals, LLC – Littleton, CO | Goat anti-rabbit rhodamine | EMD Millipore Merck KgaA, Darmstadt, Germany |
| Aquaporin-5 | goat | AQP-5 | 1:50 | | Santa Cruz Biotechnology, Inc – Dallas, TX | Rabbit anti goat FITC | Santa Cruz Biotechnology, Inc. |
| Fibroblast specific protein-1 | rabbit | FSP-1 | | | Merck Millipore – Billerica, MA | Goat anti rabbit rhodamine | EMD Millipore |
| Vascular endothelial growth factor | mouse monoclonal | VEGF | 1 to 500 | 26503 | Sigma Aldrich, St. Louis, MO | Goat anti mouse Rhodamine red X | Thermo Scientific |
| Keratinocyte growth factor | mouse monoclonal | KGF | 1 to 500 | | Thermo Scientific | Goat anti-mouse alexa fluor 488 | Thermo Scientific |
| Fibroblast Growth Factor 2 | | FGF2 | | | | Goat anti-mouse alexa fluor 488 | Thermo Scientific |
| Ki67 protein | rabbit polyclonal Conjugated to Alexa Fluor 488 orDyLight 550 | Ki67 | 1 to 350 | | Novus Biologicals, Littleton, CO | | |
| Smooth muscle actin | mouse monoclonal | SMA | 1 to 400 | 1A4 | Sigma Aldrich | Donkey anti-mouse DyLight 550 | Thermo Scientific |
| Platelet endothelial cell adhesion molecule-1 | mouse monoclonal | CD31 | 1 to 100 | LCI-4 | BD Biosciences, San Jose, CA or Novus Biologicals | Novus is conjugated to Alexa Fluor 488 | Thermo Scientific |
| Vascular endothelial cadherin | mouse monoclonal | VE-Cadherin | 1 to 500 | BV9 | BD Biosciences, | Goat anti-mouse alexa fluor 488 | Thermo Scientific |
| Angiotensin converting enzyme | mouse monoclonal | ACE | 1 to 200 | E-9 | Sigma Aldrich | Donkey anti-mouse AlexaFluor 555 | Thermo Scientific |
| ERG transcription factor | mouse monoclonal | ERG | 1 to 200 | 5H6A12 | Thermo Scientific | Goat anti mouse Rhodamine red X | Thermo Scientific |
| Endothelial nitric oxide synthase | rabbit polyclonal | ENOS | 1 to 200 | | Abcam, Inc., Cambridge, MA | Chicken anti-rabbit DyLight 594 | Novus Biologicals, Littleton, CO |
| Tyrosine kinase kit | rabbit monoclonal | C-kit | 1 to 200 | 53H8L2 9 | Thermo Scientific | Goat anti mouse Rhodamine red X | Thermo Scientific |
| Lymphatic vessel endothelial hyaluronan receptor 1 | goat | LYVE-1 | 1 to 50 | V-15 | Santa Cruz Biotechnology, Inc | Goat anti-mouse alexa fluor 488 | Thermo Scientific |
| Pan cytokeratin | mouse monoclonal | pan-CK | 1 to 500 | MA5-13156 | Thermo Scientific | Goat anti-mouse alexa fluor 488 | Thermo Scientific |
| Cytokeratin 18 | mouse monoclonal | CK18 | 1 to 200 | RGE53 | Thermo Scientific | Goat anti mouse Rhodamine red X | Thermo Scientific |
| Epithelial cell adhesion molecule | mouse monoclonal | EP-CAM | 1 to 500 | MAB44 44 | EMD Millipore | Goat anti mouse Rhodamine red X | Thermo Scientific |
| Clara cell protein 10-FITC tagged | goat | CC10 | 1 to 100 | T-18 | Santa Cruz Biotechnology, Inc | Donkey anti-goat AlexaFluor 555 | Thermo Scientific |
| Mucin 1 | Mouse monoclonal conjugated to Alexa Fluor® 488 | MUC 1 | 1 to 100 | SM3 | Thermo Scientific | | |
| Mucin 5a | Mouse monoclonal | MUC 5a | 1 to 100 | 45M1 | Thermo Scientific | Goat anti mouse Rhodamine red X | Thermo Scientific |
| Cytokeratin 5 | mouse monoclonal | CK5 | 1 to 500 | 4A4 | Thermo Scientific | Goat anti mouse Rhodamine red X | Thermo Scientific |
| Tumor protein P63 | mouse monoclonal | P63 | 1 to 200 | 2C2 | Sigma Aldrich | Goat anti mouse Rhodamine red X | Thermo Scientific |

Figure 23. Antibodies Used For Cell Phenotype Analysis.

| Antibody Description | Animal | Clone | Fluorochrome | Company | Secondary Antibody | Company |
|---|---|---|---|---|---|---|
| CD14 | mouse monoclonal | M PΦ-9 | APC | BD Biosciences, San Diego California | | |
| CD45 | mouse monoclonal | HI30 | FITC | BD Biosciences | | |
| CD34 | mouse monoclonal | 581 | PECY5 | BD Biosciences | | |
| CD105 | mouse monoclonal | 266 | APC | BD Biosciences | | |
| CD90 | mouse monoclonal | 5E10 | FITC | BD Biosciences | | |
| CD29 | mouse monoclonal | MAR4 | PE | BD Biosciences | | |
| CD68 | mouse monoclonal | Y1/82A | PECY5 | BD Biosciences | | |
| CD80 | mouse monoclonal | L307.4 | FITC | BD Biosciences | | |
| CD163 | mouse monoclonal | GHI/61 | PE | BD Biosciences | | |
| CD206 | mouse monoclonal | 19.2 | PECY5 | BD Biosciences | | |
| CD4 | mouse monoclonal | SK3 | FITC | BD Biosciences | | |
| CD8 | mouse monoclonal | H1 | FITC | BD Biosciences | | |
| CD8 | Rabbit | RPA-T8 | PE | BD Biosciences | | |
| CD3 | mouse monoclonal | UCHT1 | APC | BD Biosciences | | |
| CD20 | mouse monoclonal | 2H7 | PE | BD Biosciences | | |
| Perforin | mouse monoclonal | delta-G9 | PE | BD Biosciences | | |
| Immunoglobulin G | goat | | not conjugated | Thermo Fisher | Rabbit anti goat FITC | Thermo Fisher Scientific |

Figure 24. Antibodies Used For Flow Cytometry Analysis.

| Swine Lung MB Primer | Forward | Reverse | Annealing Temp | Reference |
|---|---|---|---|---|
| Actinobacillus | TTCATACTGGGTCGCTAG | TCCACATCTCTACGCATT | 58 | This study |
| Aeromonas | GCATTTGAAACTGACAAG | TATTCCTCCAGATCTCTAC | 60 | This study |
| Enterococcus | AGAAATTCCAAACGAACTTG | CAGTGCTCTACCTCCATCATT | 62 | Water Research 39 (2005) 559–568 |
| Fastidiosipila | TTCCTAGTGTAGCGGTAA | AGTTRATAGCCAGAAAGC | 60 | This study |
| Fusobacterium | TGGTTATRTAAGTCTGATGT | CACTTGTAGTTCCGCTTA | 60 | This study |
| Gemella | TAATAAGTCTGATGTGAAAG | GTTCCTCCTAATCTCTAC | 56 | This study |
| Haemophilus | GGAGTGGGTTGTACCAGAAGTAGAT | AGGAGGTGATCCAACCGCA | 62 | Journal of Clinical Microbiology, May 1998, p. 1185–1188 |
| Haemophilus parasuis rpoB | CCGTAAAGTTGTGAATGG | GGAAGTTCTCATCTAAGTTTG | 58 | This study |
| Haemophilus parasuis CT inf | CGACTTACTTGAAGCCATTCTTCTT | CCGCTTGCCATACCCTCTT | 58 | Journal of Applied Microbiology 108 (2010) 1323–1331 |
| IOLA | ATGTCTGCTCAATCAATACTTG | AACACTTGCTTCTCTTCCA | 56 | This study |
| Leptotrichia Swine | GGRCGGAACTACACGAGTA | TCCAGTGARCTATCTTCATCATC | 56 | This study |
| Methanobrevibacter – Archaea | TTAGGTAGTTGGTTAGGTAATG | TTGTCTCAGGTTCCATCT | 60 | This study |
| Moraxella | CTTCCTGGCATCATACTG | CAACGACTGGTAGACATC | 60 | This study |
| Mycoplasma flocculare | GCGATGTTCACTCAACTCA | GCGGCTGTTAGTCAATGA | 60 | This study |
| Mycoplasma hyorhinis | TATCTCATTGACCTTGACTAAC | ATTTTCGCCAATAGCATTTG | 58 | J. Clin. Microbiol. May 2014 vol. 52 no. 5 1664-1671 |
| Mycoplasma suis | CCC TGATTGTACTAATTGAATAAG | GCGAACACTTGTTAAGCAAG | 58 | Journal of Applied Microbiology 111, 417–425 |
| Paraprevotella | GCGGTAAACGATGGATGC | CCAGGTGGGATGCTTAAC | 62 | This study |
| Peptostreptococcus | TCATAGGAGGAAGCCCTGGCTAAA | TAAGCTCCACGCTTTGACACCTGA | 62 | J Clin Microbiol 2010: 48; 1812-1819 |
| Porphyromonas Swine | TCACGAGGAACTCCGATT | TGTTTGATACCCACGCTTT | 60 | This study |
| Prevotella sp | GGGATGCGTCTGATTAGCTTGTT | CTGCACGCTACTTGGCTGGTTC | 62 | J Clin Microbiol 2010: 48; 1812-1819 |
| Pseudomonas | ACTTTAAGTTGGGAGGAAGGG | ACACAGGAAATTCCACCACCC | 60 | FEMS Microbiol Lett 333 (2012) 77–84 |
| Staphylococcus | GAACGTGGTCAAATCAAAGTTGGTGAAGA | GTCACCAGCTTCAGCGTAGTCTAATA | 62 | J Clin Microbiol, Oct. 2009, p. 3129–3137 |
| Streptococcus | AGTCGGTGAGGTAACCGTAAG | AGGAGGTGATCCAACCGCA | 62 | Journal of Clinical Microbiology, May 1998, p. 1185–1188 |
| Universal 16s | TCCTACGGGAGGCAGCAGT | GGACTACCAGGGTATCTAATCCTGTT | 62 | J Clin Microbiol 41:4796-4798. |
| CHMP2A – Swine HK | ACGCTCAAGTCTAACAAC | CATCGTTCATCATCTCCTC | 60 | This study |

Figure 25. Microbiome Primers Used In This Study.

| Antibody Description | Animal Source | Abbreviation | Dilution | Clone | Company | Secondary Antibody | Company |
|---|---|---|---|---|---|---|---|
| Fibroblast specific protein-1 | rabbit | FSP-1 | 1 to 300 | | Merck Millipore | Goat anti rabbit rhodamine | EMD Millipore |
| Vascular endothelial growth factor | mouse monoclonal | VEGF | 1 to 500 | 26503 | Sigma Aldrich | Goat anti mouse Rhodamine red X | Thermo Fisher Scientific |
| Smooth muscle actin | mouse monoclonal | SM M ACT | 1 to 400 | 1A4 | Sigma Aldrich | Donkey anti-mouse DyLight 550 | Thermo Fisher Scientific |
| Platelet endothelial cell adhesion molecule-1 | mouse monoclonal | CD31 | 1 to 100 | LCI-4 | BD Biosciences or Novus Biologicals | Novus is conjugated to Alexa Fluor 488 | Thermo Fisher Scientific |
| Vascular endothelial cadherin | mouse monoclonal | VE-CAD | 1 to 500 | BV9 | BD Biosciences, | Goat anti-mouse alexa fluor 488 | Thermo Fisher Scientific |

FIG. 26

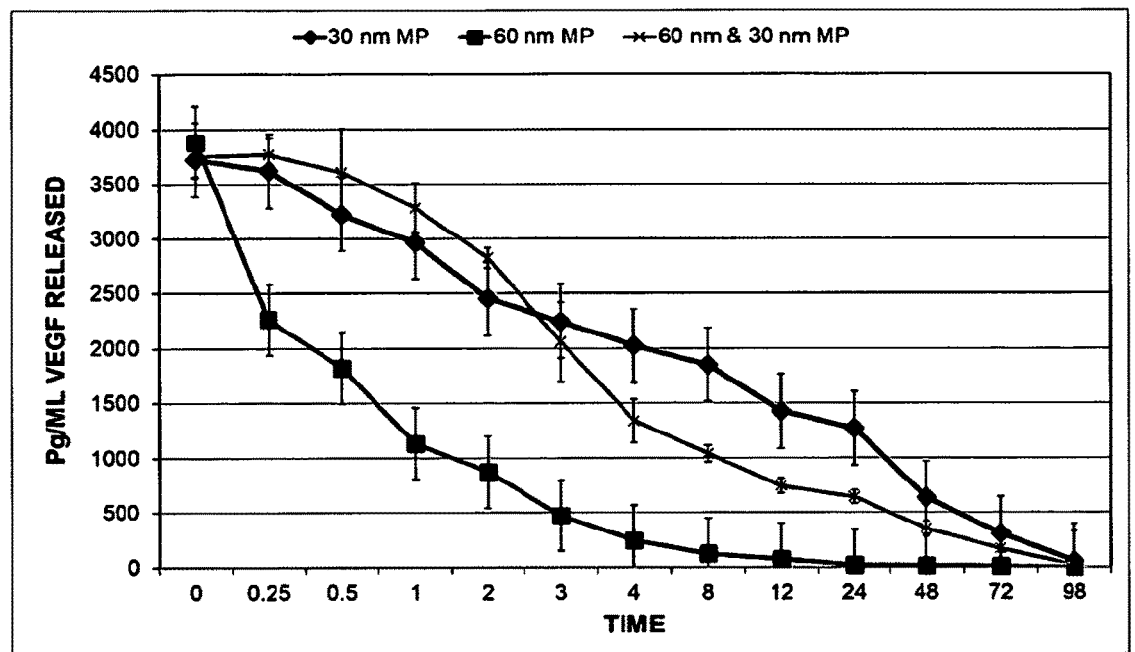
Figure 29. VEGF Load Release.

PRODUCTION OF A BIOENGINEERED LUNG

RELATED APPLICATIONS

This application is a national phase application under 35 U.S.C. § 371 of International Application No. PCT/US2019/028162, filed Apr. 18, 2019, which claims priority to U.S. Provisional Application No. 62/659,321, filed on Apr. 18, 2018, the entire contents of which are incorporated herein.

FIELD OF THE INVENTION

The invention generally relates to methods for producing a bioengineered lung (BEL) suitable for implantation into a transplant recipient and the use thereof for transplantation and for the study of the lung microbiome and its role in lung development and remodeling.

BACKGROUND OF THE INVENTION

Advances in the production of bioengineered lung (BEL) (1-4) have not been matched in the development of functional vascular tissue (5-9). Whole BEL produced on acellular (AC) lung scaffolds have been transplanted in small animal models, but lungs failed due to intravascular coagulation and defects in endothelial barrier function leading to pulmonary edema (2, 3, 9). No approach has allowed for long-term survival of BEL following transplantation.

A fundamental problem facing the field of tissue engineering is our lack of ability to produce perfusable microvasculature networks capable of supporting tissue survival or of withstanding physiological pressures without leakage. This is critically important for production of BEL, which requires systemic circulation to support tissue survival and coordination of circulatory and respiratory systems to ensure proper gas exchange.

The lung is unique because it contains both a pulmonary circulation and a systemic or bronchial circulation originating at the aorta (Ao) (11, 12). The bronchial circulation provides nutrients and oxygen to the lung parenchyma, pleura, airways and blood vessels while the pulmonary circulation is essential for gas exchange. Work examining passive diffusion of gas into the lung, suggests that non-vascularized lung can survive for periods of time without vascular support (10) or ligation of the pulmonary artery (Pa) (11, 12). Thus, there is a need for BELs which can provide development of the bronchial systemic circulation to support BEL growth and survival following transplantation.

BRIEF SUMMARY OF THE INVENTION

The invention in general relates to methods for producing a bioengineered lung (BEL). In some exemplary embodiments the method comprises obtaining an acellular (AC) lung scaffold, treating the AC lung scaffold with one or more growth factors, seeding the treated AC lung scaffold with primary lung cells, and culturing the seeded AC lung scaffold in a bioreactor to produce the BEL.

In some exemplary embodiments, the methods for producing a bioengineered lung (BEL) further comprises reconstituting the immune system of the BEL by the addition of immune cells during culturing.

In some exemplary embodiments, the treated AC lung scaffold is seeded with primary lung cells and vascular cells optionally isolated from whole lung and peripheral blood.

In some exemplary embodiments, the primary lung cells are derived from a large mammal.

In some exemplary embodiments, the primary lung cells are derived from a pig, sheep, goat or other ungulate or bovine or are derived from a human or non-human primate. Preferably, the primary lung cells are of porcine origin.

In some exemplary embodiments, said primary lung cells are obtained from a biopsy or pneumonectomy of lung which biopsy or pneumonectomy optionally is pretreated with dextrose prior to decellularization wherein decellularization optionally is effected using sodium dodecyl sulfate (SDS).

In some exemplary embodiments, step (b) comprises treating the AC lung scaffold with one or more growth factors and platelet rich plasma which promote angiogenesis and the functionality of the BEL after transplantation.

In some exemplary embodiments, step (b) comprises treating the AC lung scaffold with one or more growth factors at least some of which are loaded onto microparticles or nanoparticles and/or are delivered using a hydrogel.

In some exemplary embodiments, step (b) comprises treating the AC lung scaffold with VEGF, FGF2, KGR, or any combination thereof. Optionally, step (b) comprises treating the AC lung scaffold with VEGF and FGF2.

In some exemplary embodiments, step (b) comprises treating the AC lung scaffold with microparticles or nanoparticles comprising VEGF and a hydrogel comprising FGF2.

In some exemplary embodiments, step (b) comprises treating the AC lung scaffold with microparticles or nanoparticles comprising VEGF and a hydrogel comprising FGF2, a hydrogel comprising KGR, and a hydrogel comprising platelet rich plasma.

In some exemplary embodiments, the microparticles or nanoparticles used to deliver growth factors comprise non-spherical microparticles or nanoparticles, e.g. non-spherical or discoidal porous silicon microparticles or nanoparticles comprising pores optionally of different sizes, further optionally 30 or 60 nm size pores.

In some exemplary embodiments, the primary lung cells comprise primary vascular cells.

In some exemplary embodiments, the BEL is cultured on the AC lung scaffold for about 30 days or more prior to transplantation into a recipient.

In some exemplary embodiments, the immune system of the BEL is reconstituted by the addition of mononuclear leukocytes (MNLs), optionally autologous, to the bioreactor culture optionally at about day 11 of culture.

In some exemplary embodiments, the immune system of the BEL is reconstituted by the addition of serum, alveolar macrophages (AMs) and mononuclear leukocytes (MNLs), optionally autologous, to the bioreactor culture optionally around day 30 prior to transplant.

In some exemplary embodiments, said MNLs comprise T lymphocytes (CD4 and CD8 T lymphocytes), macrophages, and B lymphocytes including IgG positive B lymphocytes.

In some exemplary embodiments, step (b) comprises treating the AC lung scaffold with microparticles or nanoparticles comprising one or more growth factors, wherein said microparticles or nanoparticles comprise a mixture of microparticles or nanoparticles having a pore size of 60 nm and microparticles or nanoparticles having a pore size of 30 nm.

The ratio of microparticles or nanoparticles having a pore size of 30 nm to microparticles or nanoparticles having a pore size of 60 nm can in some exemplary embodiments be in a range selected from 10:1 to 1:10, 5:1 to 1:5, 4:1 to 1:4, 3:1 to 1:3, 2:1 to 1:2, and 1.5:1 to 1:1.5. In some exemplary embodiments, the ratio of microparticles or nanoparticles having a pore size of 30 nm to microparticles or nanoparticles having a pore size of 60 nm is 1:1.

In some exemplary embodiments, the microparticles or nanoparticles comprise one or more growth factors selected from VEGF, FGF2, and KGR.

In some exemplary embodiments, the microparticles or nanoparticles comprise non-sp porous silicon microparticles or nanoparticles.

In some exemplary embodiments, the microparticles or nanoparticles are delivered to the AC lung scaffold via the pulmonary artery of the AC lung scaffold.

The present invention also provides a method for producing a bioengineered lung (BEL) having a reconstituted immune system, comprising obtaining an acellular (AC) lung scaffold, seeding the treated AC lung scaffold with primary lung cells, and culturing the seeded AC lung scaffold in a bioreactor to produce the BEL, wherein the culturing step comprises adding immune cells to the BEL during culturing in order to reconstitute the immune system.

In some exemplary embodiments, said immune cells comprise mononuclear leukocytes, optionally autologous mononuclear leukocytes.

In some exemplary embodiments, the culturing step further comprises adding at least one of serum and alveolar macrophages to the BEL during culturing.

In some exemplary embodiments, the mononuclear leukocytes comprise any one or more of T-lymphocytes (CD4 and CD8 T lymphocytes), macrophages, and B-lymphocytes.

In some exemplary embodiments, autologous MNLs are added around day 11 of bioreactor culture.

In some exemplary embodiments, autologous serum, alveolar macrophages and MNLs are added to the bioreactor culture around 30 days prior to transplantation.

The invention also provides for a BEL produced by any of the methods described in the application.

In addition, the invention relates to a method of transplanting a lung, comprising transplanting into a subject in need thereof a BEL produced according to the methods described in the application.

In some exemplary embodiments, the subject has a lung disease or disorder.

In some exemplary embodiments, the lung disease or disorder is selected from pulmonary parenchymal disease, diffuse parenchymal lung disease, interstitial lung disease, pulmonary vascular disease, cystic fibrosis, surfactant dysfunction disorders, pulmonary hypertension, an injury or damage to pulmonary tissue, lung cancer and other pulmonary anatomical defects or disorders.

In some exemplary embodiments, the BEL is suitable for transplantation into an autologous, allogeneic or xenogeneic recipient.

In some exemplary embodiments, the transplant recipient is not immunosuppressed.

In some exemplary embodiments, the transplant recipient is immunosuppressed.

In some exemplary embodiments, the produced BEL prior to transplantation comprises developed microvasculature and optionally comprises no red blood cells.

In some exemplary embodiments, the BEL after transplantation survives for a long term and develops functional alveolar and vascular tissue.

In some exemplary embodiments, the BEL is transplanted with an airway (tracheal) anastomosis but without a vascular (pulmonary artery) anastomosis or connection to a pulmonary artery.

In some exemplary embodiments, the BEL post-transplant possesses some or all of the following properties: (i) well developed capillaries, (ii) collateral circulation observed about 2 weeks about post-transplant, (iii) blood vessels which express CD31, (iv) blood vessels which express angiogenesis markers such as transcription factor early growth response protein-1 (ERG) and/or endothelium nitric oxide synthase (eNOS), (v) blood vessels which express in response to shear stress of blood flow angiotensin converting enzyme (ACE), (vi) lymphatic vessel endothelial receptor-1 (LYVE) positive areas are detectable around 1 month post-transplant, (vii) lymphatic vessels throughout about 2 months post-transplant, (viii) intact vessels which support collateral systemic circulation observed about 2 weeks post-transplant (ix) detectable alveolar tissue detectable about 2 weeks post-transplant (x) continued cell proliferation, lung and vascular tissue development post-transplant without the addition of further exogenous growth factors, (xii) comprises bacteria and pulmonary microbiome communities present in normal pulmonary tissues optionally via tracheal transfer, and (xiii) elicits no rejection response post-transplant.

The invention also provides for methods of using a BEL produced according to any of the methods described herein to identify microbia which are comprised in the normal lung microbiome.

In some exemplary embodiments, the invention provides methods of using a BEL produced according to any of the methods described herein, to identify the effects of microbia which are comprised in the normal lung microbiome on the formation of alveolar tissues and remodeling.

In some exemplary embodiments, this analysis identifies microbia which are comprised in the normal lung microbiome and are not present in the microbiome of the normal gut.

In some exemplary embodiments, this analysis screens for bacteria, viruses and fungi commonly present in pig and human lungs.

In some exemplary embodiments, this analysis is effected using qPCR.

The invention further provides methods of treating a subject with absent or aberrant lung microbiome by administering microbia which are present in normal lung microbiome.

In some exemplary embodiments, said subject has been treated with an antibiotic, antiviral agent or other therapeutic which has depleted the normal lung microbiome.

In addition, the invention provides methods of promoting normal lung development by administering microbia which are present in the normal lung microbiome.

BRIEF DESCRIPTION OF THE DRAWINGS

FIG. 3. Genes Expressed in BEL. RNA-sequence analysis was used to evaluate gene expression in BEL. We used a Fold change (FC)>1 if gene expression value of BEL was greater than gene expression value of native lung: FC-1 if gene expression value of engineered lung was equal to gene expression value of NL and an FC<1 if gene expression value of engineered lung less than the gene expression value of NL. (A and B) Samples were removed from 3 different regions of the BEL and NL. Samples were examined and gene expression information is provided in the form of a (A) Heat Map generated based on top 1000 genes (ranked by P values) using Multiple Experiment Viewer software. This data shows the difference in levels of expression of BEL genes compared to NL. (B) Summary of genes in BEL exhibiting FC between 0-0.5, 0.5-2 or more than 2 fold changes in expression in BEL compared to NL, for tissue sets 1-3. (C) BEL genes of interest related to angiogenesis with FC>1 as compared to NL.

Figures 1A, 1B, 1C, 1D, 1E, 1F, 1G, 1H, 1I:
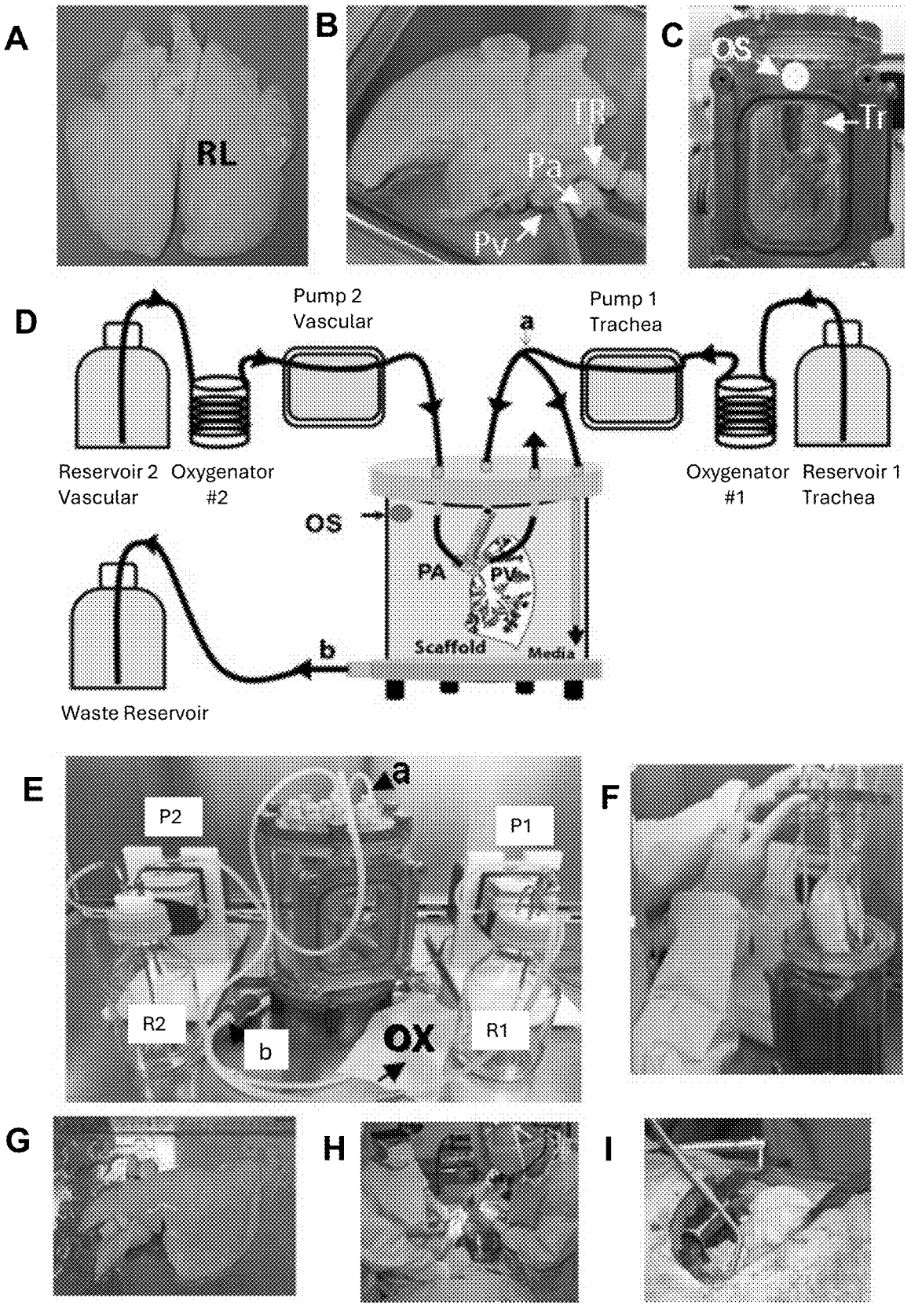
FIG. 1. Study Overview. (A) Left lung scaffolds produced from whole AC lungs. The right lung (RL) was removed to create a left lung scaffold. (B) Catheter placement in the trachea (Tr), pulmonary artery (Pa) and pulmonary vein (Pv). (C) Scaffolds were positioned in the bioreactor chamber to permit visualization of Pa and Pv catheters. The oxygen sensor (OS) position is noted. (D) Diagram of the fluidic system shows the microfluidic and pumping system supporting the bioreactor. For support of tracheal circulation, media flowed from reservoir-1 through the oxygenator (OX) to pump-1, then into the trachea at a or the bioreactor tank and out at point b, terminating at a waste container. For vascular circulation, media flowed from reservoir-2 through the oxygenator to pump-2, into the Pa (vascular system) and out of the Pv, returning to reservoir-2 to a waste container. (E) Image of system outlined in D above. (F and G) BEL being removed from bioreactor chamber on day 30. The BEL in F was produced using the scaffold shown in images A-C. (H) Image of BEL being prepared for transplant in surgical suite and (I) following the trachea-to-trachea anastomosis when the BEL expanded.

PVASC cells. (G) Overlay of CD31 (red) staining with CFSE. (H) DAPI (blue nuclei) staining control for I. (I) Junction of collateral vessel outside of the BEL. VE-Cadherin (red) endothelial cells with few CFSE-labeled cells PVASC cells (white arrow) were found where collateral vessels join with the BEL vasculature. (J-W) Cross sections of blood vessels in the BEL. (J, L, N, P, R) DAPI staining controls and sections stained for (K and M) CD31 (red), (O) ERG (red), (Q) ENOS (red) and (S) ACE (red), all of which are indicators of endothelial cell function. (T and V) DAPI control and representative image showing (U) LYVE-1 positive lymphatic cells at 2 weeks post-transplant and (W) LYVE-1 positive lymphatic cells 1 month post-transplant.

FIG. 5. Lung Tissue Development in BELs. (A) SEM of distal lung region of AC scaffold. (B) Representative image of methylene blue-stained thin section of BEL pre-transplantation highlighting compressed (non-aerated) regions (black arrows) and aerated spaces. (C) SEM of alveoli of BEL pre-transplant. (D) TEM image of aec II (insert, lamellar body) pre-transplant. (E-K) Evaluation of pig-4 BEL (1 month post-transplant). (E) SEM of BEL post-transplant shows increase in aerated alveolar regions due to normal breathing (white arrow). (F) TEM image of aec II (insert, lamellar body) post-transplant. (G) TEM of BEL containing aec I pneumocytes. (H-K) Representative images of lung tissue from pig-4, BEL. (H) DAPI stained control and (I) P-SPC (red) positive aec II. (J) DAPI stained control and (K) AQ-5 (green) positive aec I cells. (L-O) Averaged counts of total number of cells and the number of aec I cells in NL or BEL for pigs survived for (L) 10 hours, (M) 2 weeks, (N) 1 month or (O) 2 months. Student's t test was used to compare total number of cells and total numbers of aec I in NL and BEL. Analysis of variance (Anova) was used to assess statistical significance in the comparison of [(L) to (M), (N) and (O))] (*$p<0.001$) and [M and N to O] (**$p<0.0001$).

FIG. 6. Pig 5, Tissue Development. Pig-5 developed an airway occlusion post-transplantation. (A) Image of carina and (B) image of bronchial occlusion (arrow) and open airway or (C) bronchial occlusion alone (arrow) in left BEL. (D) Anastomosis site of BEL in recipient's trachea. (E) Chest x-ray of the non-aerated BEL, which is the dense homogeneous opacity, projecting over the mediastinum. Extensive compensatory hyperinflation of the NL is demonstrated. (F) Sagittal reformatted image of CT chest in venous phase through the left hemithorax shows collapsed BEL containing multiple small intercostal vessels (arrows). (G, I and L) DAPI stained controls and BEL in (G and H) aerated and (J-N) non-aerated regions containing P-SPC positive TUNEL+ (green) aec II cells. (H) P-SPC positive (red) cells with insert showing cell staining. (J and K) BEL in non-aerated regions stained for P-SPC (red) and TUNEL (green) a marker indicative of cells undergoing apoptosis. (L) DAPI stained control and (M and N) FSP-1 (red) fibroblasts in collapsed non-aerated regions. 5 randomly selected areas from 10 different sections of tissue immunostained for the presence of P-SPC+, tunnel+ or FSP−1+ cells from NL, aerated or non-aerated sections of BEL were examined. (0) Averaged number of cells, number of P-SPC positive aec II cells, TUNEL+ aec II and FSP-1+ cells plus the standard deviation is shown for NL, aerated and non-aerated BEL. As expected NL contained more cells and more aec II than NL. Data were analyzed using ANOVA.*$p<0.05$, $p<0.005$, *$p<0.0005$, not significant, NS.

FIG. 7. BEL Immune Response BAL was performed on all animals. (A and B) Examination of interleukin (IL)-8, 1L-1β, IL-6, IL-10, IL-12p70, IL-2, IL-4 and interferon gamma (IFN-λ) levels in BAL were examined for (A) NL and BEL pre-transplant and (B) showing NL and overlay of data from BALs evaluated at 10 hours, 2 weeks, 1 month or 2 months post-transplantation of the BEL. Data was graphed on a polar plot to highlight each individual animal's immune response. (A-D) BALs were done on NL at the time of the pneumonectomy and on BEL post euthanasia. (C) Number of CD8 cells isolated from BALs. (D) Percent of CD4– or CD8 positive T lymphocytes, perform positive cells or CD20 positive B-lymphocytes are shown. (E and G) DAPI stained controls and (F and H) representative images of CD8+T lymphocytes (green) in tissues of (G) NL or (H) BEL. (I) Averaged CD8+ cell counts for tissue sections for pigs-1, -2, -4 and -5 NL and BEL. Differences in BAL cell numbers, percent of lymphocytes or CD8 cells in tissues were not significant (NS). Analyses to compare NL to BEL per pig were done using student's t test.

FIG. 8. Analysis of BEL Microbiome (A) Representative SEM image of the native lung (NL) of pig-1 demonstrating the normal microbiome. (B) SEM image of sterile BEL pre-transplantation. (C) SEM of BEL 2 weeks post-transplantation showing reduced microbial colonization of BEL. The composition of each microbiome was evaluated for (D) tracheal and (E) lung samples from NL and BEL of pigs survived for 10 hours, 2 weeks or 1 month and are shown as proportional bar charts (average of at least two independent evaluations per sample). Data for NL and BEL are labeled at the top of each bar. Data indicates that tracheal and lung colonization occurred within 10 hours of BEL transplant, however the profile of these early communities appeared to be less stabilized with more bacterial targets detected in the trachea of the transplant relative to the NL.

FIG. 9. Scaffold Production and Modification. During scaffold production dextrose-pretreatment prior to SDS decellularization resulted in less damage to collagen fibers. (A) SDS decellularization alone and (B) dextrose pretreated lung. (C) SHG image stacks from regions of interest (ROI) confirmed that averaged collagen content was increased by dextrose-pretreatment. (*p<0.002) (D and E) SEM of VEGF-MPs. (F-J) Evaluation of effectiveness of scaffold delivery of growth factors on PVASC attachment for (F) Media, (G) VEGF-MP, (H) VEGF-MP and PF-127 loaded with FGF2 or (I) PF-127 hydrogel containing FGF2 alone. (J) Averaged data to examine attachment of cells after 3 days of culture for PVASC isolated from N=5 porcine cell donors with 5 replicates of each experiment to examine cell attachment for each pig donor. Data were analyzed using ANOVA. *p<0.0005. Best PVASC attachment occurred on MP+ hydrogel pretreated scaffolds. (K) Load release was measured following pretreatment of pieces of vascular or lung scaffold with MP or hydrogel loaded with growth factor. Media was removed at each time point and the supernatant was frozen at −70° C. until ELISAs were performed. (K) Averaged Load release data for four preparations of 30 or 60 urn pore size, VEGF-MP treated vascular scaffolds. (L) Averaged load release data for four preparations of FGF2-loaded hydrogel applied to vascular scaffolds or (L) KGF-loaded hydrogel applied to lung scaffolds. (M-P) Representative images confirm delivery of GF within the whole lung scaffolds. Biopsy sized pieces of whole scaffold were sectioned and stained with (M and N) anti-VEGF antibody (red) or (O) anti-FGF2 antibody (green) and DAPI nuclear stain. (P) Following PL installation sections were stained with anti-KGF antibody (green) and DAPI nuclear stain (blue) to demonstrate PL cell attachment to hydrogel treated scaffold.

Figures 10A, 10B, 10C:
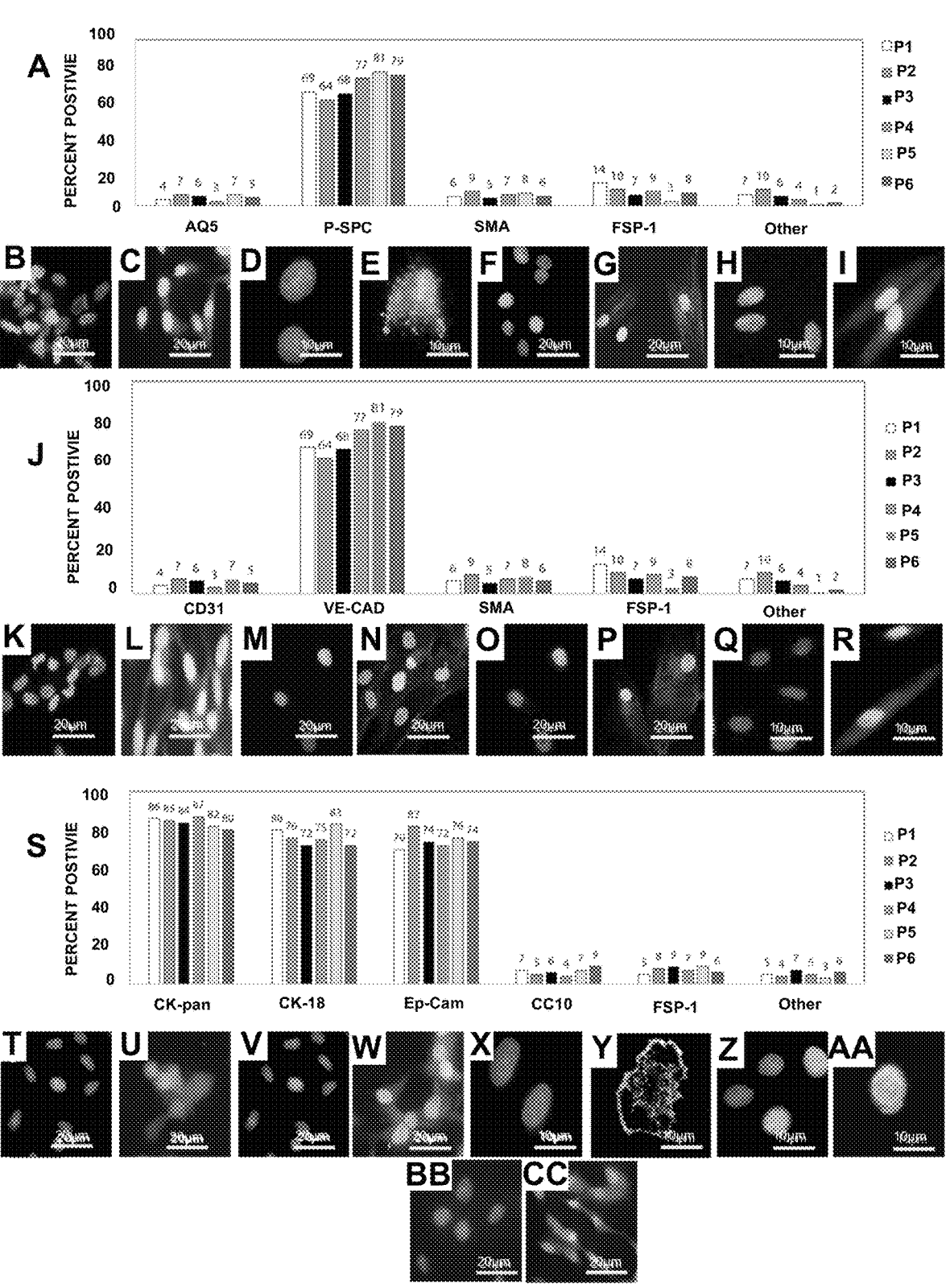

FIG. 10. Cell Phenotypes Installed in BEL. PL, PVASC and primary tracheal-bronchial cells (PTB) from pig-1 through 6 were used to recellularize the porcine left lung scaffolds. Cells were isolated from the left lung of each animal following a pneumonectomy. (A) Flow cytometry evaluation of phenotypes of PL cells isolated from pig 1-6. (B-I) Images showing morphological structure and pattern of staining for each cell type analyzed in (A). PLs were predominantly P-SPC positive, aec type II cells, although FSP-1 positive fibroblasts, AQP-5 aec type I cells and SMA positive cells were also seen. (J-R) Phenotypic profile of the PVASC installed in P 1-6. Percentage of cells positive for expression of CD31, VE-CAD, SMA and FSP-1 are shown. (K-R) Images showing morphological structure and pattern of staining for each cell type analyzed in (J) (S-CC) Phenotypic profile of the P trachea/bronchial cells used to recellularize Pigs 1-6. Percentage of cells positive for expression of CK-pan, CK-18, Ep-Cam, CC10 and FSP-1 are shown. (T-CC) Images show morphological structure and pattern of staining for each cell type analyzed in (S).

Figure 11A:
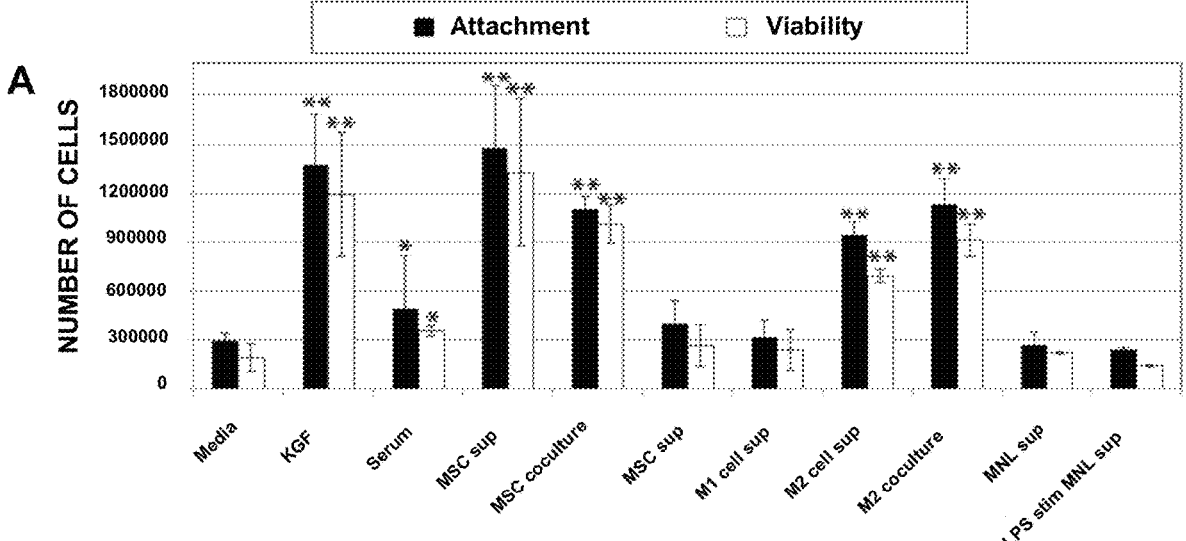
Figure 11B:
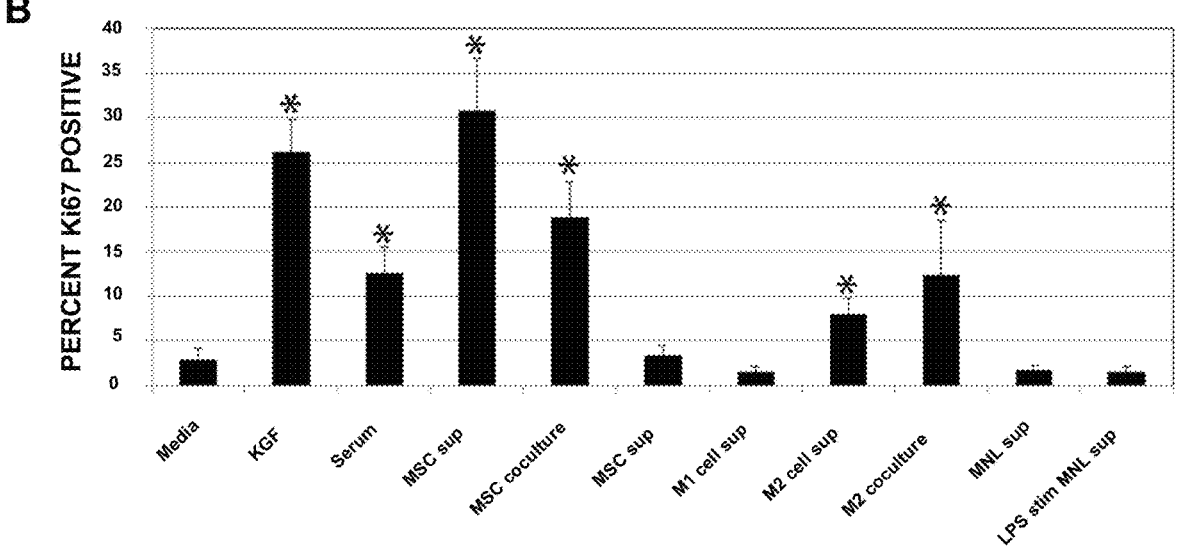

FIG. 11. BEL Culture Supplements. Potential scaffold supplements were selected based on PL attachment to treated pieces of AC lung scaffold. (A) Average attachment and PL viability data determined for untreated AC lung scaffold, or AC lung scaffold pretreated with hydrogel loaded with 50 ug/ml KGF (used as a positive control) or autologous; pig serum, MSCs (MSC sup), Macrophages (Mac sup), M1 macrophage supernatant (M1 sup), M2 macrophage supernatant (M2 sup), MNL supernatant (MNL sup) or LPS stimulated MNL supernatant (LPS stim MNL sup). Coculture with autologous MSC, macrophages, M1 macrophages, M2 macrophages, MNL or LPS stimulated MNL was also examined. Data were analyzed using ANOVA. *p<0.005, p<0.0005. (B) Proliferation of the PL in response to the same additives listed in (A) after 7 days of culture, determined using Ki76 staining. Data were analyzed using ANOVA. *p<0.005.

FIG. 12. Cell Installation Information. Process used to recellularize pig single left lung scaffolds. All AC left lung scaffolds were primed with porcine PRP, VEGF-MP, FGF2 hydrogel and KGF-hydrogel as described prior to installation of cells. PL, PVASC and P trachea/bronchial cells were installed on the scaffold via the PA (PV) or the trachea (PL and P trachea/bronchial cells). The day of installation, cell type installed into the scaffold, site of installation (PA or trachea), number of installations of each cell type, method of installation and flow rate during the installation are listed. PVASC or PL, M2 cells and MSC were counted, and divided into 2 aliquots, installed 60 minutes apart. Two aliquots of MNLs were added during culture. One aliquot was added on culture day 11 and one on the day of transplant. All pigs received a left BEL produced exclusively from their own cells but grown on an unrelated donor pig's scaffold.

FIG. 13. Number of Cells Installed in Scaffolds. The number of PVASC, PL, PTB, M2, MNL or MSCs installed into the AC left lung scaffold, and the day of installation of each cell type, is listed for each pig. Pigs-3 and -6 were euthanized due to surgical complications caused by the initial left lung pneumonectomy. BELs were produced for pig-3 and -6 but adhesion bands, which developed at the pneumonectomy site, prevented transplantation of the bio-engineered organ. Lungs for pig-3 and -6 were used to evaluate tissue production pre-transplant.

FIG. 14. Bioreactor Culture BEL PO2 measurements. PO2 was measured three times each day for each condition over 30 days of bioreactor culture. Measurements were made for the chamber with media alone, media with AC scaffold in place or for the BEL in the chamber. PO2 was measured in mmHg. The plot shows averaged values +/−Standard deviation for N=6 BEL.

Figures 15A, 15B, 15C, 15D, 15E, 15F:
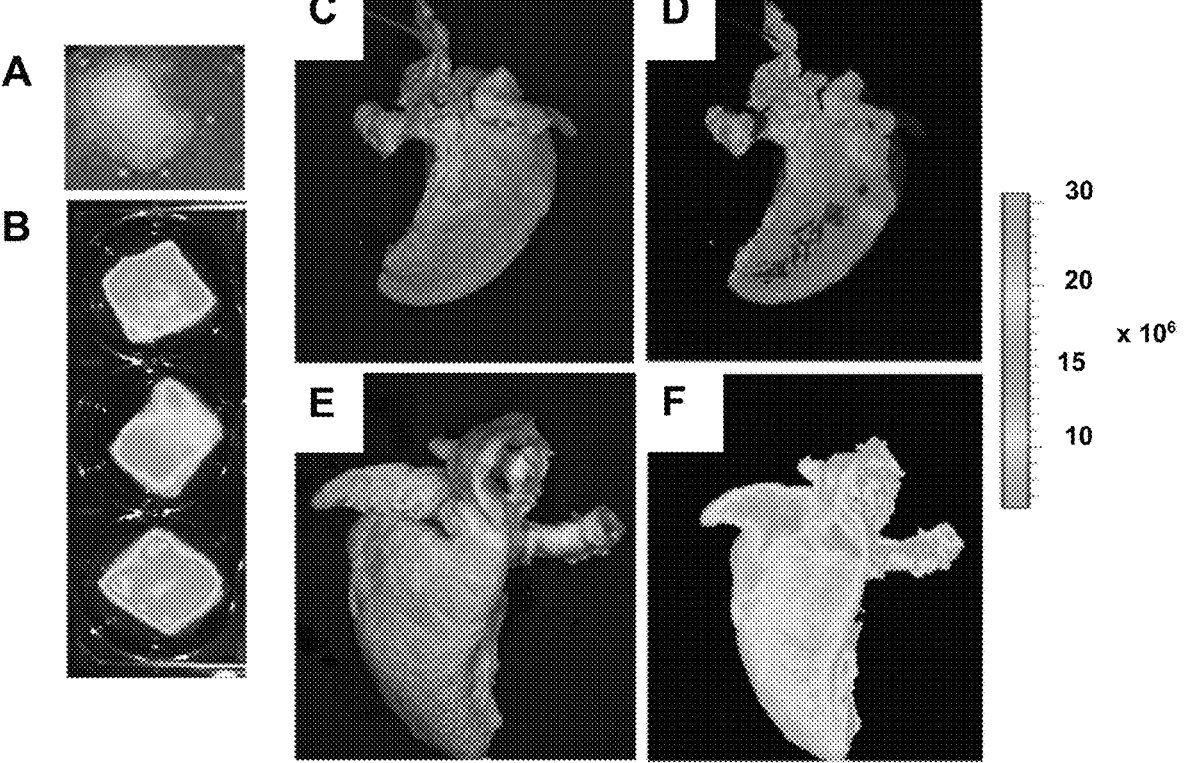

FIG. 15. IVIS Imaging to Estimate Cell Dispersal. An IVIS Spectrum in vivo imaging system was used to examine cell dispersal in small pieces of scaffold or in BEL. (A) Pieces of lung scaffold were IVIS imaged to determine fluorescence analysis cell count baselines. (A) A photograph of the 3×3×0.5 cm sized piece of AC lung containing (A) no cells (red) or (B) 1×106 CFSE labeled PL cells (green) per scaffold was imaged after 10 days of culture. (C) Photograph of a left lung scaffold. (D) High sensitivity IVIS in vivo image of this lung to examine distribution of cells. (E) Image of BEL and (F) IVIS in vivo image of the fluorescence provided by the CFSE labeled cells after 30 days of culture. At the left of the images is the fluorescence scale. Cell counts were estimated by optimizing the cell numbers using the small 3×3×0.5 cm sized pieces of lung to standardize the settings prior to imaging whole lungs.

FIG. 16. Information Regarding Study Animals. (A) Male or female Yorkshire pigs were used in this study. Animals had an average weight of 36.5 kg pre-transplantation and 45 kg pre-harvest except for pig-2 that was survived for 10 hours post-transplant. All animals underwent a left pneumonectomy at the beginning of the study. All animals underwent a left sided transplant of the BEL after 30 days. CFSE labeled cells (MNLs, PVasc or Plung) were installed for tracking purposes in specified animals. (B) Mean peak inspiratory pressure at baseline was measured at 14 cmH20 in the normal lung, 25 cmH20, during one lung ventilation, and returned to baseline measurement of 13 cmH20 post-transplant. (C) Mean Tidal Volume at baseline in the normal lung was 460 ml, one lung ventilation 578 ml and post-transplant 544 ml. (D) Dynamic compliance for pigs-1, -2, -4, and -5 was evaluated pre left lung pneumonectomy, pre-transplant of left lung, pre harvest. Dynamic compliance (Cdyn) in the normal lung at baseline was 63 ml/cmH20, during one lung ventilation Cdyn decreased to 41 ml/cmH20 and at transplant Cdyn increased to 77 ml/cmH20. In all animals the lung function returned to normal values by four hours post-transplant.

FIG. 17. RNA Sequence Data, Angiogenesis. RNA Sequence Data for BEL compared to NL related to genes involved in angiogenesis including both genes with FC>1 and those equal to or less than 1. Selected genes related to vascular development in the BEL were examined for level of one month post-transplant. The Fold increases of BEL over NL are listed as are the gene IDs, gene names and descriptions.

FIG. 18. RNA Sequence Data, Cell Lineage. RNA Sequence Data for BEL compared to NL related to cell lineage. Selected genes related to lung lineage, aec I, aec II or epithelial cell function, neuroendocrine, Clara cell and muscle cells were examined for level of expression in BEL and NL one month post-transplant. The Fold increases of BEL over NL are listed as are the gene IDs, gene names and descriptions.

FIG. 19. Evaluation of Tracheal Development. (A) AC tracheal scaffold (white arrow points to surface of scaffold). (B) Phase contrast image of scaffold immediately after installation of tracheal cells in FGF2-hydrogel (white arrow is scaffold). (C) Image of BEL pre-transplantation showing tracheal cells attached to scaffold. (D) Averaged values for N=5 replicates of cells from 5 pigs showing cell attachment using media alone, hydrogel alone (HYDR) or hydrogel+ FGF2 (HYDR+FGF2). Data were analyzed using ANOVA. *p<0.001. Both scaffold treatments increased cell attachment over use of media alone. Hydrogel+FGF2 increased cell attachment over use of hydrogel alone. (E-J) Representative images of tracheal development in BEL. (E) Image of trachea of pig survived for 2 weeks. (F) Tracheal cells still have not reformed cell-to-cell junctions at two weeks post-transplant. (G) Image of BEL trachea at 1 month post-transplant. White arrow indicates scaffold. (H) SEM of cell junction formation between cells in BEL trachea. (I and J) Cell junctions and cell-to-cell contacts were re-established by 1 month.

FIG. 20. BEL Tissue Development. (A and C) Post-transplant examination of DAPI stained controls and (B and D) Ki-67 (red nuclei) and DAPI (blue nuclei) stained sections. (E) Average number of cells and percent Ki67 positive cells in NL compared to BEL post-transplant. Data were analyzed using ANOVA. *p<0.005, **p<0.005, not significant, NS. Consistently more cells were found in NL versus BEL. Higher levels of cell proliferation as measured by Ki67 staining were seen in the BELs of animals survived for 2 weeks and 1 month. (F-T) H & E stained sections of BEL at different time points. (F-H) Pre-transplant, day 30 of bioreactor culture. (F) H & E stained section of BEL. (G) Control DAPI stained section. (H) PSP-C (red) and DAPI stained section of BEL. (I-K) H & E stained sections of BEL post-transplant. These images show the organization of tissue with development of bronchioles and alveolar spaces including bronchiole-epithelial lining in: (I-K) pig-2 survived for 10 hours, (L-N) pig-1, survived for 2 weeks, (O-Q) pig-4, survived for 1 month post-transplant and (R-T) pig-5 survived for 2 months post-transplant. (J, O, R) Non-aerated areas of BELs lacked defined tissue structure. Tissue development in (I, M, P, Q S and T) aerated areas of lungs was similar to that of normal lung for pigs-1, -4 and -5. Regions of distal lung appeared normal and (M, P, Q, R and S) bronchioles demonstrated normal epithelial cell morphology.

FIG. 21. Cell Phenotypes Present in BEL. Representative images from pig-4, 1 month post-transplant. (A) DAPI stained control and (B) section of bronchiole positive for CK-18 (red). (C) DAPI stained control and (D) CC10 (red) positive cells. (E) TEM of mucin positive cells in airway and (F and H) DAPI stained controls and (G) MUC-5a (red) positive cells and (I) MUC-I positive (red) cells). (J) DAPI stained control and (K) co-expression of lung progenitor cell markers Ck-5 (green) and P63 (red). Insert shows nuclear staining.

FIG. 22. Reconstitution of BEL Immune System. (A) Phenotypic profile of the MNL preparation installed into BEL on days 11 and 30 of culture for N=6 pigs. (B) For tracking purposes CFSE-labeled MNL were loaded into a subset of pigs prior to transplantation. Image shows CFSE labeled MNL prior to installation. (C) DAPI stained section of lymph node from NL. (D). Representative image of lymph nodes. Following transplantation, CFSE-labeled cells were found in the pre-laryngeal and pre-tracheal lymph nodes of pig-2 (survived for 10 hours). (E) No CFSE-labeled cells were seen in the NL post-transplant but CFSE-labeled cells were always found in the (F) BEL near the bronchioles (white arrows point to cells). (G) On day 30 of culture pre-transplantation, alveolar macrophages (am) (black arrows) quickly reestablish close contact with alveolar surfaces and could be found in BEL of all animals (H) post-transplantation (G and H) Black arrows point to am.

FIG. 23. Antibodies Used For Cell Phenotype Analysis. The abbreviation and description of the antigen recognized by each primary antibody, dilutions used, clone identifier (when appropriate), secondary antibody used and commercial source are listed for all primary and secondary antibodies used during histochemical analysis in this study.

FIG. 24. Antibodies Used For Flow Cytometry Analysis. The abbreviation and description of the antigen recognized by each primary antibody, dilutions used, clone identifier (when appropriate), secondary antibody used and commercial source are listed for all primary and secondary antibodies used for flow cytometry in this study.

FIG. 25. Microbiome Primers Used In This Study. Swine Lung MB primers used to examine the BEL microbiome. References for each primer pair are listed (62-70). Note: For *Heamophilus parasuis* the two separate targets were evaluated and resulting qPCR data was averaged.

FIG. 26. Antibodies used to examine cell phenotypes or VEGF-loaded MPs. Information for the primary antibodies including antibody description, animal source, and abbreviation of the antibody, dilution of antibody, clone, company and secondary antibody information are listed.

Figure 27:
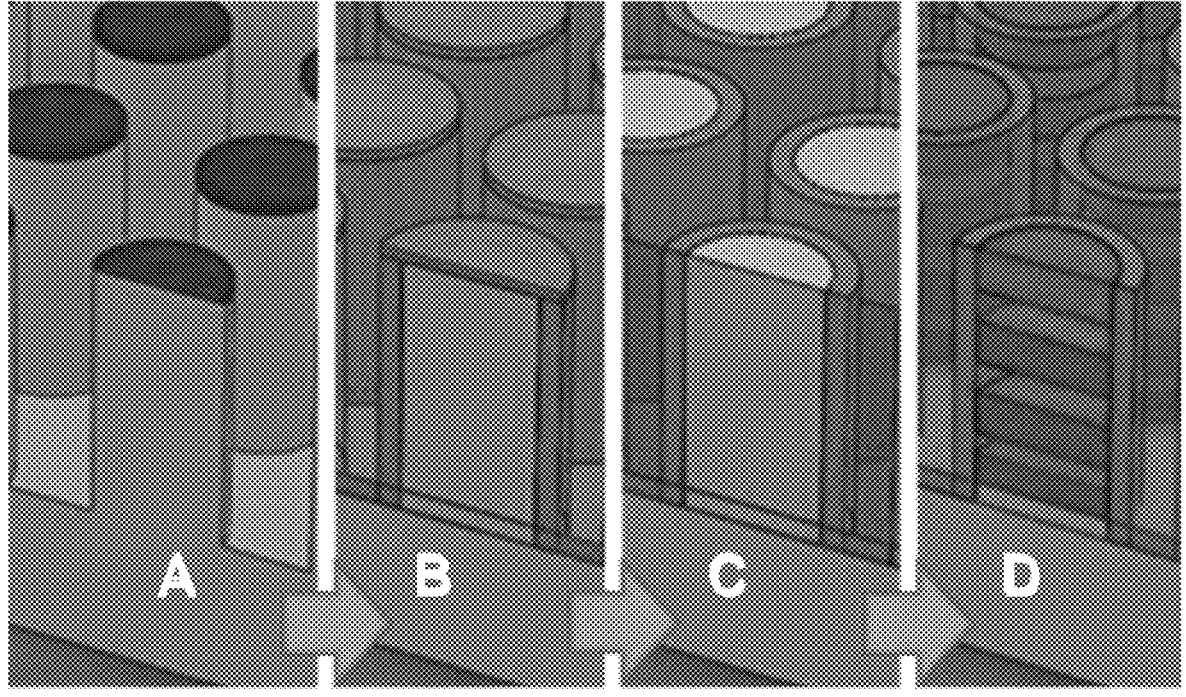

FIG. 27. Mesoporous Silicon MP Fabrication Process. (A) A one-step photolithography process is employed to define the particle geometry on a silicon wafer. A deep silicon etch is used to form uniform rows of silicon pillars. (B) The pillars are coated with a protective oxide to enable subsequent processes. (C) The top oxide layer of the coated silicon pillars is removed prior to the electrochemical etch process. (D) A programmed multi-cycled electrochemical etch provides uniform particle porosity and defined particle height.

FIG. 28. Preparation of Vascular Whole Lung Scaffolds. (A) Whole acellular lungs were cut into (B) right and left lung pieces. The trachea is indicated and the black arrow points to the pulmonary artery and vein which were stapled closed. Left trachea and lungs are used as whole lung scaffolds and right lungs are fine dissected to produce (C) small pieces of acellular vascular scaffold or (D) large pieces of scaffold were cut into (E) 2.5 cm segments. (F) Left lung scaffold showing cannulation of the trachea.

FIG. 29. VEGF Load Release. Load release of VEGF for 60 nm pore sized silicon MPs, 30 nm pore sized silicon MPs or a mixture of 60 & 30 nm pore sized MPs on 2.5 cm square segments of vascular scaffold. A mixture of 60 and 30 nm MP was used due to level of load release of VEGF alone.

FIG. 30. Vascular Cell Attachment. (A) 2.5 cm square pieces of acellular vascular scaffold were treated with VEGF-loaded 60 nm pore sized silicon MPs (60 nm MP), VEGF-loaded 30 nm pore sized silicon MPs (30 nm MP) or a combination of 60+30 nm pore sized MPs. (B) Primary porcine lung derived vascular cells from 5 pigs were added to five 2.5 cm$^2$ pieces of scaffold treated with VEGF-MP or MP without VEGF. (C-G) Representative H & E stained sections of scaffold pieces treated with (C) VEGF loaded 60 nm MP, (D) VEGF loaded 30 nm MP, (E) a mixture of 60 and 30 nm MP or (F) blank 60 and (G) blank 30 nm MP. (H) Average of cell attachment counts for five 2.5 cm$^2$ pieces of scaffold. Analysis of variance (Anova) was used to assess statistical significance in the comparison of [(MP-VEGF) to (MP No VEGF) and (60 nm) or 30 nm MP to (the mixture of 60 and 30 nm MP)] (p<0.05).

FIG. 31. IVIS Imaging of Cell Deposition in Vascular Scaffolds. (A) Vascular segments of whole acellular lung were removed from whole lung scaffolds. Light image showing pieces of vascular scaffold. (B) Deposition of VEGF loaded MPs labeled with anti-VEGF antibody (rainbow). (C) Examination of primary vascular cell attachment using CFSE labeled cells (red). MP dispersal scale on left and cell scale on right.

FIG. 32. Testing of Cell Deposition in Sections of Vascular Scaffolds. (A) Vascular segments of whole acellular lung are removed from whole lung scaffolds. (B and C) H & E images of cross sections of acellular blood vessels 100×. (D) Individual segments of acellular vascular scaffold can be filled with equal numbers of particles. (E) Gross image of particle filled vessels prior to incubation. (F) Fluorescent images of cross section of vessels after cell installation. Aggregates of degraded VEGF-MPs, stained with anti-VEGF antibody (red) were found throughout the vessel and were always in close proximity to CFSE tagged lung-derived vascular cells (green). DAPI nuclear stain (blue). White arrows indicate aggregates of VEGF-MPs.

FIG. 33. Whole Lung Scaffolds. (A) In this image a whole left lung scaffold is being placed in to the bioreactor chamber. The trachea, pulmonary artery and pulmonary vein have been cannulated. (B) A syringe was attached to the pulmonary artery port and cells were installed at a rate of 0.5 ml/min. (C) A diagram of the microfluidics system to support whole lung culture shows the directional flow of media from the trachea (pump 1) and the vascular system (pump 2). The port leading into the pulmonary artery was used to install VEGF MPs into the scaffold after suspending MPs in 200 ml of EGM with constant stirring.

FIG. 34. Delivery of MPs in Whole Lung Scaffolds. (A) IVIS image of left lung scaffold containing rhodamine red labeled MPs after 30 minutes or (B) 120 minutes of MP installation at 0.5 ml/min in EGF. Good dispersal of MPs throughout the lung was realized after 120 minutes of pump time. (C) CT scan of whole bioengineered lung showing vascular extracellular matrix and region removed and shown in (D and E). (black arrow shows vascular tree of scaffold) (D) VEGF-MP in small blood vessel of whole lung scaffold containing VEGF-MPs. Note VEGF staining MP (green) were only seen inside of the vascular scaffold and growth factor was not found outside of this area. (white arrow points to MP). (E) Phase contrast image of MPs in small capillaries in the whole lung scaffold. (F) Image of native pig lung stained for the presence of CD31+ endothelial cells (green) and (G) image of section of whole lung scaffold stained for the presence of VEGF loaded MPs (green) indicating that MPS were well dispersed throughout vascular areas of the scaffold. White arrows indicate large vessels with particles attached to cell wall.

FIG. 35. Development of Vascular Tissue in Whole Lung Scaffolds. Whole lungs were cultured and small sections of the whole organ were removed to examine cell dispersal and attachment on (A and B) day 5 and (C-F) day 10 of culture. (A) TEM of MP present in small vessel after 5 days of culture. (B) VEGF+ MPs in small vessel were always surrounded by cells as indicated by the presence of DAPI positive nuclei. (C) Longitudinal section of vessel showing aggregates of VEGF+ micro particles (red) and CD31+ endothelial cells (green). DAPI stained nuclei are blue. (C-F) After 10 days of culture, vessels were well formed, cells had attached to walls of vascular scaffold, VEGF positive regions (red) were still present and CD31+ endothelial cells were found lining the vessels. (F) TEM of the small capillaries shows capillary in in vitro cultured lung.

DETAILED DESCRIPTION OF THE INVENTION

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

Abbreviations used in this application:
AC—Acellular
ACE—Angiotensin Converting Enzyme
ACTA1—Skeletal Muscle Actin
ACTA2—Smooth Muscle Actin
ACTB—Encodes Actin Proteases
ACTG2—Actin, Gamma 2, Smooth Muscle, Enteric
AEC—airway epithelial cell
AGER—Advanced Glycosylation End-Product Specific
  Receptor
Ao—aorta
AQP5—Aquaporin-1
BAL—Bronchioalveolar lavage
BEL—Bioengineered lung
Beta-Catenin (CTNNB1)—Catenin Beta 1
CAV-1—Caveolin 1
CC10—Clara cell protein 10
CFSE—carboxyfluorescein succinimidylester
CHGA—Chromogranin A
Ck—pan-cytokeratin
CK5 (KRT5)—Keratin 5
CT—computed tomography
CXCR4—C-X-X Motif Chemokine Receptor 4
ECM—extracellular matrix
EGM—endothelial growth medium
EM—electron microscopy
ENO2—Enolase 2
Ep-CAM—epithelial cell adhesion molecule
ERG—early growth response protein
ETS1—ETS proto-oncogene 1, transcription factor
ETV2—ETS Variant 2
FC—fold changes
FGF2—fibroblast growth factor 2
FGFR1—Fibroblast Growth Factor Receptor 1
FSP-1—fibroblast specific protein 1
GF—growth factor
HEY1—Hes Related Family BHLT Transcription Factor
  with YRPW Motif 1
HEY2—Hes Related Family BHLT Transcription Factor
  with YRPW Motif 2
HEY L—Hes Related Family BHLT Transcription Factor
  with YRPW Motif-Like
ICAM1—Intracellular Adhesion Molecule 1
IFNγ—Interferon Gamma
IL2—Interleukin 2
IL1B—Interleukin beta 1
IOLA—infectious organism lurking in airways
ITG2AB—Integrin Subunit 2 alpha b
IVIS—in vivo imaging system
KDR—Kinase Insert Domain Receptor
KGF—keratinocyte growth factor
KRT18—Keratin 18
KRT5—Keratin 5
LV—left ventricle
LYVE1—Lymphatic Vessel Endothelial Hyaluronan
  Receptor 1
MAPK14—Map Kinase 14
Ki67—Marker of Proliferation Ki-67
MNL—mononuclear leukocytes
MP—microparticle
MPM—multiphoton microscopy
MRI—magnetic resonance imaging
MSC—mesenchymal stem cell
MUC13, 15, 1—Mucin (13, 15, 1), Cell Surface Associ-
  ated
MUC20—Mucin 20, Cell Surface Associated
NGS—next generation sequencing NKX2-1 (TTF1)—NK2 Homeobox 1
NL—native lung
NOS1—Neuronal Nitric Oxide Synthase
NOS2—Inducible Nitric Oxide Synthase
NRP-1—Neuropilin 1
P63 (TP63)—Tumor Protein P63
Pa—pulmonary artery
PDGFC—Platelet Derived Growth Factor C
PDGFRA—Platelet Derived Growth Factor alpha
PECAM1—Platelet and Endothelial Adhesion Molecule
  1
PF-127—Pluronic hydrogel
PROX1—Prospero Homebox 1
PRP—platelet rich plasma
P-SPC—pro-surfactant protein c
PTB—primary tracheal bronchial cells
Pv—pulmonary vein
PVASC—primary vascular cells
RAGE/AGER—Receptor for Advanced Glycation End
  Product
RBCs—red blood cells
RL—right lung
RV—right ventricle
SCGB3A2—Secretoglobin Family 3A Member 2
SCNN1G—Sodium Channel Epithelial 1 Gamma Subunit
SDF-1—Stromal Derived Factor 1
SDS—sodium dodecyl sulfate
SELE—Selectin E
SELP—Selectin P
SEM—scanning electron microscopy
SFTPC—Surfactant Protein C
SFTPB—Surfactant Protein B
SFTPD—Surfactant Protein D
SFTPA1—Surfactant Protein A1
SHH—Sonic Hedgehog
SMA—smooth muscle actin
SRY-Box 9—Sex-determining region 9 (SOX 9)
SRY-Box15—Sex-determining region 15 (SOX 15)
SRY-Box4—Sex-determining region 4 (SOX 4)
TEM—transmission electron microscope
TGFB2—Transforming Growth Factor Beta 2
TGFB1—Transforming Growth Factor Beta 1
TP63—Tumor Protein P63
TUNEL—Terminal Deoxynucleotidyl transferase dUTP
  nick end labeling
VCAM1—Vascular Cell Adhesion Molecule 1
VE-CAD—vascular endothelial cadherin
VEGF—vascular endothelial growth factor D
VEGFC—Vascular endothelium growth factor C
Wnt10B—WNT family member 10B As used herein, the term "subject" or "patient" or "trans-
plant recipient" refers to any recipient of the bioengineered
lung described herein.

The term "lung disease" or "pulmonary disease" as used
herein refers to a disease, disorder or condition that affects
the structure and/or function of the lung. Examples of lung
diseases include, but are not limited to, pulmonary paren-
chymal disease, diffuse parenchymal lung disease, intersti-
tial lung disease, pulmonary vascular disease, cystic fibrosis,
surfactant dysfunction disorders, pulmonary hypertension,
and other pulmonary anatomical defects or disorders, idio-
pathic pulmonary fibrosis (IPF), acute lung injury (ALI), and
chemotherapy, drug or radiation-induced fibrosis in the lung.

The present invention provides a method for making a
bioengineered lung (BEL) on an acellular (AC) lung scaf-
fold. In certain embodiments the process comprises seeding
progenitor lung cells onto or into the AC lung scaffold, then culturing the seeded scaffold in vitro in a bioreactor under conditions (e.g., appropriate growth factors, platelet rich plasma or serum) effective to induce differentiation and growth of the cells toward a lung lineage within the scaffold thereby producing a functional BEL that also includes vascular tissues which upon transplantation into a suitable recipient needed to maintain a healthy organ with full functionality.

In one aspect of these embodiments the AC lung scaffold can be prepared by decellularizing an adult or pediatric lung or lungs, preferably a mammalian lung, preferably that of a large mammal such as a pig, sheep, goat or other bovine or ungulate or a human or non-human primate. In preferred embodiments the native lung tissue comprises mammalian trachea and lungs preferably that of a large mammal such as a pig, sheep, goat or other bovine or ungulate or a human or non-human primate.

The decellularization process generally comprises a combination of physical, mechanical and enzymatic processes to cause cellular damage with subsequent removal of cellular debris. In certain embodiments the process comprises alternating cycles of rapid freezing and rapid thawing of native lung tissue and/or sonicating the native lung tissue to damage cells comprising the native lung tissue. The step of removing cellular debris can comprise contacting the lung tissue with a detergent and/or with peracetic acid within a continuously rotating bioreactor, to continuously circulate and contact the damaged tissue to effect removal of cells, damaged cells, including nuclei and nuclear material, and other cellular debris. In this aspect the detergent can be about 1-2% SDS continually circulated within the rotating bioreactor for about 5 weeks. The step of removing cellular debris can comprise treating any remaining damaged or intact cells with DNAase and RNAase to effect removal of any remaining nuclear material. Methods for preparing AC lung scaffolds have been previously described in (1) and (14) and in US Patent Application Publication No. 2011/0045045.

In certain embodiments a dextrose or other osmolyte or another treatment step can be effected prior to and/or during decellularization of the lung tissues in order to better preserve the integrity of the lung cells during decellularization of lung tissues. For example, harvested lungs can be washed with a dextrose solution, e.g., a 0.2% dextrose solution, e.g., for approximately 4 days.

In some embodiments, preparation of the BEL comprises recellularizing an AC lung scaffold with lung progenitor cells or primary lung cells, e.g., human or porcine progenitor cells or primary human or porcine lung cells. Primary human lung cells, including primary lung vascular cells and primary tracheal/bronchial cells, can be isolated from discarded human lungs or potentially may be derived from embryonic or adult human stem cells. Alternatively, the primary human lung cells can be autologous cells (i.e. cells from the intended transplant recipient) provided by a lung pneumonectomy done prior to transplantation of the BEL or allogeneic cells derived from an HLA-matched donor such as from a close family member. In certain embodiments, the primary lung cells can be introduced through the pulmonary artery, the pulmonary vein, and/or the trachea of the scaffold. Methods for obtaining primary human lung cells, and installing the cells in the AC lung scaffold, have also been previously described in (1) and (14) and in US Patent Application Publication No. 2011/0045045 which references are incorporated by reference in their entireties herein.

In some embodiments, harvested lungs can be flushed with an antibiotic solution. In some embodiments, pieces of distal lung can be excised avoiding bronchioles and bronchi, and minced into about 1-mm3 fragments then treated with a collagenase solution (e.g. 1 mg/ml collagenase). The resultant disassociated lung cells can be filtered and the filtrate centrifuged to collect the primary lung cells which can then be in maintained in a suitable medium until they are later used to cellularize AC scaffolds. In some embodiments, primary vascular lung cells may be isolated from blood vessels dissected from whole lungs, endothelial linings of the vessels scraped, and the resulting sheets of tissue finely minced then treated with collagenase. The resultant disassociated cells can then be cultured in an endothelial growth medium or frozen until they are later used to cellularize AC scaffolds.

In some embodiments prior to installation of the primary human lung cells, the AC lung scaffolds are sterilized. Suitable sterilization protocols include washing with a hydrogen peroxide solution (e.g. 0.05% $H_2O_2$) followed by ethanol treatment (e.g. 70% ethanol) and treatment with one or more antibiotics.

In some embodiments, the AC lung scaffolds are pretreated with platelet rich plasma before installation of the primary lung cells. Alternatively, or in addition, the AC lung scaffolds can be pretreated with growth factors, e.g., comprised in porous microparticles or nanoparticles and/or comprised in hydrogels.

Suitable growth factors may include by way of example one or more of the following: Adrenomedullin (AM), Angiopoietin (Ang), Autocrine motility factor, Bone morphogenetic proteins (BMPs), Ciliary neurotrophic factor (CNTF), Leukemia inhibitory factor (LIF), Interleukin-6 (IL-6), Colony-stimulating factor (CSF) (such as Macrophage colony-stimulating factor (m-CSF), Granulocyte colony-stimulating factor (G-CSF), and Granulocyte macrophage colony-stimulating factor (GM-CSF)), Epidermal growth factor (EGF), Ephrins (such as Ephrin A1, Ephrin A2, Ephrin A3, Ephrin A4, Ephrin A5, Ephrin B1, Ephrin B2, Ephrin B3), Erythropoietin (EPO), Fibroblast growth factor (FGF) (such as Fibroblast growth factors 1-23), Foetal Bovine Somatotrophin (FBS), GDNF family of ligands, Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factors (such as Insulin-like growth factor-1 (IGF-1) and Insulin-like growth factor-2 (IGF-2)), Interleukins (IL) (such as Interleukins 1-16), Cofactor for IL-3 and IL-6, Keratinocyte growth factor (KGF), Migration-stimulating factor (MSF), Macrophage-stimulating protein (MSP) (also known as hepatocyte growth factor-like protein (HGFLP)), Myostatin (GDF-8), Neuregulins (NRG) (such as Neuregulins 1-4), Neurotrophins (NT) (such as Brain-derived neurotrophic factor (BDNF)), Nerve growth factor (NGF), and Neurotrophins 3 and 4), Placental growth factor (PGF), Platelet-derived growth factor (PDGF), Renalase (RNLS), Anti-apoptotic survival factors, T-cell growth factor (TCGF), Thrombopoietin (TPO), Transforming growth factors (such as Transforming growth factor alpha (TGF-α), Transforming growth factor beta (TGF-β), Tumor necrosis factor-alpha (TNF-α), Vascular endothelial growth factor (VEGF), and Wnt Signaling Pathway. In a preferred embodiment, the growth factors are one or more of VEGF, FGF2, and KGF, preferably comprised in porous nanoparticles or microparticles or hydrogels which promote cell attachment, vascularization and tissue development.

Any one or more of the platelet rich plasma and the various growth factors can be added to the AC lung scaffolds using a controlled release delivery system. Suitable controlled release delivery systems include carriers such as disks, microparticles, nanoparticles, and pellets in which the drug is encapsulated and released at controlled rates for relatively long periods of time. Silicon particles for drug delivery are known in the art, and include biodegradable and/or porous silicon microparticles and nanoparticles. Use of particles with different pore sizes (e.g. the non-spherical particles with 30 and 60 nm pores described in (20) or described herein (see Example 3 and FIG. 27)) can provide a staged release of drugs such as growth factors. Polymeric materials for particle-based drug delivery are also known in the art and include cellulose derivatives, polymeric matrices (e.g. poly(ethylene oxide) (PEO) matrices), block copolymers (e.g. PEO-PPO-PEO), and organic-inorganic hybrid materials.

In certain embodiments any one or more of the platelet rich plasma and the various growth factors can be added to the AC lung scaffolds using a mixture of 30 and 60 nm pore sized microparticles or nanoparticles, e.g. non-spherical microparticles or nanoparticles such as discoidal porous silicon MPs. The mixture can be at any ratio of 30 to 60 nm pore sized MPs, such as a ratio in the range of 100:1 to 1:100, 50:1 to 1:50, 25:1 to 1:25, 15:1 to 1:15, 10:1 to 1:10, 5:1 to 1:5, 4:1 to 1:4, 3:1 to 1:3, 2:1 to 1:2, or 1.5:1 to 1:1.5 (e.g. 10:1, 9:1, 8:1, 7:1, 6:1, 5:1, 4:1, 3:1 2:1, 1:1, 1:2, 1:3, 1:4, 1:5, 1:6, 1:7, 1:8, 1:9, or 1:10). Optionally the ratio of 30 to 60 nm pore sized MPs is in the range of 2:1 to 1:2 (e.g. 1:1) and the MPs are used to deliver VEGF to the AC lung scaffold.

Hydrogels for drug delivery are also known in the art and include homopolymer hydrogels, copolymer hydrogels, multipolymer hydrogels, network hydrogels, anionic hydrogels, cationic hydrogels, neutral hydrogels, ampholytic hydrogels, amorphous hydrogels, semi crystalline hydrogels, hydrogen bonded hydrogels, biodegradable hydrogels (e.g. hydrogels comprising polymers such as poly (lactic-glycolic acid), polyethylene glycol-polylactic acid, glycolic acid-polyethylene glycerol (PEG-PLGA-PEG), poly (lactide-co-glycolide) (PLGA), hydroxyethyl cellulose (HEC), carboxymethyl cellulose, chitosan, chitosan crosslinked by HEC-Glyoxal, and starch (e.g. amylase and amylopectin)) and nanocomposite hydrogels (e.g. PEG, silicate-PEG nanocomposite hydrogels). Preferred hydrogels comprise natural and/or synthetic materials that mimic natural stem cell microenvironments, such as amphiphilic hydrogels. Suitable amphiphilic hydrogels include hydrogels made of amphiphilic copolymers, such as PLURONIC® F-127 (poloxamer 407)) which comprises ethylene oxide (PEO) and polypropylene oxide (PPO).

In some embodiments, the AC lung scaffolds are pretreated with VEGF microparticles and/or FGF2-loaded hydrogels. In some embodiments, pretreatment of the AC lung scaffolds comprises a combination of microparticle delivery of VEGF with hydrogel delivery of platelet-rich plasma, FGF2 and KGF. In some embodiments the VEGF, optionally in the form of VEGF-loaded microparticles, is delivered to vascular portions of the AC lung scaffold. VEGF-loaded microparticles can be delivered to the scaffolds by pumping the microparticles (optionally dispersed in a growth medium such as EGM) through the pulmonary artery of the scaffold.

In some embodiments, the VEGF microparticles and/or FGF2-hydrogel can be introduced into the AC lung scaffold via the pulmonary artery of the scaffold, optionally about 1-4 hours, e.g. about 2 hours before primary vascular cell installation. The KGF-hydrogel can be introduced into the AC lung scaffold via the trachea, optionally about 1-4 hours, e.g. about 2 hours, before primary lung cell installation.

In some embodiments, immune cells can further be introduced onto the AC scaffold, e.g., autologous or allogeneic immune cells in order to produce a BEL with a reconstituted immune system. In some embodiments, immune cells introduced onto the AC scaffold may include one or more of mesenchymal stem cells, macrophages (including M1 macrophages, M2 macrophages and unpolarized macrophages), mononuclear leucocytes and lipopolysaccharides, and culture supernatants from these cell types, can be introduced into the AC lung scaffold to support tissue development. In some embodiments, the scaffold is treated with mesenchymal stem cell culture supernatant, MSC cells, M2 culture supernatant, and/or M2 cells. In some embodiments the supernatants and cells may be added to the primary lung cells before the lung cells are seeded onto the AC lung scaffold.

In some embodiments the AC lung scaffold seeded with primary lung cells is cultured in a bioreactor to create functional three-dimensional lung tissue in the BEL. A bioreactor can maintain a relatively constant temperature, permit easy delivery of nutrients and growth factors to promote proper lung development, and eliminate any bio-products thereby minimizing cellular stress. About 30 days of bioreactor culture generally allows the cells installed in the AC lung scaffold to proliferate and initiate tissue development prior to implantation in a recipient subject. Bioreactors are commercially available and well-known in the art, and are also described in in (1) and (14) and in US Patent Application Publication No. 2011/0045045.

In some embodiments, the immune system in the BEL is reconstituted by installing mononuclear leukocytes into the BEL at about day 5-20 (e.g. day 5, 6, 7, 8, 9, 10, 11, 12, 13, 14, 15, 16, 17, 18, 19 or 20) of bioreactor culture and/or at about day 20-40 (e.g. day 20, 21, 22, 23, 24, 25, 26, 27, 28, 29, 30, 31, 32, 33, 34, 35, 36, 37, 38, 39 or 40) of bioreactor culture, prior to transplantation of the BEL into a transplant recipient. Serum and/or alveolar macrophages can also be installed into the BEL instead of or in addition to the mononuclear leukocytes. The mononuclear leukocytes can include any one or more of T-lymphocytes (CD4 and CD8), macrophages, and B-lymphocytes (e.g. IgG-positive B-lymphocytes). Preferably, mononuclear leukocytes are installed into the BEL at about day 11 and 30 of culture. The mononuclear leukocytes and other immune components may be autologous or allogeneic cells, e.g., cells obtained from an autologous or allogeneic human donor.

The present invention also provides a BEL suitable for clinical use, such as transplantation, produced by a method described herein. In this embodiment the BEL may be transplanted into a subject who may need a lung transplant. In this context the BEL which is to be transplanted means any BEL tissue which is to be transplanted into a transplant recipient and includes a portion of a lung, a single lung or a pair of lungs. Such subject or transplant recipient may be an adult or a child having a pulmonary disease, a pulmonary disorder or an injury or damage to pulmonary tissue. Examples include pulmonary parenchymal disease, diffuse parenchymal lung disease, interstitial lung disease, pulmonary vascular disease, cystic fibrosis, surfactant dysfunction disorders, pulmonary hypertension, and other pulmonary anatomical defects or disorders.

In yet another embodiment the invention provides a method for transplanting a BEL produced by a method described herein into a subject in need thereof. Because the methods for producing BEL described herein promote systemic vessel or vascular development, in certain embodiments the BEL can be transplanted into a recipient without creation of a pulmonary artery anastomosis.

The invention also provides a method for reconstituting the lung microbiome in a BEL. The specific lung microbiome can be determined by assessing the microbiome of different regions of the lung in a normal lung as compared to a BEL post-transplantation. This information can be used to reconstitute the microbiome in a BEL. Transplanting a BEL having a reconstituted microbiome may improve tissue formation and remodeling.

The following examples are given for the purpose of illustrating various embodiments of the invention and are not meant to limit the present invention in any fashion. One skilled in the art will readily appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1

Introduction

Advances in the production of bioengineered lung (BEL) (1-4) have not been matched in the development of functional vascular tissue (5-9). Whole BEL produced on acellular (AC) lung scaffolds have been transplanted in small animal models, but lungs failed due to intravascular coagulation and defects in endothelial barrier function leading to pulmonary edema (2, 3, 9). No approach has allowed for long-term survival of BEL following transplantation.

The lung is unique because it contains both a pulmonary circulation and a systemic or bronchial circulation originating at the aorta (Ao) (11, 12). The bronchial circulation provides nutrients and oxygen to the lung parenchyma, pleura, airways and blood vessels while the pulmonary circulation is essential for gas exchange. Work examining passive diffusion of gas into the lung, suggests that non-vascularized lung can survive for periods of time without vascular support (10) or ligation of the pulmonary artery (Pa) (11, 12). In this study, we focused on development of the bronchial systemic circulation to support BEL growth and survival following transplantation. We performed a pilot study to establish feasibility of BEL transplantation, with an airway anastomosis, but without a vascular (pulmonary) anastomosis. We relied on development of collateral systemic circulation to support tissue survival (13). BELs were created for N=6 pigs, however 4 pigs received implanted BEL while 2 animals were euthanized, prior to receiving a BEL. The source of autologous cells was provided by a left lung pneumonectomy done 30 days prior to transplantation. Apart from enhancing our understanding of pulmonary vascular development in transplanted tissues, this approach allowed the unique opportunity to (1) initiate examination of the BEL transcriptome, (2) evaluate BEL tissue development post-transplant, (3) determine the BEL immune response, (4) evaluate acute and chronic rejection, and (5) examine reestablishment of the microbiome within the BEL.

Results

Decellularization

Figures 9A, 9P:
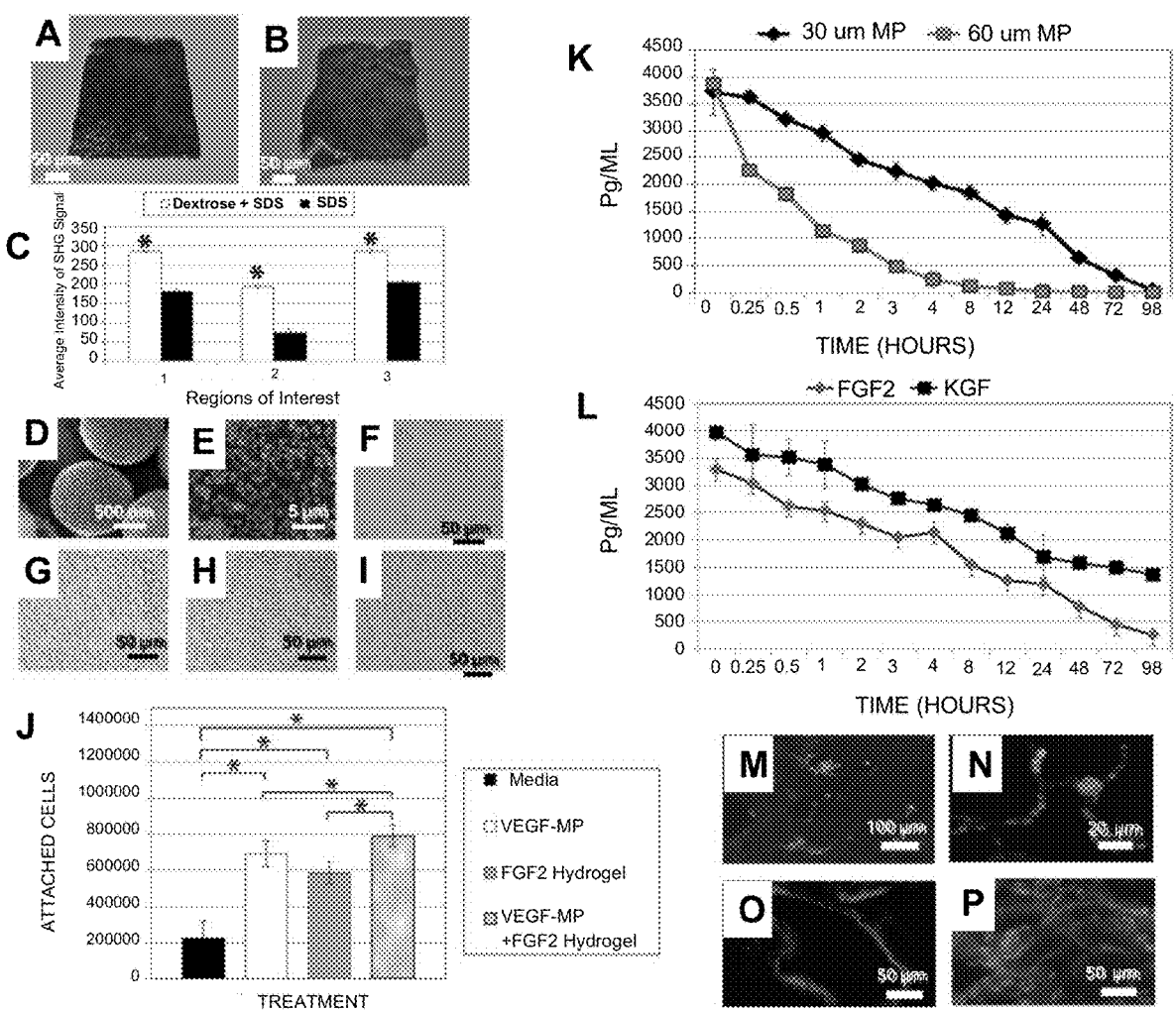

AC lung scaffolds were produced as described (1, 14) with one modification. A dextrose pretreatment step was added prior to decellularization of whole lungs. We hypothesized that the osmolyte dextrose would enhance protein stability (15, 16), reducing collagen loss following sodium dodecyl sulfate (SDS) decellularization. Established multiphoton microscopy (MPM) and second harmonic generation (SHG) methods (1, 14) indicated that collagen fibers were less damaged (FIG. 9A compared to FIG. 9B) and significantly more collagen was retained in scaffolds produced using dextrose-SDS decellularization (FIG. 9C).

Supplementation of Scaffold

In past studies, AC lung scaffolds were supplemented with platelet rich plasma (PRP)-loaded pluronic F-127 (PF-127) hydrogel (1, 14) prior to addition of cells. The ability of hydrogels or nanoparticles to target delivery and maximize growth factor (GF) release in support of vascular tissue development has been previously demonstrated (1, 17-19). We combined microparticle (MP) delivery of vascular endothelial growth factor (VEGF) with hydrogel delivery of PRP, fibroblast growth factor-2 (FGF2) and keratinocyte growth factor (KGF). Discoidal porous silicon MP (20) with 30 or 60 nm pores delivered VEGF to vascular portions of the scaffold. Images of 1 μm VEGF-MP show MP shape and structure (FIGS. 9D and 9E). Suitability of GF treatment was determined by measuring attachment of primary vascular cells (PVASC) to 3×3×0.5 cm pieces of AC vascular scaffold pretreated with media (FIG. 9F), VEGF-MP (FIG. 9G), a mixture of VEGF-MP and FGF2-hydrogel, (FIG. 9H) or FGF2-hydrogel (FIG. 9I). Use of VEGF-MP, FGF2-loaded hydrogel or VEGF-MP mixed with FGF2 hydrogel enhanced cell attachment (FIG. 9J) beyond media-hydrogel alone. VEGF-MP and FGF2 loaded hydrogel provided best cell attachment and was used in this study to enhance vascular cell attachment in scaffold vessels. Use of MP with different pore sizes provided for a staged release of VEGF (FIG. 9K), in scaffolds prior to cell installations. Hydrogel-loaded with FGF2 or KGF released GF at a steady rate over time (FIG. 9L). In whole lung scaffolds VEGF-MP (FIGS. 9M and 9N) and FGF2-hydrogel (FIG. 9O) delivered via Pa installation were consistently found within the small vessels and capillaries of the scaffold. Tracheal delivery of KGF-hydrogel was also used to support cell attachment in alveolar spaces (FIG. 9P).

Mesenchymal stem cells (MSCs) and macrophages have potential to support tissue development through production of paracrine factors. MSCs support angiogenesis (18, 21, 22) produce immunomodulatory factors (23), promote lung repair (24, 25), induce tolerance (26, 27) and regulate macrophage function (28). MSCs along with macrophages (29) and M2 macrophage subsets also contribute to tissue regeneration (29, 30). In order to study the effects of MSC and M2 cells on lung tissue development we added autologous MSCs, unpolarized macrophages, M1 or M2 macrophage subsets, mononuclear leucocytes (MNL)s or lipopolysaccharide (LPS) stimulated MNLs or culture supernatants from these cell types to primary lung cells (PL) seeded onto 3×3×0.5 cm pieces of AC lung scaffold. Attachment, viability and proliferation were measured after 7 days of in vitro culture. KGF-loaded hydrogel (50 ng/ml) was used as a positive control. Increased cell attachment (FIG. 10A) and increased proliferation, as measured by Ki67 cell staining, were found when PL were cultured on KGF-hydrogel pretreated scaffolds (FIG. 10B) or with addition of MSC supernatant, MSC, M2 cell supernatant or M2 cells to PL cultures justifying use of these supplements in the production of whole BEL.

Production of BEL for Transplantation

Procedures for re-cellularization of whole AC pediatric scaffolds (1) with adult lung-derived cells were modified for use in this study. Changes included installation of VEGF-MP and/or FGF2-hydrogel into the Pa of whole AC scaffolds 2 hours before PVASC installation and addition of KGF-hydrogel into the trachea of the scaffold 2 hours prior to PL installation.

The PL preparation, contained low numbers of aquaporin-5 (AQ5)+ aec I, high numbers of pro-surfactant protein C (P-SPC)+ aec II, low numbers of smooth muscle actin (SMA)+ cells or fibroblast specific protein (FSP-1)+ fibroblasts (FIG. 11A-I). Cells in the PVASC cell preparation contained CD31+ and vascular endothelial cadherin positive (VE-CAD+) cells with low numbers of SMA and FSP-1 positive cells (FIG. 11J-R). Primary tracheal-bronchial cells (PTB) were pan-cytokeratin positive (Ck+) Ck-18+, epithelial cell adhesion molecule positive (Ep-CAM+) cells with low levels of Clara cell protein-10 (CC10) or FSP-1 positive cells included (FIG. 11S-CC). PVASC were installed into the Pa of the lung scaffold and PL and PTB were installed into the trachea (FIG. 12). MSC sup, MSCs, M2 mac sup and M2 cells were added during BEL culture (FIGS. 12 and 13) based on in vitro testing (FIG. 10). The table in FIG. 13 lists the type and number of autologous cells installed into the scaffold. Under culture conditions, oxygen levels were relatively uniform for media alone or media and scaffold cultures over 30 days. For BEL cultures, there was a slow drop in oxygen levels over the 30-day culture period as oxygen was consumed by the cells of the BEL (FIG. 14). $PO_2$ level of the chamber dropped to 40.62 mmHg when the oxygenator was turned off and returned to not teal levels once the oxygenator was turned back on. In a subset of scaffolds, carboxyfluorescein succinimidyl ester (CFSE)-labeled PL cells were installed into scaffolds and Spectrum in vivo imaging system (IVIS) was used to examine cell dispersal on small pieces of AC scaffold (FIGS. 15A and B) or whole lungs (FIG. 15C-F). CFSE-labeled MNL or PVASC also allowed evaluation of cell dispersal or tracking of selected cell types. An overview of BEL production is shown in FIG. 1A-I. The right lung (RL) was removed (FIG. 1A) to produce a left lung scaffold (FIG. 1B). The Pa, pulmonary vein (Pv) and trachea of the scaffold were cannulated as described (1) prior to placement in the bioreactor (FIGS. 1B and C). A diagram of the fluidics system, pumps and bioreactor is shown in FIG. 1D and in image 1E. On day 30 of bioreactor culture BEL (FIG. 1F) were harvested and samples were removed for genomic, EM, histology and microbiome analysis (FIG. 1G) before transfer to the surgical suite (FIG. 1H) for transplantation (FIG. 1I). Bronchoscopy was done of all BELs pre-transplant (S Video 1). Native lung (NL) controls were isolated from the left lung following the pneumonectomy. During transplantation, BELs immediately expanded once the trachea-to-tracheal anastomosis was made (FIG. 1I).

Transplantation and Outcomes

Figures 2A, 2N:
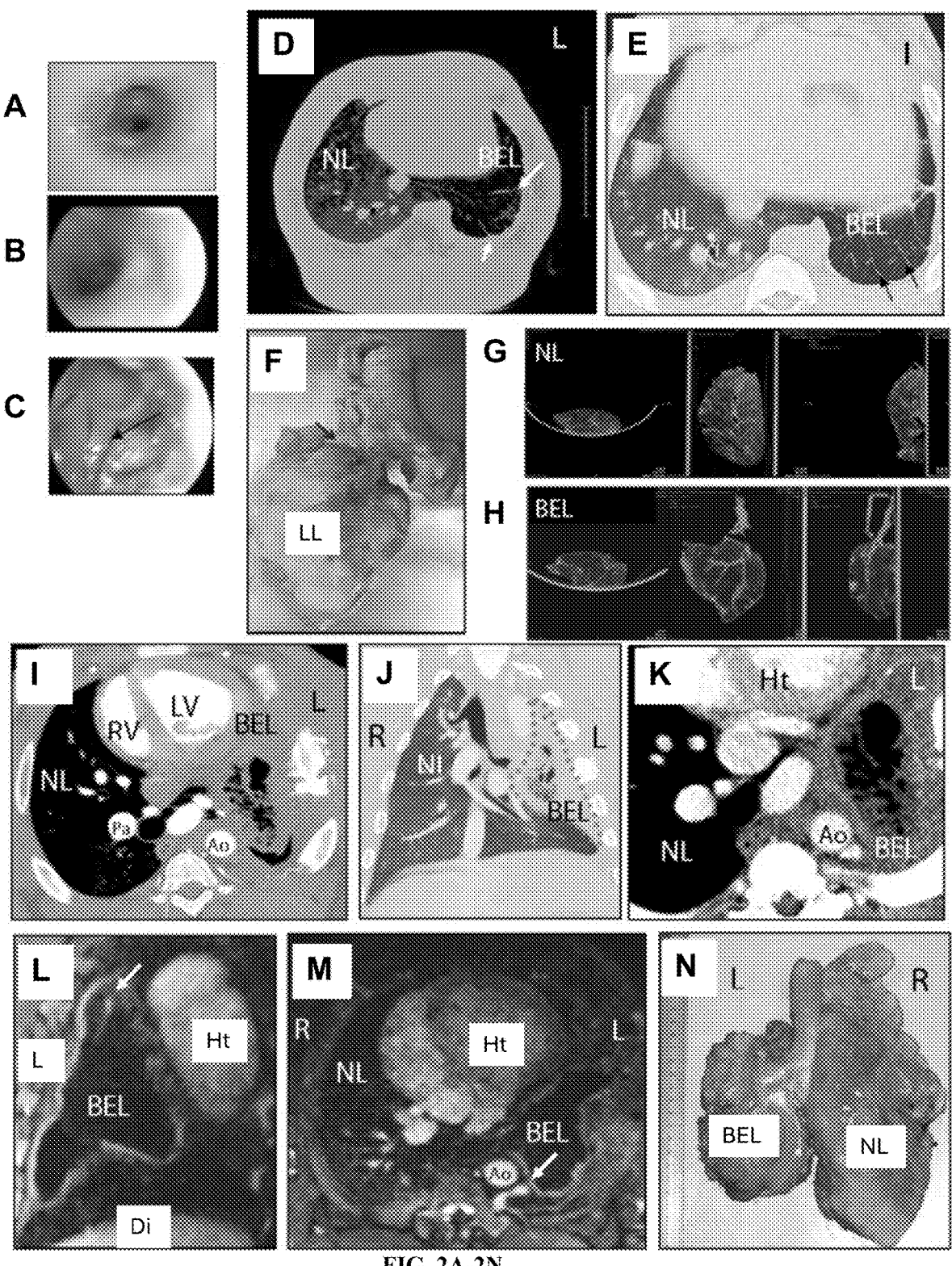
FIG. 2. Gross Assessment of Bioengineered Lung and Native Lung. (A-C) Representative bronchoscopy images of (A) BEL pre-transplant and (B) area above the anastomosis site showing left main stem bronchus and (C) BEL trachea-to-trachea anastomosis (black arrow). (D and E) CT angiograms of the thorax of pig-1, 2 weeks post-transplant. (D) Collateral circulation in BEL is highlighted (white arrows) and aerated regions appear black in this colorized image. (E) Collateral vessels formed in BEL post-transplantation (black arrows). (F) Gross image of BEL from pig-1, post-transplant. Left lung (LL) is shown. Black arrow indicates anastomosis site. (G and H) Micro CTs of open airway in non-ventilated (G) NL and (H) BEL of pig-1. (I-N) BEL of pig-4, I-month post-transplant. (I) CT angiogram of the thorax in the arterial phase, axial image showing BEL in the left thoracic cavity (red dots denote edges of BEL). (J) Coronal image shows BEL in the left hemi-thorax. (red dots denote edges of BEL). (K) Axial CT image of both NL and BEL. This close up image of BEL highlights aerated and compressed regions of the lung. (L) Coronal and (M) axial images of MRI angiography shows peripheral enhancement outlining the left BEL indicating capillary vascularization. A large vessel is seen crossing the upper portion of the lung on coronal image (white arrow). Coronal MRI image showing full expansion of both right NL and left BEL. Arrow points to large collateral vessel in BEL. (N) Gross image of the BEL post-necropsy showing right lung (R) and the smaller bioengineered left lung (L).

Six non-immunosuppressed pigs were used (FIG. 16A) with 2 pigs euthanized prior to BEL transplantation due to surgical complications (Sc) related to the left lung pneumonectomy. Four animals received left autologous BELs and were euthanized at 10 hours (pig-2), 2 weeks (pig-1), 1 month (pig-4) and 2 months (pig-5) (FIG. 16A) post-transplantation. Following surgery pig-5 developed an airway occlusion, reducing lung expansion. Pulse oximetry remained at 100% throughout the testing period. All pulmonary function measurement showed a trend towards return to baseline values suggesting that transplanted lungs had normal pressures and volumes (FIG. 16B-D). Bronchoscopy was performed pre- (FIG. 2A and Video 2) and post-transplant (FIG. 2B, C and Video 3). Small blood vessels were seen mid-trachea and at the anastomosis site (FIGS. 2B and C) in animals survived for longer than 10 hours. A computed tomography (CT) angiogram of the thorax of pig-1 (survived 2 weeks) compares the BEL and NL in a colorized CT image (FIG. 2D) and CT image (FIG. 2E). Development of collateral blood circulation in BEL was established by 2 weeks post-transplant (FIGS. 2D and E). FIG. 2F is a gross image of the BEL. Micro CTs of NL and BEL demonstrated that BEL contained open airways and that tissue density was comparable (FIG. 2G compared to 2H). In pig-4 (survived 1 month), a CT angiogram of the thorax in the arterial phase, axial image, shows aerated portions of the BEL in the left thoracic cavity. The Ao, Pa, right (RV) and left (LV) ventricles are noted (FIG. 2I). A coronal image of this animal shows the BEL in the left hemi-thorax (FIG. 2J). Hyperinflation of the right lung resulted in herniation of the NL into the inferior left hemi-thorax. This contributed to the restricted expansion of the BEL (FIG. 2J) although the left lung became aerated during breathing (FIG. 2K). Coronal and axial images of magnetic resonance imaging (MRI) angiography display the peripheral enhancement outlining the left BEL due to capillary re-vascularization (FIGS. 2L and M). A large intercostal vessel arising from the aorta with branches extending toward BEL is noted on the axial image (FIG. 2M, arrow). The gross image of the BEL from pig-4, post-necropsy shows the smaller size of the left BEL compared to the right NL (FIG. 2N).

BEL Transcriptome Profile

We initiated the examination of BEL gene expression profiles at 1 month (pig-4) post-transplant in order to determine if angiogenesis or tissue development was still in progress and to identify key time points for examination of the BEL transcriptome in later studies. We tested 4,128 genes of BEL or NL samples isolated from the BEL of pig-4, that was survived for 1 month. Gene expression of NL was set to be reference, and fold changes (FC) of gene expression were calculated for BEL. For this study FC was defined as:

$$FC = \frac{(GE_{Engineered} + 1)}{(GE_{Native} + 1)}$$

Although there were variations in levels of gene expression in BEL compared to NL the types of genes expressed were similar (FIG. 3A). Compared with NL, an average of 11.79% of the genes were down-regulated (0<FC<=0.5) and 15.93% were up-regulated (FC>=2) in BEL (FIG. 3B). The majority (72.28%) of genes (0.5<FC<2) remained at the same expression level as NL (FIG. 3B). We performed a paired Student's t-test between BEL and NL gene expression with log 2 transformation. Genes with FC>=2 or FC<=0.5 (P value <=0.05) were defined as potential differentially expressed genes (FIG. 3A, B, C and FIGS. 17 and 18).

Angiogenesis related genes that were upregulated in the BEL at 1 month post-transplant included; MAPK14 (FC-5.00), TGFB2 (FC-5), PDGFC (FC=3), VCAM1 (FC=3), VEGFD (FC=3) HEY 1 (FC=2.5), SRY-Box-9 (SOX 9) (FC=3), PDGFRA (FC=2.5), SHH (FC=2.25), SRY-Box-15 (SOX-15)(FC=2), FGFR1 (FC=2), SELP (FC=2), Wnt10B (FC-2.00), ETV2 (FC=2) and ICAM1 (FC=2) (FIG. 3C). Other upregulated genes included KDR/VEGF2R (FC=1.55), CXCL12/SDF-1 (FC=1.33), NRP1 (FC=1.28), SRY-Box-4 (SOX-4) (FC=1.25) and CXCR4 (FC=1.17) (FIG. 3C) as well as ITG2AB/CD41, ETS1, TGFB1, HEY2, PROX1, VEGFC, PECAM1, NOS2, NOS1, SELE, (FIG.

17). In normal vascular development, one of the major signaling pathways is Notch (31). While there was increased expression of downstream Notch target ligands in the BEL, Hey1 (FC=3.00) and HeyL (FC=2.50), this expression was not as robust as would have been expected if production of the BEL were purely a developmental process (32). Genes expressed in BEL also included lung lineage genes NKX2-1 (FC=1.4) and aec I cell associated genes AQP5 (FC=2), SCNN1G (FC=2), CAV-1, RAGE/Ager or aec II associated genes SFTPC, SFTPB, SFTPD and SFTPA1 (FIG. 18). Other lung epithelial cell associated genes expressed in the BEL included KRT19, MUC20, MUC13, MUC15, TP63, MUC1 and KRT5 (FIG. 18). Genes normally expressed by neuroendocrine cells (CHGA, ENO2 and FOXF2), Clara Cells (SCGβ3A2) or muscle cells (ACTG2, ACTA1, ACTB, ACTA2) (FIG. 18) were also expressed.

The gene profile of BEL was similar to that of the NL although the BEL exhibited distinct expression profiles. Despite this study's limitations due to the small sample size, the information generated provides an important gene expression dataset to build from in the future.

BEL Vascular and Lymphatic Development

Figures 4A, 4W:
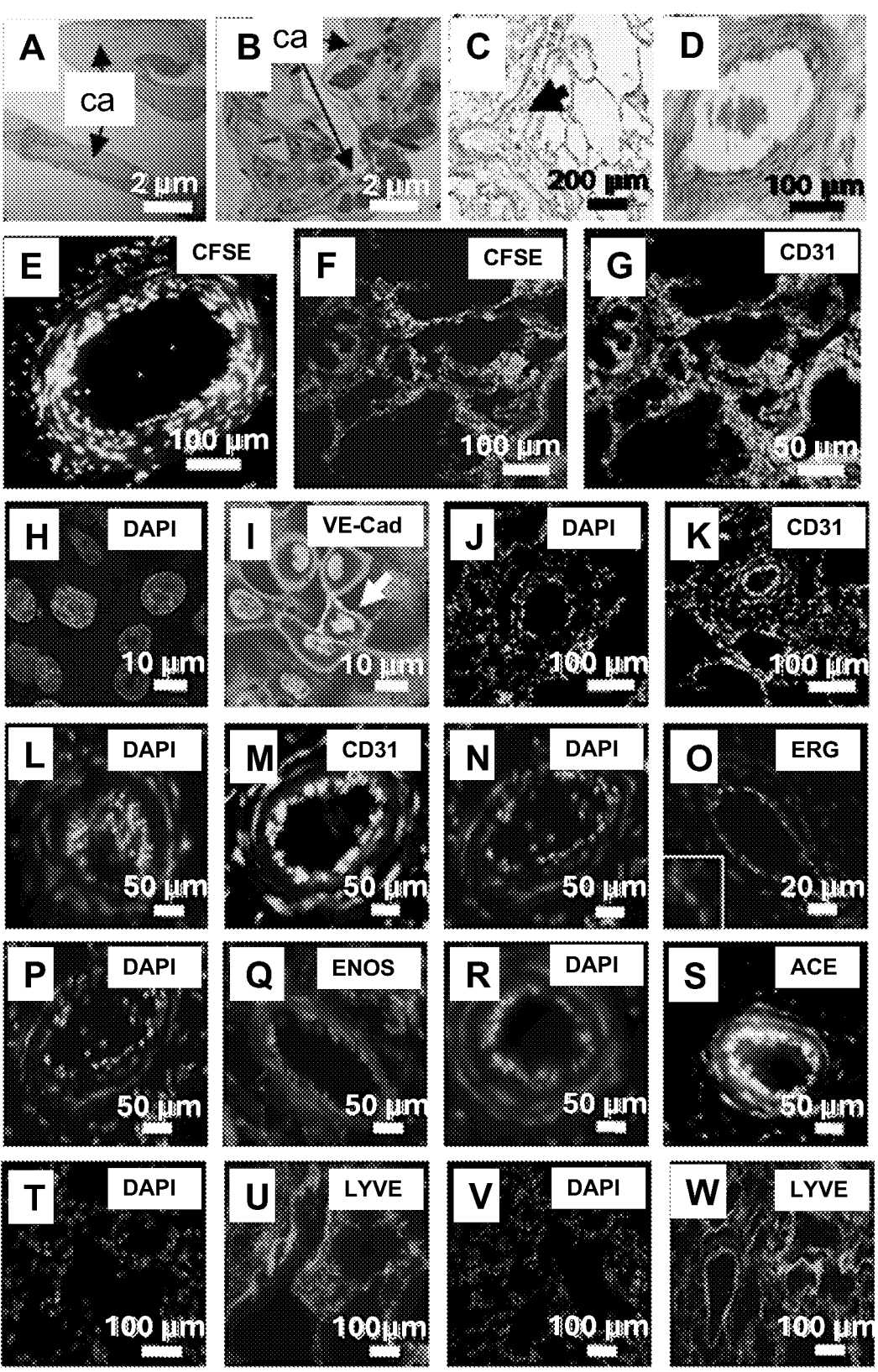
FIG. 4. Vascular Tissue Development in BELs. (A) TEM of BEL, pre-transplantation showing capillaries (ca) without rbcs (black arrow), day 30 of bioreactor culture. (B) Representative TEM of BEL at 2 weeks post-transplant, with rbc-filled collateral capillaries (ca) (black arrows). (C and D) H & E images of collateral blood vessels in BEL 2 weeks post-transplant. (C) Longitudinal section and (D) Cross section of an H&E stained collateral vessel. (E-W) BEL harvested 1-month post-transplant. (E) Cross section of CFSE-labeled (green) vessel in BEL. (F and G) Blood vessels within BEL formed from CFSE labeled (green)

Pre-transplant capillaries in BEL were well-developed but contained no red blood cells (FIG. 4A). Vessels were held open by the flow of media into the Pa and out the Pv. Post-transplantation collateral circulation developed in pig-1 within 2 weeks (FIG. 4B) and developed in all animals that survived 2 weeks or longer (FIG. 2E, L, M). BEL microvasculature appeared normal (FIGS. 4C and D) and based on CFSE labeling of PVASC cells, vessels in the BEL were formed from installed cells (FIGS. 4E and F). Prior to BEL harvest and pig's spontaneously breathing 21% oxygen the average partial pressure of oxygen (pO2) in the BEL Pa was 123±10 mmHg indicating it was receiving oxygenated blood and not venous blood from the collateral circulation. The lack of an oxygen gradient at the alveolus capillary junction prevented gas exchange as has been documented in past studies (11, 13). Vessels in BELs were positive for expression of CD31 (FIG. 4K, M; J, L are controls) and angiogenesis markers such as transcription factor early growth response protein-1 (ERG) (FIG. 4O, N control) and endothelium nitric oxide synthetase (eNOS) (FIG. 4Q, P is control). Vessels expressed vascular markers such as angiotensin converting enzyme (ACE) (FIG. 4S, R is control) that contribute to vascular muscle tone and blood flow (33, 34). ERG is also involved in regulation of endothelial homeostasis and vascular development (35, 36) as is eNOS and plays a role in VEGF mediated angiogenesis (37). Lymphatic vessel endothelial receptor-1 (LYVE) positive areas were seen at 1 month (FIG. 4U, T is control) and by 2 months post-transplant lymphatic vessels were found throughout the BEL (FIG. 4W, V control) near respiratory bronchioles. This suggests that there was reestablishment of pulmonary lymphatics that allow for support of essential immune responses and clearance of interstitial fluid.

BEL Tissue Development

Figures 5A, 5O:
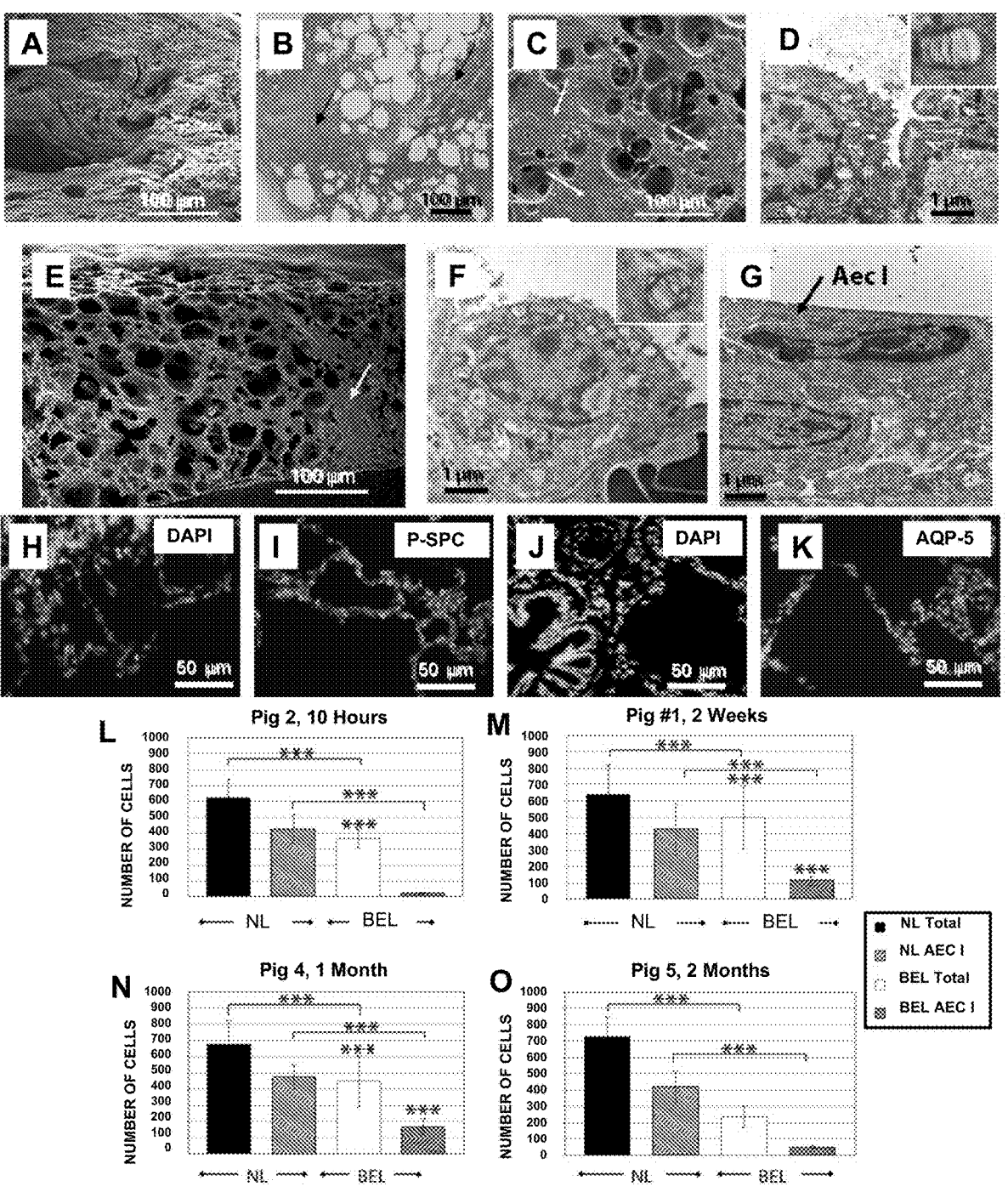

AC distal lung scaffold lacks structure or definition of alveolar spaces (FIG. 5A). Following recellularization on day 30 of bioreactor culture, the BEL was shown to contain well-developed alveolar areas (FIGS. 5B and C) although there were non-aerated regions of the BEL (FIG. 5C, arrows). Aec II (FIG. 5D) were the predominant cell type in BEL pre-transplant. Post-transplantation normal breathing enhanced aeration of the BEL although occasional areas of tissue compression were evident (FIG. 5E). Aec II (FIGS. 5F and I, H is control) and aec I were present in all animals (FIGS. 5G and K, J is control). The total number of cells increased in BEL in animals survived for two weeks (FIG. 5M), 1 month (FIG. 5N) and 2 months (FIG. 5O) compared to the animal that was survived for 10 hours post-transplant (FIG. 5L). The total number of aec I also increased in pigs survived 2 weeks and 1 month but not in pig-5, which experienced an occlusion (FIG. 5O) post-transplant, which reduced aeration and stretch of tissues.

Figures 19A, 19B, 19C, 19D, 19E, 19F, 19G, 19H, 19I, 19J:
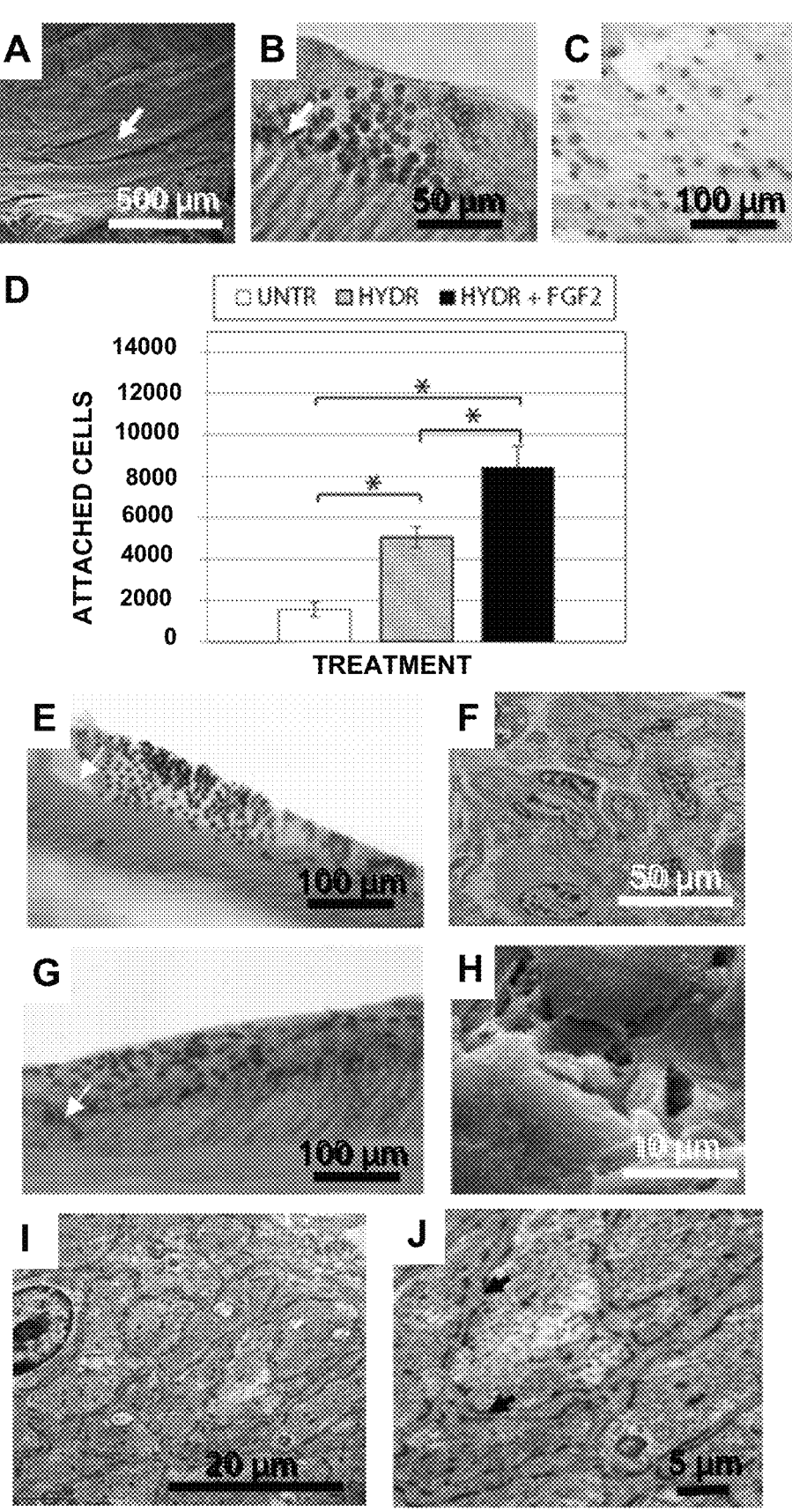

AC trachea scaffold (FIG. 19A) does not support cell attachment. We used FGF2-hydrogel to support tracheal cell installation and (FIGS. 19B and C). Data showed that FGF-hydrogel provided for better attachment to tracheal scaffolds than media or hydrogel alone (FIG. 19D). Two weeks post-transplant cells remained dispersed over the scaffold surface (FIGS. 19E and 19F) and lacked development of cell-to-cell contacts. By 2 months, cells in the BEL trachea were shown to have reestablished cell-cell contacts with development of inter-cellular junctions (FIG. 19G-J) in most areas.

Figures 20A, 20T:
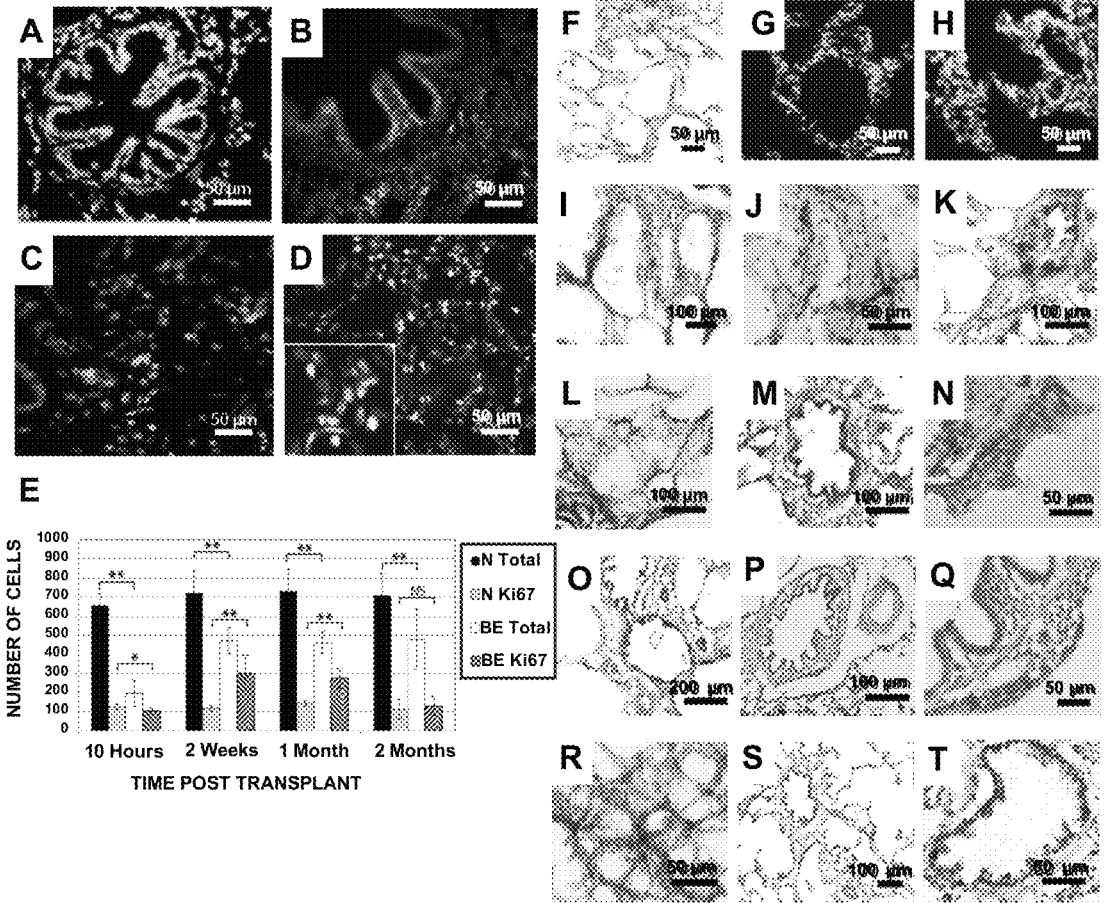

Representative images show the presence of Ki67 positive, proliferating cells, in bronchioles (FIG. 20B, A is control) and lung tissue (FIG. 20D, C is control) of all BELs. Higher levels of Ki67 were found in animals survived for 2 weeks and 1 month post-transplantation (FIG. 20E). Comparison of H & E stained sections of BEL indicated that pre-transplant tissues lacked definition of alveolar areas (FIG. 20F). Post-transplantation tissues continued to develop although alveoli and bronchioles (FIG. 20I-T) were poorly developed at 10-hours (FIG. 20I-K), or 2 weeks (FIG. 20L-N). In the BEL of animals survived 1-month (FIG. 20O-Q) or 2-months (FIG. 20R-T) alveoli and bronchi were indistinguishable from NL except within non-aerated regions of the lung in pig-5. Key changes in tissues following transplantation include continued angiogenesis within the BEL and development of the epithelial lining of the trachea, bronchi and bronchioles.

Figures 21A, 21B, 21C, 21D, 21E, 21F, 21G, 21H, 21I, 21J, 21K:
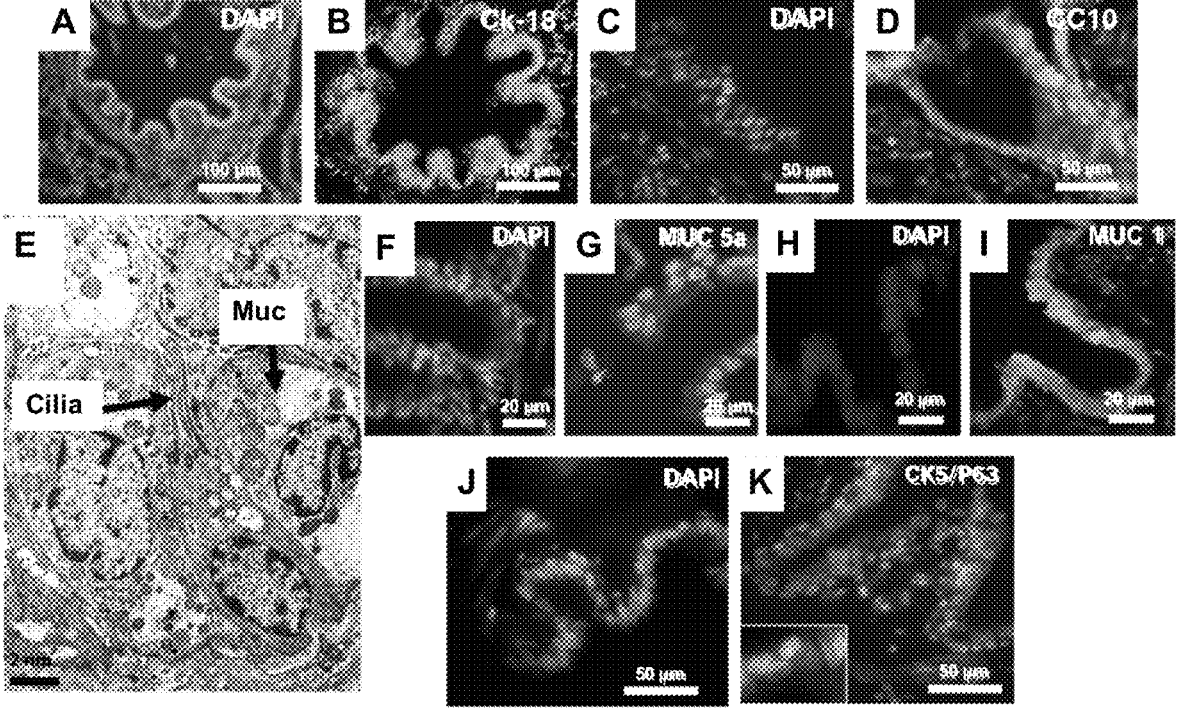

Ck-18+ cells were present in all developing bronchioles (FIG. 21B, A is control) as were CC10 positive Clara cells (FIG. 21D, C is control). Cells in the bronchioles produced mucin (FIG. 21E) and some cells produced mucin-5a (MUC-5a) a protein marker of developing airway epithelium (FIG. 21G, 21F is control) and Muc-1 (MUC 1) (FIG. 21I, 21H is control). Low levels of lung progenitor cell phenotypes such as CK5/P63 (38) were found in small bronchioles (FIG. 21K, 21J is control).

Figures 6A, 6O:
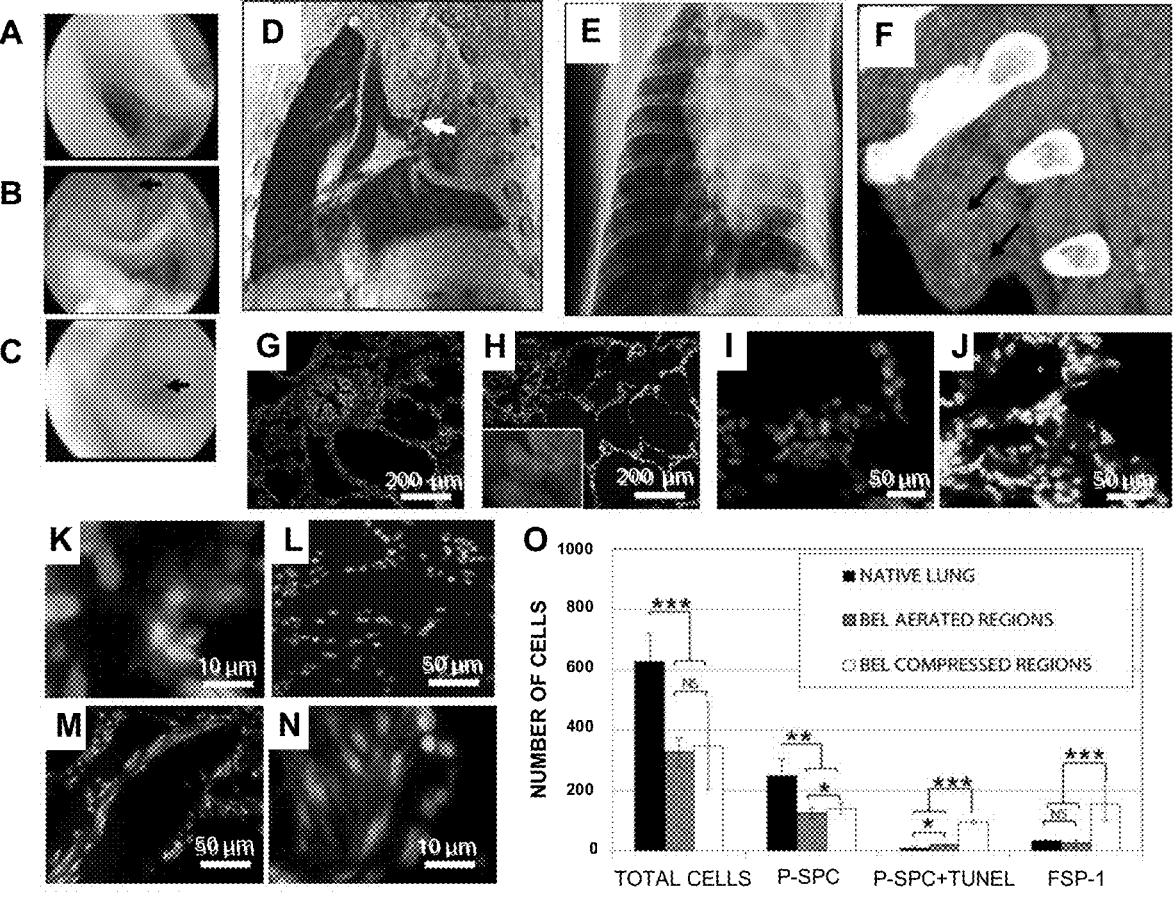

Pig-5 developed an occlusion of the first branch of the main stem bronchus of the BEL post-transplant. Both passageways at the point of the carina were open as shown in bronchoscopy done 2 months after transplant (FIG. 6A). In the BEL, the left bifurcation of the lung was occluded (FIGS. 6B and C). The lack of aeration of these airways resulted in compression of the BEL (FIG. 6E). Two weeks after surgery a chest X-ray was done due to the lack of breath sounds in the left chest cavity. The left lung appeared small, dense and partially aerated (FIG. 6E) although CT images indicated the presence of multiple intercostal vessels (FIG. 6F). As expected NL contained more cells and more P-SPC+ cells than BEL. In the BEL, we found large numbers of P-SPC+ aec II (FIG. 6H, G is control) and in compressed, non-aerated areas many aec II undergoing apoptosis (TUNEL positive) (FIG. 6 J-L, and O, I and K are controls). More FSP-1+ fibroblasts were found in non-aerated versus aerated regions of the lung or compared to NL (FIG. 6 M, N and O).

Immune Response of BEL

Figures 22A, 22B, 22C, 22D, 22E, 22F, 22G, 22H:
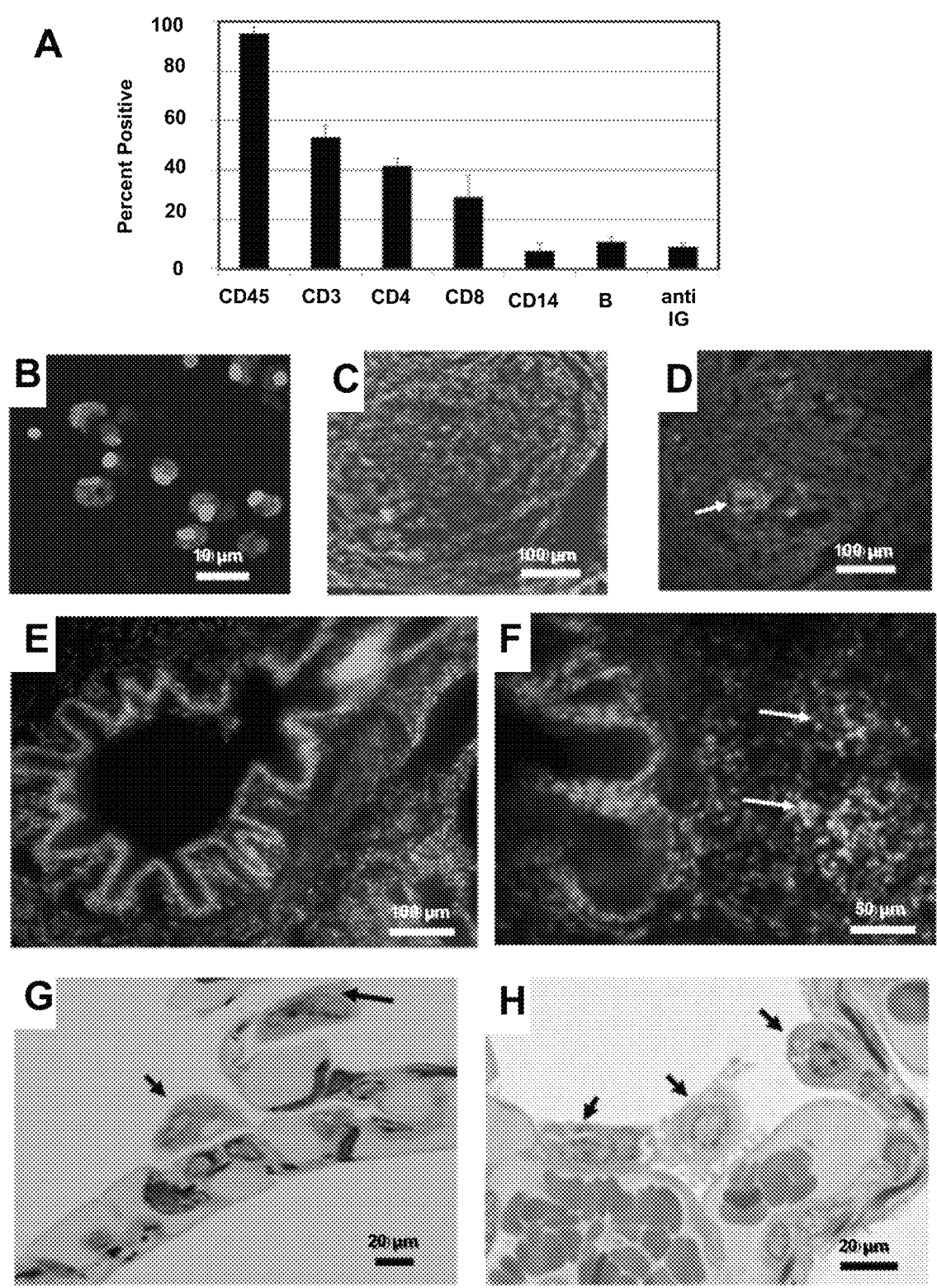

Despite strict adherence to aseptic technique, contamination of long-term bioengineered tissue cultures is a common problem. There is also increased susceptibility to infection of pulmonary grafts, following transplantation, due to direct contact with microbial contaminants during breathing (39, 40). As a preventative antimicrobial strategy pre- and post-transplant, the immune systems of BELs were reconstituted. Autologous MNL were added on day 11 of bioreactor culture and autologous serum, alveolar macrophages (am) and MNL on day 30 prior to transplantation. MNLs included T-lymphocytes (CD4 and CD8), macrophages and B-lymphocytes and immunoglobulin G (IgG) positive B-lymphocytes (FIG. 22A).

In a subset of animals, distribution of immune cells following transplantation was tracked using CFSE labeled MNL (FIG. 22B) installed on days 11 and 30 of bioreactor culture. Following transplantation of the BEL, CFSE-labeled MNL were found in the superior tracheal bronchial and the inferior (carinal) tracheal bronchial lymph nodes (FIG. 22D) and in lymph associated tissue regions near bronchi (FIG. 22F). CFSE labeled MNL were not detected within other local lymph nodes (FIG. 22C), nor in the right NL (FIG. 22E). There was no sign of infection of BEL nor enlargement of perihilar lymph nodes post-transplantation. In BEL, alveolar macrophages reestablished their contact with the alveolar wall following installation of cells (FIG. 22G, black arrow). Post-transplantation alveolar macrophages were found dispersed throughout BELs (FIG. 22H, black arrow) of all animals.

Figures 7A, 7B, 7C, 7D, 7E, 7F, 7G, 7H, 7I:
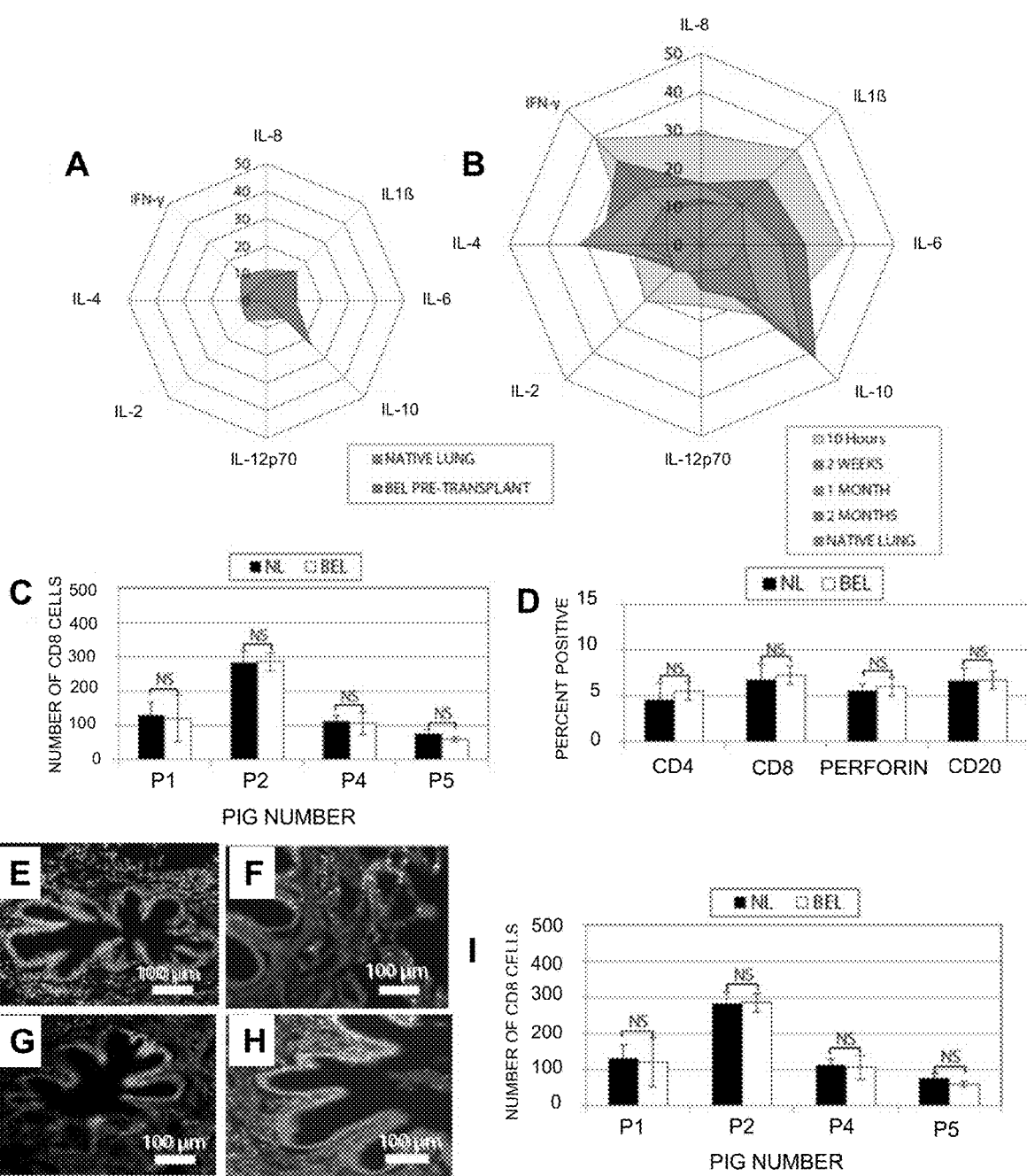

Bronchioalveolar lavages (BALs) were done on NLs removed at pneumonectomy, and BELs after euthanasia of each animal. Cytokine analysis was performed on BAL supernatants. There were low levels of pro-inflammatory cytokines in NL and BEL pre-transplant (FIG. 7A). Pig-2, euthanized 10 hours post-transplant, had a measurable pro-inflammatory immune response due to an undiagnosed infection at the time of euthanasia (FIG. 7B). Cytokine levels decreased as survival time of animals increased (FIG. 7B). There was no indication of a T cell response following BEL transplantation in pigs as indicated by low levels of IL-2 or IL-12p70. There were also no differences in CD8 cell counts between BEL and NL in BAL cell yield (FIG. 7C). Levels of CD4, CD8, perform containing cells or CD20 B-lymphocytes were not significantly different in BEL compared to NL (FIG. 7D). There was also no increase in CD8 cells in airways of BEL (FIGS. 7F and H; 7E and G are controls) compared to NL (FIG. 7I). These data indicate, that the autologous BEL was well tolerated, with no infiltration of leukocytes into tissues or upregulation of T cell responses indicative of graft dysfunction or rejection.

BEL Microbiome Development

Figures 8A, 8B, 8C, 8D, 8E:
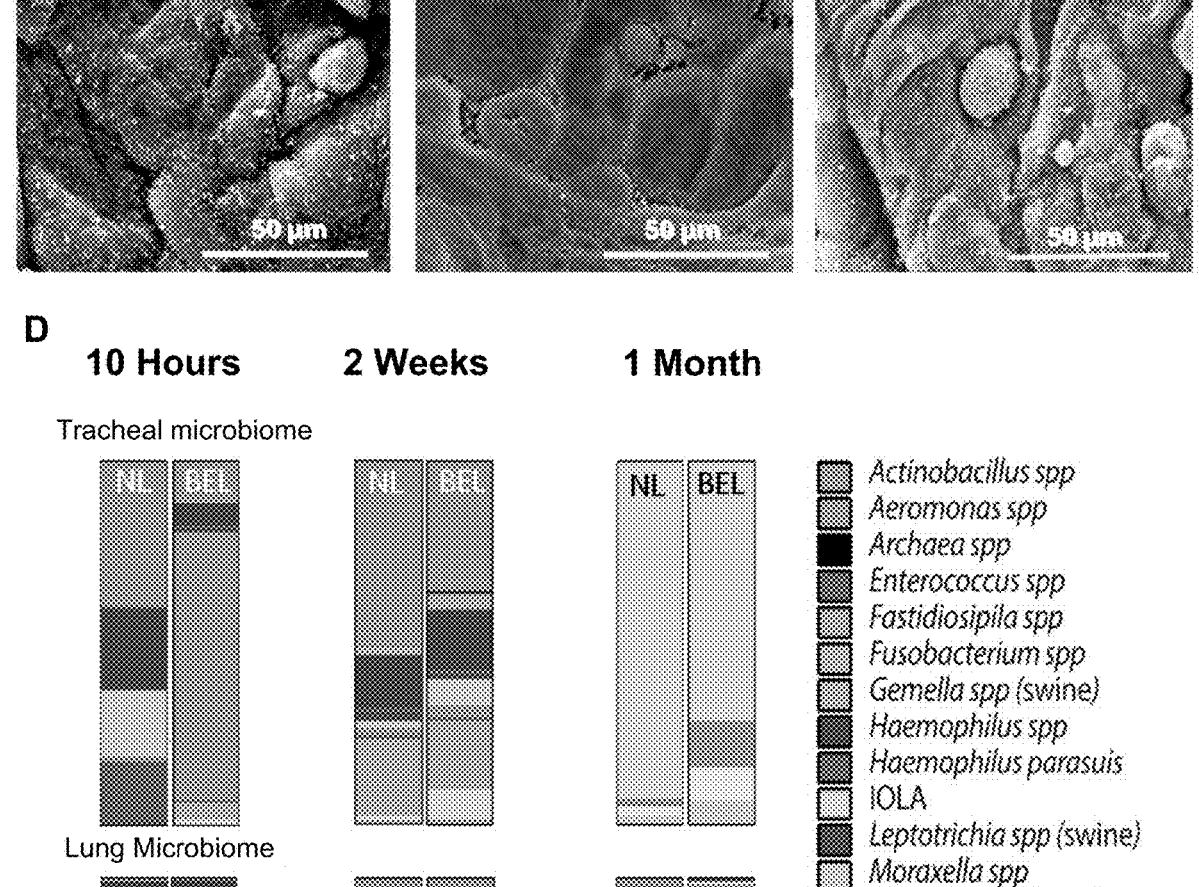

Transplantation of the sterile BEL created a unique opportunity to observe the colonization and establishment of the pulmonary microbiome communities in distinct compartments of the respiratory tree (40). NL contains a well-developed microbiome (FIG. 8A) but BEL are sterile pre-transplant and no organisms were found in upper (FIG. 8B) or lower (FIG. 8D) BEL until after transplantation (FIG. 8C). Evaluation of the established microbiome over a time course helped us address the BEL from the perspective of the bacterial community. We completed initial next generation sequencing (NGS) of samples from 4 pigs housed in our facility to identify the core microbiome of the respiratory tree. The resulting data were consistent with limited published microbiome data for pig lung (41) and identified the most common genera or species present in these laboratory animals. Optimized qPCR targets and assays were then established to quantify the common bacteria as well as selected minor species associated with pathogenic infections to evaluate the seeding of BEL (FIG. 25). One bacterial target was based on identification of 16S sequences that did not align with sequences in the SILVA database. Specifically, IOLA (infectious organism lurking in airways) (41, 42) 16S was seen in one of the transplanted and two of the control animals studied. This result was confirmed through cloning and sequencing of additional genomic fragments using published PCR primers (42).

Overall, the 30 tested samples representing paired BEL or NL from pig-1 (2 week survival), −2 (10-hour survival) and −4 (1 month survival) confirmed the 22 qPCR targets selected represented at least 80% and most often >95% of the total hits for each subsequent sample analyzed (based on summed totals relative to the universal 16S bacterial load). Samples from sterile scaffolds contained bacterial DNA levels at the lower limit of detection (<50 genomes; 16S qPCR). Interestingly, the overall bacterial load in each of the BEL or NL samples showed no differences other than the significantly reduced bacterial load (p<0.05 Student's T test) in lung samples (3 mm$^3$ tissue) from the 10 hour BEL transplant (AVG=6.1E4±3E3, n=3) relative to the NL from that animal (AVG=3.5E5±5E3, n=3). The tracheal samples from the same animal produced statistically similar bacterial loads (AVG=2.8E5±2E4, BEL vs. 8.68E4±2E3, NL) suggesting seeding and colonization had occurred in the 10 hour period for the trachea but had not yet reached completion in the lung. Paired BEL and NL samples from the animals transplanted for 2-weeks or 1-month showed no significant differences, thereby supporting the conclusion that microbiomes in the BEL had reached a stabilized steady state similar to the levels present in the NL.

The composition of each microbiome was evaluated for tracheal and lung samples from each of 3 pigs and are shown as proportional bar charts (average of at least two independent evaluations per sample) in FIG. 8. As noted above, tracheal and lung colonization occurred within 10 hours of the transplant, however the profile of these communities appeared to be less stabilized with more bacterial targets detected in the trachea of the transplant relative to the normal lung. Respiratory problems forced early euthanasia of this animal. The qPCR detected extreme levels of *Mycoplasma flocculare* in the bioengineered trachea and lung communities suggesting that this organism may have contributed to the clinical disease signs that warranted early euthanasia. The two-week BEL tissue showed slight but not significant differences in proportions of *Moraxella* species and *Staphylococcus* species in the trachea (p>0.05). The 1 month tracheal transplant tissue was not available for these studies but the normal tissue provided an indication of the similarity of tracheal and lung microbiome communities as shown in the lower half of FIG. 8.

The paired NL and BEL samples for the 2 and 1 month transplants also showed similar bacterial communities with nearly identical representation and proportions. There were some notable differences in the 1-month tissues where several bacterial targets were detected as minor components in the normal tissue but were not present in the BEL samples including the *M. flocculare* (43) observed in the 10 hour samples.

Discussion

To date, regenerative laboratories have attempted to engineer few whole organs. This endeavor requires engineering not only the organ but also vascular tissues to maintain a healthy organ with full functionality. We utilized nascent technologies and methods to enhance AC scaffolds including production and use of nanoparticles to deliver growth factors to support cell attachment and tissue formation. The selection of these factors at the time of cell installation ultimately effects survival and functionality of tissue post-transplant. We concentrated our initial efforts on developing the micro-vasculature and systemic support in the BEL and found that collateral systemic circulation developed in all animals survived 2 weeks or longer. Since BEL was supplied with oxygenated rather than deoxygenated blood, we were unable to assess gas exchange due to a lack of an oxygen gradient at the alveolar capillary junction.

Gene expression related to angiogenesis (44, 45) and lung tissue development (46, 47) indicated that tissue development was still in progress at 1 month post-transplant. Upregulated genes included MAPK14 TGFB2 PDGFC, VCAM1 and VEGFD which support angiogenesis (44). Histological examination of tissues indicated that collateral circulation developed in all animals as early as 2 weeks post-transplant. Blood vessels in all animals expressed eNOS, required for maintenance of vascular integrity (45), as well as ACE (33, 34) and ERG (35, 36). Aec I and II cell associated genes as well as genes related to mucin production; neuroendocrine cell function, Clara cells and smooth muscle cells (FIG. 18) also remained upregulated at 1 month post-transplant. Genes related to cell proliferation (FOXR2, PCNA, MKI67), lung growth and development (TBX5, FGF10, SHH, FOXA1, WNT5A) were also expressed. Histologic evaluation showed clear progression in lung and airway epithelial cell development with an associated increase in overall cell numbers and aec I cells in animals survived from 10 hours to 2 months. Cells associated with lung specific lineages were found in all animals at all time points examined, although, there were few Clara cells in the developing airways of animals due to the lack of primary Clara cells in the PTB preparation. One obvious limitation of this study is the small sample size related to genome analysis, but this finding was supported by other methods of analysis, and indicated that genes related to angiogenesis and lung cell lineages remain elevated in BEL two months after transplantation.

Acute lung rejection characterized by perivascular and sub-endothelial mononuclear infiltrates or by lymphocytic bronchitis and bronchiolitis, was not seen in BELs. CD8+ perform positive cells were not increased in BALs or CD8+ cells in tissue sections from animals included in this study. Nor did we see a significant increase in the presence of pro-inflammatory cytokines in tissues isolated from BEL except in pig-2, survived 10 hours. This animal was later shown to have high levels of Mycoplasma flocculare, a swine pathogen. Based on these data we saw no indication of primary graft rejection in animals survived for 10 hours, 2 weeks, 1 month or 2 months based on BAL evaluations or histopathology. No marked structural abnormalities were found in BEL tissues in pigs-1, -2 or -4. Pig-5 however developed an airway occlusion following surgery and showed some underdeveloped areas. Representative images indicated that aerated regions of the lung displayed normal lung architecture.

Recent reports highlight a role for lung microbiota in control of lung injury and remodeling related to respiratory disease following transplantation, (48, 49) and development of bronchiolitis obliterans syndrome which impacts long term survival (50). Our study provided the unique opportunity to examine the reestablishment of the microbiome in a sterile BEL after transplantation. Our qPCR assessments indicated that the bioengineered tissues were quickly seeded and effectively colonized by the bacterial communities found in the NL. The sterile tissues appear to have been seeded via the trachea as evidenced by the results from the animal survived for 10 hours (FIG. 8) but more work will be required to confirm this route of colonization. In comparison, newborn microbiome colonization of the oral cavity and nasopharynx occurs within five minutes following birth, and microbiological communities continue to develop over the first year of life (51). These distinct bacterial communities were consistent with other reports for the swine lung (40) and were consistently reproduced in BEL. These evaluations also led to the novel observation of infectious organism lurking in airways (42) suggesting that this organism may be of pathogenic concern in swine; moreover, IOLA had previously been reported only in the human respiratory tract in association with clinical disease (42).

Conclusions

In conclusion, we have shown that the preparation steps related to production and supplementation of scaffolds was essential to the success of this study, and that we can successfully transplant BEL with the survival of animals. These results also support the utility of the platform used to produce and transplant BEL for the general study of BEL development including the transcriptome, vascular tissue development, immune response related to rejection and microbiome formation. This platform would also allow examination in future studies of the influence of the microbiome on BEL survival and function. Together these findings represent a significant advance in our understanding of production of bioengineered tissues for transplantation. Future studies will concentrate on procedures to allow continued maturation of the BEL in vivo with establishment of vascular flow via the pulmonary artery and pulmonary vein.

Materials and Methods

Study Design

The objective of this study was to explore development of the systemic circulation after transplanting BEL into a large animal (pig) model with tracheal anastomosis but without reattachment of the Pa. We utilized a 3D model of porcine lung tissue to select methods of growth factor delivery and scaffold supplements that enhanced vascular and lung tissue development. BEL were created from autologous primary lung and vascular cells isolated from a pneumonectomy done 30 days pre-transplant. Porcine lungs, for AC scaffold production or peripheral blood were obtained as discarded materials, and peripheral blood was obtained following protocols approved by Institutional Animal Use at University of Texas Medical Branch (UTMB) or Texas Methodist Hospital Research Institute (TMHRI). Animals were not immunosuppressed in this study. Replicate numbers of each experiment are included in the figure captions. Tissues from N=6 BEL pre-transplant and N=4 BEL following successful transplantation were randomized prior to examination. Histology analysis and cell counts were done by trained individuals who were blinded to the study. We demonstrated survival of animals post-transplant. One animal (pig-2) was euthanized early due to respiratory complications at 10 hours. Pig-5 developed an airway occlusion post-surgery limiting BEL development and samples from this animal were not used for microbiome analysis. Animals survived for 10 hours, 2 weeks, 1 month and 2 months all demonstrated development of collateral systemic circulation, BEL survival and tissue development post-transplant.

PRP Production

Porcine PRP was produced as previously described (1) from whole porcine blood isolated as part of a tissue sharing program at UTMB or from our animals at euthanasia. The platelet concentrations ($10^4$/μl) were 712.50+/−22.43 for 1/3v-PRP. PRP was kept at 4° C. until use to avoid clumping.

Isolation of MSC, MNL, M1 or M2 Cells and Cell Supernatants

The MNL fraction was isolated from porcine blood by Ficoll density gradient separation (Amersham-Biosciences, Piscataway, NJ) as described by the manufacturer. MSC were isolated from peripheral blood as previously described (52). Cells were plated in 150 cm$^2$ tissue culture flasks in Dulbecco's Modified Eagle's Medium (DMEM, Sigma, St Louis MO), 0.1 mM nonessential amino acids, 100-U/ml penicillin and streptomycin with 10% fetal calf serum (FCS) plus 0.2 mM L-glutamine. Cell phenotypes were determined as described (53) and were sorted using FACSAria flowcytometer to enrich the MSC population. MSC expressed CD105, CD90, CD29 and were negative for expression of hematopoietic lineage markers CD14, CD34, CD45 and Lineage-1 (Lin-1). Macrophages were isolated from MNL as described (53) and were plated in DMEM with 10% FCS. Macrophage subpopulations were generated using Promo-Cell Macrophage Generation Media (PromoCell, Heidelberg, Germany) as described by the manufacturer. The M2 cells were CD68+/CD80−/low/CD163+. M1 cells were CD68+/CD80+/CD163−/low. Culture supernatants were collected from MSC, macrophage, MNL, M1 or M2 cells or MNL stimulated with LPS 10 ug/ml of *E. coli* LPS (Sigma Chemical Co., St. Louis MO). For production of cell culture supernatants 1×10$^6$ cells were incubated for 7 days prior to collection of cell-conditioned media.

Animal Care and Procedures

Animal handling and surgical procedures were performed according to protocols approved by the Institutional Animal Care and Use Committee (IACUC) of University of Texas Medical Branch at Galveston and were compliant with guidelines of the American Association for the Accreditation of Laboratory Animal Care.

Anesthesia

Animals received thorazine, ketamine, xylazine and buprenorphine as a pre-med. All of the procedures were done on fully anesthetized pigs, intubated with an appropriate endotracheal tube (double lumen) and maintained with an appropriate level of isoflurane anesthesia gas delivered by an anesthesia machine.

Recipient Left Pneumonectomy Procedure

The recipient pig was anesthetized and placed in the right lateral decubitus position. A standard left anterolateral thoracotomy incision was performed one finger below the tip of scapula and extended along the rib. For the donor venous pedicle preparation, the veins were isolated and stapled using an automatic stapler. The inferior pulmonary ligament was released. The hilar dissection was done and the phrenic nerve was left uninjured. Pneumonectomy was performed in a standard fashion beginning with the division of the inferior pulmonary ligament, the sequential encircling of the PA and pulmonary veins followed by multiple firings of an endo GIA stapler staying as peripheral as possible.

Left Lung Transplantation

The chest was entered through the previous pneumonectomy incision site for each animal. The bronchus was dissected free and cut at the desired length. The BEL trachea was trimmed prior to implantation. The trachea-to-trachea anastomosis was completed using a running 4-0 PDS (Ethicon, Somerville, NJ) suture on the membranous portion of the airway and using interrupted 4-0 PDS sutures on the cartilaginous portion. The anastomosis was inspected using bronchoscopy. The chest cavity was filled with saline solution, left lung ventilation was initiated and the anastomosis tested for leaks by inflating the lung to up to 30 mmHg of pressure. The chest was closed in a routine manner. A 21 French tube was left in place and kept under negative pressure until the animal was awake and standing. Blood gas was measured using an I Stat Analyzer (Abbott).

IVIS Imaging

CFSE labeled cells in BEL were imaged using an Inveon (Siemens Medical Solutions USA, Inc., Knoxville, TN) utilizing a 12-bit X-ray imaging detector with 2048×3072 pixels. Images were acquired at high resolution with conversion to Hounsfield Units. The scanning protocol required 520 exposures over 360° with 70 kV, 500 microA X-ray source settings, and effective pixel width of 107 μm. Cobra software (Exxim, Pleasanton, CA) was used to reconstruct images. The useable field of view was 8.4 cm×5.5 cm and the bed pallet was 38 mm.

CT, MRI and Micro CT

CT imaging was performed on a Siemens Somatom Definition Flash, dual source, 256 detectors scanner, before and after administration of iodinated intravenous contrast (70 cc of Omnipaque 350), through venous access in the ear of the animal using Medrad Dual Syringe injector at a rate of 3 ml/sec. Pre-contrast images were performed to evaluate lung parenchyma, presence and location of surgical material, calcifications, and tracheobronchial anastomosis. Post-contrast images were obtained in early arterial (pulmonary arterial and aortic circulation) and delayed (venous circulation) phases. Axial images were acquired at 1 mm slice thickness and reformatted in coronal and sagittal planes. Subsequently, advanced 3D processing was performed on an independent General Electric (GE) Advantage Workstation (AW). MRI mages were obtained on Siemens Skyra 3 Tesla magnet using Steady State Free Precession (SSFP) sequence in axial plane, half-Fourier acquisition single-shot turbo spin-echo (HASTE) in coronal and axial planes, and phase contrast imaging for flow analysis.

Contrast enhanced MR angiography was performed during administration of Gadolinium based contrast (Multihance). The amount of Multihance was calculated based on weight of each animal using a human calculation model of 0.2 mL/kg dose. Quantitative analysis of pulmonary arterial and systemic flow was performed using Argus flow software after image acquisition.

Micro CTs were performed on a CereTom NL 3000 (Neurologica, MA, USA), an eight-slice tomograph with high-contrast resolution of 0.6 mm (developed for human head imaging in ICU). The image acquisition settings were tube voltage, 100 kV; tube current, 5 mA; axial mode with slice thickness of 1.25 mm. Image resolution was 512×512 pixels. The image sharpness was optimized to soft tissue.

RNA Extraction for Genome Analysis 2 cm$^2$ pieces were collected from freshly cut tissue, 500-1000 mg, and placed in vials containing 500 ul of RNA later solution (Ambion, the RNA company Cat #AM7021), then stored at −80 C until shipped on dry ice to David Christiani M. D. The tissue sample preparation used gentleMACS™ Dissociatior machine, M tube with homogenization solution. RNA purification was then performed using The Promega Maxwell RSC automatic instrument with the SimplyRNA tissue kit (Cat. #AS1340).

RNA-Seq Data Analysis

Preliminary processing of raw reads was done by Q$^2$ Solutions, who provided fastq files. Subsequently, Taffeta scripts (https://github.com/blancahimes/taffeta) were used to analyze the RNA-Seq data. Primer and barcode adapter trimming was performed using trimmomatic (v.0.32) (54). Reference files for the UCSC version of the susScr3 genome were obtained from Illumina's iGenomes. Trimmed reads for each sample were aligned to the reference susScr3 genome and known ERCC transcripts using STAR (v.2.5.2a) (55). Quality control processing included gathering the following parameters to assess whether reads were appropriately mapped: (1) Bamtools (v.2.3.0) (56) was used to count/summarize the number of mapped reads, including junction spanning reads, (2) the Picard Tools (v.1.96; http://picard.sourceforge.net) RnaSeqMetrics function was used to compute the number of bases assigned to various classes of RNA, according to the Sscrofa10.2 refFlat obtained from iGenomes. For each sample, HTSeq (57) (v.0.6.1) was used to quantify Sscrofa10.2 transcripts and ERCC Spike-Ins based on reads that mapped to the provided reference files. The DESeq2 R package (58) (v. 1.10.1) was used to obtain fragments per kilobase of transcript per million reads mapped (FPKM) values corresponding to raw reads. Fold changes across conditions of interest were computed in R 3.2.4 (59), while adding 1 to all counts to avoid zeros in divisions. ERCC Spike-ins dose response curves (i.e. plots of ERCC transcript FPKM vs. ERCC transcript molecules) were created following the manufacturer's protocol (60). Raw read plots were created by displaying bigwig files for each sample in the UCSC Genome Browser.

Electron Microscopy

For TEM, pieces of BEL and NL were fixed in 2.5% glutaraldehyde in Na-cacodylate buffer, post fixed in 1% Osmium tetroxide dehydrated and finally embedded in SPI-pan 812 (SPI supplies, Chester, PA) and polymerized. TEM sections were stained with lead Citrate and uranyl acetate and observed on an FEI Tecnai 12 Spirit with images recorded using a Gatan CCD camera system. For SEM, tissues were fixed as described above, dehydrated through a graded series of ethanol and then placed in a critical point drier in liquid carbon dioxide (Tousimis, AutoSamdri-815, Rockville, MD), mounted on aluminum SEM stubs with silver conductive paint and coated with carbon (1 nm) and then with Au/Pd (80/20) 4 nm. Samples were imaged and recorded using an FEI Quanta 200 FESEM MK II.

Histopathology and IHC Staining

BAL were done as described (61). Cells were stained immediately, or were fixed with 2% paraformaldehyde (PAF) prior to staining and analysis. Antibodies used in this study, dilutions of primary antibody, secondary antibody and source of antibodies are listed in the tables in FIGS. 23 and 24. For negative controls, immunoglobulin (IgG) and species-matched isotype control antibodies were used, or primary antibodies were omitted, and cells were stained with secondary antibodies alone to set baseline values. Phenotype analysis was accomplished by using a FACSAria instrument (BD Biosciences, San Jose, CA), using the FACSDiva program (BD Biosciences). Data from 10,000 cells were acquired for each sample. Location and intensity of fluorescent labels were examined using fluorescent microscopy. Preparations for imaging were mounted in Slow Fade GOLD with 4',6-diamidino-2-phenylindole (DAN) (Molecular Probes, OR) and observed using an LSM 510 Meta advanced laser scanning confocal microscope (Zeiss, Thornwood, NY). Fluorescent microscopy was done using a Zeiss Axioscope Fluorescent microscope or a Nikon T300 Inverted Fluorescent microscope (Nikon Corp.). For tissue sections, positive cells on a slide were counted. Three replicate evaluations of cell counts for stained slides were performed and counts were later checked by a second observer.

Assessment of Apoptosis

In Situ Cell Death Detection Kit (Roche) was used according to the manufacturer's protocol. In brief slides were rinsed with Dulbeccos phosphate buffered saline (DPBS), 50 µL of TUNEL reaction mixture was added to the sections and incubated for 1 h at 37° C. Negative control slides were incubated with label solution alone. After incubation sections were rinsed with DPBS and embedded in antifade mountant. Tissue sections were evaluated under a fluorescence microscope. 5 random fields of the tissue sections were evaluated by two observers to count TUNEL-positive cells.

Cytokine Profile—Cytometric Bead Array

BAL samples were collected from NL at the time of pneumonectomy or from BEL immediately following euthanasia. Interleukin-1β (IL-1β), interleukin-2 (IL-2), interleukin-4 (IL-4), interleukin-6 (IL-6), interleukin-10 (IL-10), tumor necrosis factor (TNF), and interferon-γ (IFN-γ) levels were measured using the BD™ Cytometric Bead Array Human Th1/Th2 and Human Inflammatory Cytokine Kits (BD Biosciences, San Jose, CA). Array was performed according to the manufacturer's instructions.

Sample Preparation and DNA Extraction for Microbiome Analysis

Tissues from selected sites in the pulmonary tree of the BEL were collected immediately after euthanasia and were harvested with sterile tools into DNA/RNA-free plasticware. A 3 mm$^3$ portion of tissue was placed directly into commercial bacterial lysis solution (Roche) and then snap frozen on dry ice before storage at −80 C until DNA was extracted. Samples, in 350 ul of MagnaPure bacterial lysis solution, were subjected to both mechanical and proteinase steps to enhance complete genomic isolation prior to automated extraction in a MagnaPure96 magnetic bead system (Roche; Indianapolis, IN).

Lung Microbiome-Ion Torrent 16S rDNA Sequencing

Isolated DNAs were amplified with a panel of 5 "universal" fusion primer pairs that create overlapping 400-500 bp DNA fragments covering 95% of the bacterial 16S gene. The bar coded (Ion Xpress Barcodes) amplimers were mixed at equal ratios and then subjected to Ion Torrent NGS using the associated chemical reagents (ThermoFisher Scientific Inc, Waltham, MA). Average read length for this approach is >300 bases and produced sequence for both strands allowing higher confidence calls of bacterial identity. For the vast majority of bacteria, all 5 contigs were produced by the PCR.

NGS reads were filtered for quality and binned according to Ion Xpress barcoding using Ion Torrent Suite software (v 4.0.2). Sequencing reads in FASTQ format were further processed using web-based Galaxy software where each barcoded read was trimmed to remove the primer sequence; the 16S sequences then were compared to the SILVA 16S database using bowtie2 software to yield both a call to species or genera level as well as the number of times each sequence matched the database (hit-rate). The 16s sequences that did not align to the SILVA database were extracted and enumerated to identify the sequences with highest representation which were compared against the NCBI database using BLAST to identify other bacteria present in the samples. Positive bacterial identification required that at least two contiguous regions were identified as the same bacterial genus or species to be included as a hit in the curated dataset (i.e. a minimum of ~500 bp of contiguous 16S rDNA sequence was required). Where multiple calls to the same genera were made the number of hits were added accordingly. These numbers were converted to percentage of total to give an overall ratio of the sequenced microbiome sample. We completed 10 distinct sequence runs representing tissues from each portion of the respiratory tree as foundational data to identify the most common bacterial elements for the under reported swine microbiome. These results were used to select qPCR targets to quantify the levels of 22 common bacterial present in the core microbiomes (FIG. 25).

Lung Microbiome qPCR

Custom PCR primers or well characterized published primer pairs were selected and optimized for use in these assays (FIG. 25). Two control targets were included to assess the quality of the DNA and tissue (the single copy swine GAPDH gene) and the overall bacterial DNA burden in each sample ("universal 16S" target). For the qPCR, each 25 µl reaction contained 12.5 µl Sybr Supermix™ (Bio-Rad, Hercules, CA), 200 nM final concentration of forward and reverse primers, 1 µl of DNA template and nuclease-free water. Sybr green dye was used to track specific amplification in each reaction. PCR was completed in a C1000 thermocycler equipped with a CFX™ reaction module (Bio-Rad) using cycling parameters optimized for each primer pair (FIG. 25). A final high resolution melt temperature gradient from 75.0-90.0 C with 0.2 C increments between 0.05 second reads provided data to confirm the identity of each amplimer. Fluorescent signal data was collected at the end of each annealing/extension step. Starting quantity values were extrapolated from standard curves of plasmids harboring the PCR targets.

Statistical Analysis

All viability, genomic, histology, imaging and microbiome analysis data compared BEL to NL. For cell phenotype analysis 10,000 cells were collected for each flow cytometry sample examined. For specified data comparisons a paired samples Students t-test was used to compare means. For other data sets ANOVA was used as noted. Statistical analyses for these data were performed using GraphPad Prism™ v7.0.04 (San Diego, CA). Mean values and standard deviations are reported. Mean differences in the values were considered significant when p was less (<) than 0.05. For microbiome analysis mathematical analyses were performed using Excel™ (Microsoft Corp., Redmond, WA), Graphing was competed using Excell™ or GraphPad InSTAT™ software (version 2003).

Example 2

Methods
Lung Decellularization Protocol

Lungs were harvested and prepared as previously described (1). Once fully thawed, the trachea and Pa of the harvested lung were cannulated and attached to separate pumping and waste systems. Lungs were then immersed in 0.2% dextrose solution made with MilliQ water with 0.5× antimycotic/antibiotic. The dextrose solution was perfused through the cannulated Pa in an open circuit at 100 mL/min and through the trachea at 100 mL/min for 2 minutes then stopped for 2 minutes and repeated for three days with fresh dextrose solution every 24 hours. On day 4, the dextrose solution was removed and replaced with 2% SDS with MilliQ water. The remainder of the protocol has been previously described (1, 14). The lungs were then stored in a solution of DPBS, antimycotic and antibiotic at 4° C. Whole AC lungs or large AC blood vessels dissected from lung scaffolds were cut into 3×3×0.5 cm squares for studies to select additives influencing cell attachment, viability or proliferation.

Removal of SDS

Verification of the removal of SDS from the scaffold was done using methylene blue reagent. Reagent was prepared with 250 mg methylene blue, 50 g sodium sulfate and 10 ml sulfuric acid in 990 ml DI water. A 0.6 ml of sample was taken and 0.6 ml of methylene blue reagent and 2.4 ml of chloroform were added to the sample. The sample was vortexed for 3 minutes. Samples were centrifuged at 4500 rpm for 10 minutes. The top methylene blue layer was removed and 100 mg sodium sulfate was added. Standard SDS solutions were prepared at five known concentrations of 0%, 0.00025%, 0.0005%, 0.001% and 0.002%. A standard curve of these known concentrations was created and used to determine the concentration of SDS in the sample. Scaffolds containing no trace of SDS were then perfused with Dulbecco's phosphate buffered solution (DPBS) containing streptomycin (90 ug/ml), penicillin (50 U/ml) and amphotericin B (25 ug/ml) for 5 hours.

Sterilization of Scaffolds

Scaffolds were sterilized before cells were installed. Scaffolds were treated with 0.05% $H_2O_2$ for 10 minutes and then washed in sterile water 5 times and were kept in water for 30 minutes to remove any $H_2O_2$. Scaffolds were then treated with 70% ethanol for fifteen minutes, were again washed in sterile water five times, and were kept in water for 1 hour to remove any remaining ethanol. Scaffolds were then placed in DPBS containing penicillin (50 U/ml), streptomycin (90 ug/ml), and 25 ug/ml amphotericin for 24 hours. After 24 hours, scaffolds were placed in Dulbecco's modified eagle medium (DMEM) containing 10% FCS, penicillin (50 U/ml), streptomycin (90 ug/ml), and 25 µg/ml amphotericin at 5% $CO_2$ 37° C. overnight to verify sterility. Sterile scaffolds were kept incubated in DMEM for 48 hours prior to cell installations.

Multiphoton Microscopy and Second Harmonic Generation

Lung samples were imaged using MPM as previously described (1, 14). In brief, a previously described custom built nonlinear optical microscopy (NLOM) system was used for three-dimensional SHGM. The imaging system utilized a Nd:$YVO_4$ laser to pump a Ti:Sapphire femtosecond (~100 fs, 82 MHz) pulsed laser source (Tsunami, Spectra Physics), tunable within the wavelength range of 750-1000 nm. Inherent SHG from the collagen scaffold was induced by 840 nm laser light and signal was collected through a 420/20 nm bandpass filter. Incident power on the sample was kept constant at 28 mW throughout the study. Z-stacks were obtained (1 µm z-steps) using a 40×, 1.2 NA, C-Apochromat, water immersion objective. This objective provides a lateral field of view of 320×320 µm. Three-dimensional reconstruction of SHGM z-stacks were performed using image processing software IMARIS 7.4.2 (BITPLANE, Switzerland). Total collagen volume in these Z-stacks were measured by volume thresholding. Collagen density in the thresholded volumes were calculated by normalizing total collagen volume by total imaged volume.

Scaffold Supplementation Methods

Whole AC lungs or large AC blood vessels dissected from lung scaffolds were cut into 3×3 cm×0.5 cm squares. The scaffold pieces were placed into endothelial cell growth medium EGM (for PVASC cells) or small airway growth medium (SAGM) (for PL cells) (Lonza, Alpharetta, GA). For evaluation of factors supporting PVASC attachment, 5 million PVASC in EGM were loaded onto pre-treated 3×3× 0.5 cm squares of AC vascular scaffolds as described for PRP (1). After three days, the scaffold pieces were washed with warm PBS and attached cells were collected and counted.

To evaluate PL response pieces of lung scaffold were pre-treated with PF-127 hydrogel loaded with KGF, pig serum or supernatants from cell culture of MSC sup, Mac sup, M1 cell sup, M2 cell sup, MNL or LPS stim MNL sup. Pig serum or MSC sup, Mac sup, M1 cell sup, M2 cell sup, MNL sup or LPS stim MNL sup were isolated from 7-day cell cultures of each cell phenotype and were mixed with equal volumes of PF-127 hydrogel (20%) in DMDM-F12 prior to use on scaffold pieces or for installation into whole left lung scaffolds. MSCs, Macs, M1, M2, MNL or LPS stimulated MNL were added to scaffolds without pretreatment prior to PL cell installation. For evaluation of factors supporting PL attachment, 5 million PL in SAGM were loaded onto pre-treated 3×3×0.5 cm squares of AC vascular scaffolds. After scaffold pieces were seeded with cells, they were centrifuged at 100×g to help spread the cells throughout the scaffold. The seeded scaffolds were placed into individual wells of a six-well culture plate containing SAGM with 1004 ml primocin and were incubated for 7 days at 5% $CO_2$ 37° C. After three days, the scaffold pieces were gently washed with warm DPBS and unattached cells were collected and counted. After three days, the scaffold pieces were gently washed with warm DPBS and attached cells as well as Ki67 positive cells were counted.

Isolation of Primary Lung Cells or Primary Vascular Cells

As described previously for human lungs (1), whole porcine lungs were flushed with 0.5-1 liter of PBS containing 100 ug/ml of primocin (InvivoGen, San Diego, CA) an antibiotic formulation specifically designed to prevent primary cell contamination during cell culture. Pieces of distal lung were excised avoiding bronchioles and bronchi, and minced into 1-mm$^3$ fragments by using two scalpels cutting in opposite directions. Minced lung was treated with 1 mg/ml collagenase/dispase (Roche Diagnostics, Indianapolis, IN) for 5 hours at 4° C. Cells were filtered sequentially through 100—then 40-micron filters (BD Falcon, San Jose CA), and the filtrate was centrifuged to collect the PL cells. Cells were counted and placed into T75 filtered flasks containing SAGM (Lonza, San Jose, CA) plus 1% heat-inactivated porcine serum, primocin [100 ug/ml], and were then incubated at 37° C. with 5% $CO_2$. PVASC-Lung cells were isolated from blood vessels dissected from whole lungs, endothelial linings of the vessels scraped, and the resulting sheets of tissue were finely minced. Tissue was treated with collagenase for 3 hours at room temperature. Isolated cells were filtered sequentially through 100 and 40 micron filters, placed in BD Primaria T25 flasks (BD Falcon, San Jose, CA), and cultured in endothelial growth medium (EGM) (Lonza, San Jose, CA). Aliquots of lung cells from each donor were frozen as previously described (14).

Growth Factor Delivery

Discoidal mesoporous silicon microparticles were fabricated as previously described (20). Twenty four hours prior to use, 6 billion, 1000 nm×400 nm (diameter×height) discoidal particles with a 60 nm or 30 nm average pore size in isopropyl alcohol were dried in a speed vac. On the day of installation of particles into the lung scaffold, the particles were loaded with growth factor. MP (60 nm or 30 nm) were suspended and sonicated with 6.97 mL ice water. Then, 0.05 mg of recombinant human VEGF (Sigma, St. Louis MO), was added to the particles and mixed for a final concentration of 500 ng/ml of growth factor in 6 billion particles. Particles were incubated with growth factor at room temperature for thirty minutes to achieve loading. Particles were aliquoted into 1.5 mL tubes and washed by centrifuging and resuspending the pellet with ice water three times. The final suspension was then combined in 6 mL of ice water and was instilled into the lung scaffold six hours prior to the first PVASC installation. A human VEGF picokine ELISA kit (Boster Biological, Pleasanton, CA) was used to examine MP loads and release over time. The kit was used as described by the manufacturer. Load release was evaluated from 0.25-98 hours post loading (FIG. 9).

For hydrogel delivery of factors, PF-127 hydrogel was loaded with FGF2 or KGF (FGF7) (ProSpec-Tany, East Brunswick, NJ) by mixing 1 mg of human recombinant FGF2 (Thermo-Fisher Scientific), reconstituted as described by the manufacturer, in 20 mls of 4° C. PF-127 hydrogel (15%) in DMDM-F12. A human FGF2 ELISA kit or KGF ELISA kit (Invitrogen, Waltham, MA) were used to examine hydrogel load and release over time (0-96 hours). The kits were used as described by the manufacturer. Load release was evaluated from 0.25-98 hours post loading (FIGS. 9K and 9L). For administration of KGF, 10 mg of recombinant KGF (ProspecEast Brunswick, NJ) were reconstituted as described by the manufacturer in 10 mls of DMDM-F12. This was mixed with an equal volume of PF-127 hydrogel (20%) in DMDM-F12 prior to use. Load release was evaluated from 0.25-98 hours post loading (FIG. 10).

KI67 Staining

Cells were harvested, counted and pelleted prior to fixation in cold 70% ethanol, which was added dropwise to the pellet or fresh frozen section of tissue. Samples were incubated at 20° C. for two hours prior to washing with staining buffer (DPBS containing 1% FBS and 0.09% $NaN_3$). 20 µl of properly diluted anti-Ki-67 antibody (clone B56, BD Biosciences, Mountainview, CA) was then added to the sample according to the protocol. Cells were incubated in the dark at 4° C. for 30 minutes, were washed in staining buffer prior to addition of the secondary antibody and examined using flow cytometry, fluorescent or confocal microscopy.

Fibox4-PSt3 Oxygen Sensor System

The optical oxygen sensor spots, PSt3, with an area of 3.14 mm2 (PreSens Precision Sensing GmbH) were affixed to the inner surface of the bioreactor chamber or inline sensors were used to measure oxygen levels. A conventional two-point calibration of sensor spots, using atmospheric and 0% oxygen conditions as calibration points, were performed, per the manufacturer's instructions each day. Measurements taken twice a day 8 hours apart were averaged. Temperature was 37° C. with 5% CO2 and pH of media between 7.2 and 7.4. Percent of dissolved oxygen were measured for media alone, scaffold in media and BEL in media over 30 days of culture.

Measurement of Pulmonary Function

Static lung compliance measurements were done for porcine lungs after decellularization, following recellularization and were obtained using a ventilator (Model 300; Siemens-Elema). A cuffed endotracheal tube was placed in the trachea, secured with umbilical tape, and the cuff was inflated to seal the tube in the trachea. The ventilator was set to deliver sufficient tidal volume to generate a peak pressure of approximately 20 mmHg. Static lung compliance was measured using that function on the ventilator and displayed on the ventilator monitor.

Bronchoscopy

Video recordings of digital bronchoscopic examination of AC lung scaffolds were done during mechanical ventilation with a tidal volume of 400 mL and positive-end expiratory pressure (PEEP) of 5 mm Hg as previously described (1, 14). A bronchoscope (Olympus model BF Type P160, Olympus Exera CVL-160 light source, and Olympus Exera CV-160 image source) was advanced into the trachea or PA of lungs through a ported, double-swivel elbow connected to the breathing circuit. Digital video images were recorded with a Sony model VRDMC10 Multifunctional DVD recorder.

Bronchioalveolar Lavage

Bronchioalveolar lavage (BAL) was performed on NL following each left lung pneumonectomy. Cells were collected from BAL as previously described (61). Samples for genomic, microbiome and tissue analysis were removed from each NL prior to examination of the lung using during flexible bronchoscopy. Lungs were then flushed with two aliquots of 60-100 ml of 37° C. DPBS. Following administration of each aliquot of sterile saline, the fluid was removed using a syringe using gentle lung suction without collapsing the lung entirely. Samples were pooled, chilled and transferred to the laboratory where they were centrifuged to isolate cells and perform cell counts.

Histology and Immunohistochemistry

Tissues were removed from NL and BEL and were fixed in 2% PAF in DPBS overnight at room temperature. Small, 0.5-cm-sized pieces of tissue were cut from these pieces, frozen in tissue freezing medium (Triangle Biomedical Sciences), and sectioned on a Micro cryomicrotome (Thermos Scientific). Next, 6- to 8-μm sections of lung tissue were stained with H&E as previously described (1). For immunohistochemistry evaluation of tissues, primary and secondary antibodies, dilutions used and commercial sources are listed in FIG. 23. Nonspecific binding in sections was blocked by a 1-hour treatment in tris-buffered saline (TBS) plus 0.1% w/v Tween containing defatted milk powder (30 mg ml$^{-1}$). Stained sections were mounted in Slow Fade GOLD with 4',6-diamidino-2-phenylindole (DAPI) (Molecular Probes, OR) and observed by using an LSM 510 Meta advanced laser scanning confocal microscope (Zeiss, Thornwood, NY). For verification of cell phenotype, each slide was scored by counting three replicate measurements by the same observer for each slide. All slides were counted without knowledge of the cell-specific marker being examined, and results were confirmed through a second reading by another observer. For evaluation of numbers of blood vessels, five sections were counted by two observers, and the average number of vessels per slide was determined.

Flow Cytometry

Cells were stained immediately or, for identification of internal proteins, were fixed with 2% paraformaldehyde (PAF) prior to staining. For staining internal proteins, cells were fixed with 2% (w/v) PAF for 30 minutes at 37° C., washed in DPBS, and then permeabilized in 1% BD permeabilizing solution (BD Biosciences) for 10 minutes with a final wash in DPBS. For negative controls, corresponding immunoglobulin or species (IgG)-matched isotype control antibodies were used. In some instances, primary antibodies were omitted, and cells were stained with secondary antibodies alone to set baseline values for analysis markers or as staining controls. Use of isotype-matched controls and omission of primary antibodies served as negative controls and resulted in no detectable staining in confocal analysis or less than 2% background staining for flow cytometry analysis of samples. Phenotype analysis was accomplished by using a FACSAria instrument (BD Biosciences, San Jose, CA), with acquisition and analysis using the FACSDiva program (BD Biosciences). Data from 20,000 cells were acquired for each sample. Location and extent of fluorescent labels were also examined by using a Nikon T300 Inverted Fluorescent microscope (Nikon Corp., Melville, NY). Confocal microscopy was done on a Zeiss LSM 510 UV-META Confocal microscope.

Discussion

In summary, a fundamental problem facing the field of tissue engineering is our lack of ability to produce perfusable microvasculature networks capable of supporting tissue survival or of withstanding physiological pressures without leakage. This is critically important for production of bioengineered lung (BEL), which requires systemic circulation to support tissue survival and coordination of circulatory and respiratory systems to ensure proper gas exchange. In order to advance our understanding of vascular tissue development we designed methods to produce and transplant BEL without creation of a pulmonary artery anastomosis. While in bioreactor culture, we facilitated systemic vessel development using growth factor-loaded microparticles. A single pneumonectomy, performed one month prior to BEL implantation provided the source of autologous cells used to bioengineer the organ on an acellular lung scaffold. Animals were not immunosuppressed. Thirty days of bioreactor culture allowed the cells installed in the BEL to proliferate and initiate tissue development prior to implantation in a pig recipient. We evaluated recipient survival, autograft (BEL) vascular and parenchymal tissue development, graft rejection, and microbiome reestablishment in autograft animals survived for 10 hours, 2 weeks, 1 month and 2 months. BEL became well vascularized as early as 2 weeks post-transplant and formation of alveolar tissue was observed in all animals. There was no indication of transplant rejection. BEL continued to develop post-transplant and did not require addition of exogenous growth factors to drive cell proliferation or lung and vascular tissue development. The sterile BEL was seeded and colonized, by the bacterial community of the native lung.

Example 3

Use of Discoidal Silicon Microparticles to Support Vascular Engineering in Whole Lung Scaffolds To date, regenerative laboratories have attempted to engineer few whole organs. This endeavor requires support for production of lung tissue combined with coordinated development of vascular tissues to support tissue survival and lung function. The inability to produce whole bioengineered organs with perfusable microvasculature networks and vessels capable of supporting tissue survival and of withstanding physiological pressures without leakage is a fundamental problem facing the field of lung bioengineering. In the last 10 years our group has worked to produce transplantable whole bioengineered lung with appropriate micro and macro vascular development (1, 14, 71, 76, 77, 78) and procedures that support whole bioengineered lung production (78). Controlled release of growth factors influenced survival and functionality of tissue during in vitro culture and following transplantation (78). In recent studies, we concentrated our initial efforts on developing the microvasculature and systemic support in bioengineered lungs and found that collateral systemic circulation developed in all animals survived 2 weeks or longer after transplantation of a bioengineered lung. Vascular tissue development is critically important for production of bioengineered lung which requires production of a systemic circulation to support tissue survival and coordination of circulatory and respiratory systems to support gas exchange. We recently proved feasibility of bioengineered lung transplantation, with an airway anastomosis but without a vascular (pulmonary) anastomosis (78). The vascular tissue development was supported by release of vascular endothelial growth factor (VEGF) throughout the vascular regions of whole porcine lung scaffolds. VEGF is a critical growth factor involved in all stages of vascular development including neovascularization (32, 73, 75, 80). VEGF has also been shown to support development of the vascular tissue during bioengineering (Jiang 2015). VEGF was delivered to vascular sites in the scaffold by discoidal silicon microparticles (MP). Silicon MPs were selected for use in this study due to the ability to control pore size, which influences growth factor release over time, and also because of the need for repeated production of particles meeting good manufacturing practices (GMP) standardized production requirements as part of a plan to standardize production of MPs for production of clinically applicable bioengineered lungs. Particles needed to be manufactured on a regular basis with uniform stability, which allowed for controlled release of VEGF with an appropriate release profile. Developing a cGMP manufacturing process that could be appropriately scaled to meet commercial production demand was critical for the viability of the particle drug delivery technology. This was achieved by leveraging proven large-scale manufacturing techniques borrowed from the semiconductor industry for production of pharma-grade particles with the scalability to support research & development (R&D) studies, clinical trials, and future clinical commercial use.

Materials and Methods

Nanoporous Silicon MP Fabrication

Discoidal mesoporous silicon MPs were fabricated as previously described (20, 81). In summary, a one-step photolithography process was employed to define the particle geometry on a silicon wafer. A deep silicon etch was used to form uniform rows of silicon pillars. The pillars were coated with a protective oxide to enable subsequent processes. Eventually, the top oxide layer of the coated silicon pillars was removed prior to the electrochemical etch process. A programmed multi-cycled electrochemical etch provides uniform particle porosity and defined particle height. In the final manufacturing step, the MPs were released from the oxide layer and collected for use.

VEGF loading was accomplished as previously described (Jiang 2015). In brief, twenty-four hours prior to use, 6 billion, 1000 nm×400 nm (diameter×height) discoidal particles with a 60 nm or 30 nm average pore size in isopropyl alcohol were dried in a speed vac. On the day of installation of particles into the lung scaffold, the particles were loaded with growth factor. MP (60 nm or 30 nm) were suspended and sonicated with 6.97 mL ice water. Then, 0.05 mg of recombinant human VEGF (Sigma), was added to the particles and mixed for a final concentration of 500 ng/ml of growth factor in 6 billion particles. Particles were incubated with growth factor at room temperature for thirty minutes to achieve loading. Particles were aliquoted into 1.5 mL tubes and washed by centrifuging and resuspending the pellet with ice water three times. The final pellet was suspended in 1.5 ml of ice cold endothelial growth medium (EGM) prior to scaffold administration.

Production of Acellular Vascular Scaffolds

Adult porcine lungs were acquired from University of Texas Medical Branch IACUC approved studies as part of a tissue-sharing program. Lungs were harvested and prepared as previously described (1, 78) and were frozen at −70° C. until use. Once frozen lungs were thawed, the trachea and pulmonary artery of the harvested lung were cannulated and attached to separate pumping and waste systems. Lungs were then immersed in 0.2% dextrose solution made with MilliQ water with 0.5× antimycotic/antibiotic. The dextrose solution was perfused through the cannulated pulmonary artery in an open circuit at 100 ml/min and through the trachea at 100 ml/min for 2 minutes stopped for 2 minutes and repeated for three days with fresh dextrose solution every 24 hours. On day 4, the dextrose solution was removed and replaced with 2% sodium dodecyl sulfate (SDS) with MilliQ water. The remainder of the protocol has been previously described (78). The lungs were then stored in a solution of Dulbecco's phosphate buffered saline (DPBS), antimycotic and antibiotic at 4° C. until used. Whole acellular left lungs or large acellular blood vessels were dissected from lung scaffolds and were cut into 2.5 cm squares or used in 3 cm segments of whole vessels for studies to select additives influencing cell attachment and VEGF delivery.

Removal of SDS

Verification of the removal of SDS from the scaffold was done as previously described using methylene blue reagent (78). In brief reagent was prepared with 250 mg methylene blue, 50 g sodium sulfate and 10 ml sulfuric acid in 990 ml DI water. A 0.6 ml of sample was removed and 0.6 ml of methylene blue reagent and 2.4 ml of chloroform were added to the sample. The sample was then vortexed for 3 minutes. Samples were centrifuged at 4500 rpm for 10 minutes. The top methylene blue layer was removed and 100 mg sodium sulfate was added. Standard SDS solutions were prepared at five known concentrations of 0%, 0.00025%, 0.0005%, 0.001% and 0.002%. A standard curve of these known concentrations was created, and used to determine the concentration of SDS in each sample. Scaffolds containing no trace of SDS were then perfused with DPBS containing streptomycin (90 ug/ml), penicillin (50 U/ml) and amphotericin B (25 ug/ml) for 5 hours.

Sterilization of Scaffolds

Acellular lung scaffolds were sterilized before cells were installed. Scaffolds were treated with 0.05% $H_2O_2$ for 10 minutes and then washed in sterile water 5 times and were kept in water for 30 minutes to remove any $H_2O_2$. Scaffolds were then treated with 70% ethanol for 15 minutes, were again washed in sterile water five times, and were kept in water for 1 hour to remove any remaining ethanol. Scaffolds were then placed in DPBS containing penicillin (50 U/ml), streptomycin (90 ug/ml), and 25 ug/ml amphotericin for 24 hours. After 24 hours, scaffolds were placed in Dulbecco's modified eagle medium (DMEM) containing 10% FCS, penicillin (50 U/ml), streptomycin (90 ug/ml), and 25 μg/ml amphotericin at 5% $CO_2$ 37° C. for 24-48 hours to verify sterility. Sterile scaffolds were incubated in DMEM for 48 hours prior to cell installations.

Scaffold Supplementation Methods

Whole acellular left lung scaffolds or large acellular blood vessels dissected from right lung scaffolds were cut into 2.5 $cm^2$ squares or were used as whole 3 cm long sections of vascular scaffold. The scaffold pieces were placed into EGM prior to addition of VEGF-loaded MPs. A human VEGF picokine ELISA kit (Boster Biological) was used to examine hydrogel and MP growth factor load and release over time. The kit was used as described by the manufacturer. Load release for MPs attached to vascular scaffold was evaluated from 0.25-98 hours post loading.

For evaluation of VEGF-MP support of primary vascular cell attachment, 4 million lung derived vascular cells were loaded onto pre-treated pieces of acellular vascular scaffolds as described previously for assessment of supernatants supporting cell attachment (78) or for platelet rich plasma (PRP) (1, 78). The cell seeded scaffolds were placed into individual wells of a six-well culture plate containing EGM with 100 μg/ml primocin and were incubated for 7 days at 5% $CO_2$ 37° C. After three days, the scaffold pieces were gently washed with warm DPBS and unattached cells were collected and counted.

For MP delivery in whole left lung scaffold a mixture of 60 and 30 nm pore size VEGF-MPs were suspended in 5 ml of cold EGM and MP were pumped into the pulmonary artery at a flow rate of 0.5 ml/min until the solution began to drip from the pulmonary vein and IVIS imaging of scaffold indicated that maximum dispersal was achieved.

In order to track the location of the MP in whole lung scaffolds, small (1-2 cm³) cubes of whole left lung were removed from a variety of locations throughout the scaffold and were fixed overnight at room temperature in 2% paraformaldehyde (PAF) and frozen at 70° C. until they were sectioned.

Isolation of Primary Vascular Cells

As described previously for human lungs (1) or porcine lungs (78), whole porcine lungs were flushed with 0.5-1 liter of DPBS containing 100 ug/ml of primocin (InvivoGen) an antibiotic formulation specifically designed to prevent primary cell contamination during cell culture. Primary vascular lung derived cells were isolated from blood vessels dissected from whole lungs, endothelial linings of the vessels scraped, and the resulting sheets of tissue were finely minced. The Minced tissue was then treated with collagenase for 3 hours at room temperature. Isolated cells were filtered sequentially through 100 and 40 micron filters, placed in BD Primaria T25 flasks (BD Falcon), and cultured in EGM. Cells were counted and placed into T75 filtered flasks containing EGM plus 1% heat-inactivated porcine serum, primocin (100 ug/ml), and were then incubated at 37° C. with 5% $CO_2$.

IVIS Imaging

Carboxy fluorescein succinimidyl ester (CFSE) labeled primary lung cells in whole bioengineered lung were imaged using an Inveon (Siemens Medical Solutions USA, Inc., Knoxville, TN) utilizing a 12-bit X-ray imaging detector with 2048×3072 pixels. Images were acquired at high resolution with conversion to Hounsfield Units. The scanning protocol required 520 exposures over 360° with 70 kV, 500 microA X-ray source settings, and effective pixel width of 107 μm. Cobra software (Exxim, Pleasanton, CA) was used to reconstruct images. The useable field of view was 8.4 cm×5.5 cm and the bed pallet was 38 mm.

Histology and Immunohistochemistry

Tissues were sectioned on a Microm cryomicrotome (Thermo Scientific). Following sectioning, 6- to 8-μm sections of tissue were stained with hematoxylin & eosin (H&E) as previously described (1, 78). For immunohistochemistry evaluation of tissues, primary and secondary antibodies, dilutions used and commercial sources are listed in FIG. 26. Nonspecific binding in tissue sections was blocked, by a 1-hour treatment in tris-buffered saline (TBS) plus 0.1% w/v Tween containing defatted milk powder (30 mg ml-1). Stained sections were mounted in Slow Fade GOLD with 4',6-diamidino-2-phenylindole (DAPI) (Molecular Probes) and observed by using an LSM 510 Meta advanced laser scanning confocal microscope (Zeiss). For verification of cell phenotype, each slide was scored by counting three replicate measurements by the same observer for each slide. All slides were counted without knowledge of the delivery system being examined, and results were confirmed through a second reading by another observer. For evaluation of numbers of attached cells five sections, were counted by two observers, and the average number of cells per slide was determined.

Phenotype analysis was accomplished by using a FACSAria instrument (BD Biosciences), using the FACS-Diva program (BD Biosciences). Data from 10,000 cells were acquired for each sample. Location and intensity of fluorescent labels were examined using fluorescent microscopy. Preparations for imaging were mounted in Slow Fade GOLD with DAPI and observed using an LSM 510 Meta advanced laser scanning confocal microscope (Zeiss). Cells were stained for the presence of CD31, vascular endothelial-cadherin (VE-cadherin), smooth muscle actin (SM M ACT), and fibroblast specific protein-1 (FSP-1). Fluorescent microscopy was done using a Zeiss Axioscope Fluorescent microscope or a Nikon T300 Inverted Fluorescent microscope (Nikon Corp.).

Statistical Analysis

Statistical analysis was performed using GraftPad PRISM software (version 8). Mean values and standard deviation are reported. Analysis of variance (ANOVA) was performed and data was subjected to Tukey-Kramer multiple comparison test. Mean differences in the values were considered significant when p was less than 0.05.

Results

VEGF Delivery and Load Release

Figures 28A, 28B, 28C, 28D, 28E, 28F:
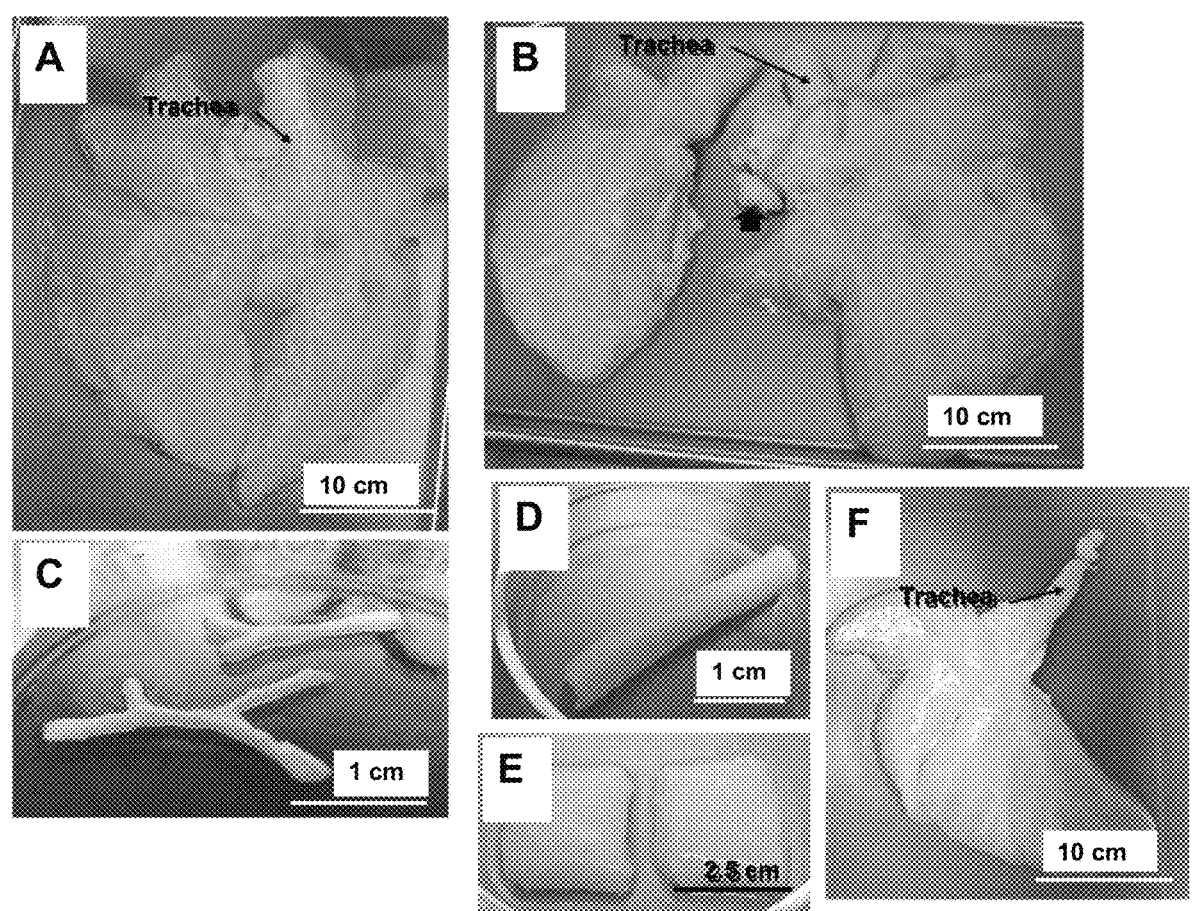

MPs were produced as previously described (20, 81) and a diagram demonstrating MP production is shown in FIG. 27. In order to produce whole double lung scaffolds, pig lungs were treated to remove cells and remaining blood as previously described for human or pig lungs (14, Nichols 2016). Lungs were selected for use following CT scan of scaffolds. Lungs containing damaged areas due to injury or disease were not used for production of whole left lung scaffolds. Left lung scaffolds were produced after surgically removing the right lung from the double lung set (FIG. 28A) which leaves a whole left lung scaffold connected to the trachea (FIG. 28B). Acellular vascular scaffolds were dissected from the vascular system of the right acellular lung (FIG. 28C-E). Small (FIG. 28C) and large vascular scaffolds (FIG. 28D) or 2.5 cm² pieces of vascular scaffolds were then produced (FIG. 28E). The small scaffolds were used to examine particle distribution and the influence of particle dispersal on cell attachment. Whole left lung scaffolds (FIG. 28F) were used to assess growth factor delivery methods in whole in vitro cultured lung scaffolds as part of a plan for standardization of procedures to produce bioengineered lung.

MPs can be produced with various pore sizes. The size of the pore influences the timing of the load release. In order to select the appropriate pore sized MPs for controlled delivery of VEGF we examined load release and influence of VEGF-release on cell attachment. For load release measurement, MPs suspended in EGM were added to the surface of ten 2.5 cm pieces of vascular scaffold. Load release of VEGF was examined over 98 hours of incubator culture at 37° C. using ELISA for 60 nm and 30 nm pore sized MPs and for an equal mixture of 60 and 30 nm pore sized MPs (FIG. 29).

Evaluation of Cell Attachment

Figures 30A, 30B, 30C, 30D, 30E, 30F, 30G, 30H:
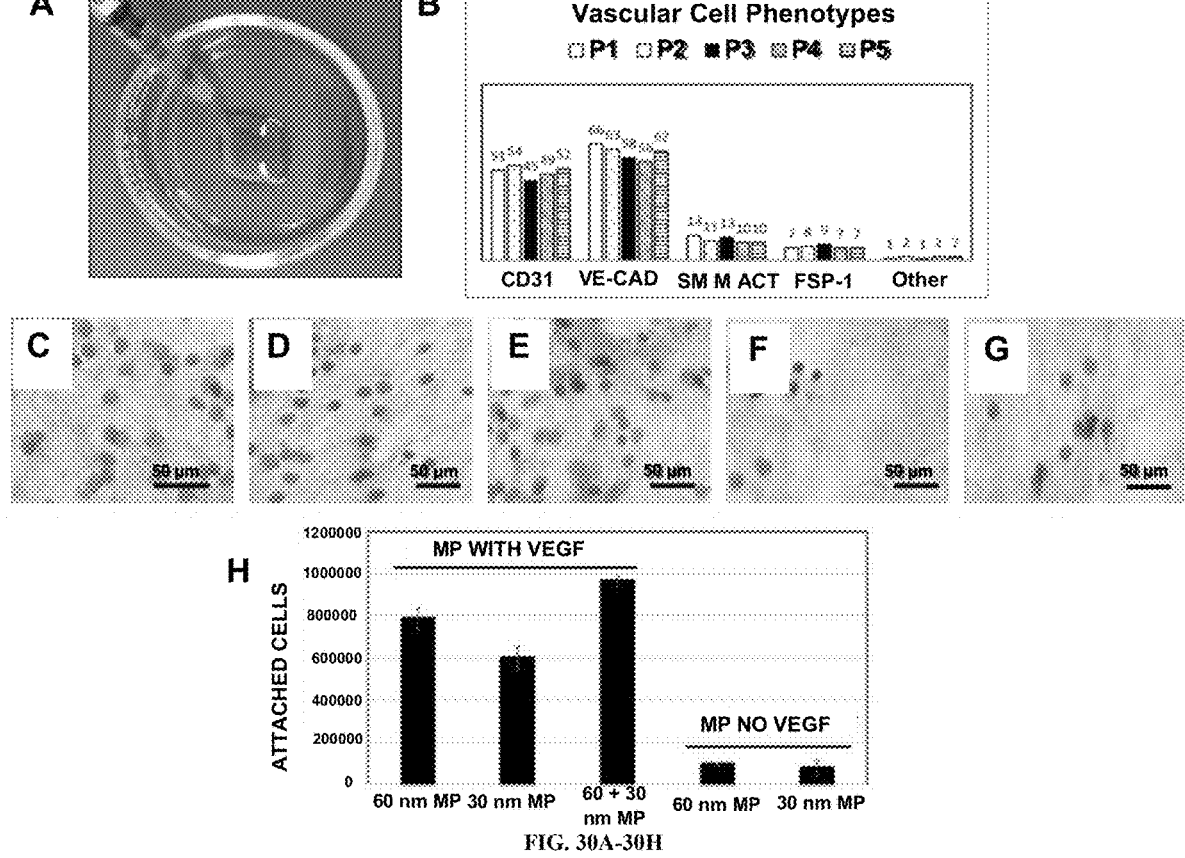

For analysis of cell attachment, 60 or 30 nm pore sized MPs or a mixture of 60 and 30 nm pore sized MPs were suspended in EGM and were added to the surface of ten 2.5 cm pieces of vascular scaffold. Each individual piece of scaffold was placed in a single well of an 6-well plate. Lung derived vascular cells were then delivered to the surface of the scaffold as shown in FIG. 30A and were allowed to adhere to the scaffold for 1 hour prior to addition of warm media to each well. The primary vascular cell mixture containing predominantly lung-derived CD31+, VE-CAD+ vascular endothelial cells also contained SM M ACT+ cells and FSP-1+ fibroblasts (FIG. 30B). After the second hour media was added to each well and cells were allowed to culture for 3 days. Scaffolds were gently washed to remove nonadherent cells and then were treated with collagenase to allow for collection of cells attached to the vascular scaffold surface. Representative H & E stained sections of scaffold treated with VEGF-60 nm pore sized MP (FIG. 30C), VEGF-30 nm pore sized MP (FIG. 30D) or a mixture of 60 and 30 nm pore sized MPs (FIG. 30E) are shown as are scaffolds treated with MP without VEGF (FIGS. 30F and 3). Averages of numbers of attached cells as well as controls without VEGF indicated that a combination of 60 and 30 nm MPs provided for higher levels of cell attachment than use of 60 and 30 nm pore sized MPs alone and allowed for release of VEGF over a longer period of time than use of 30 nm pore sized MPs alone (FIG. 30H).

Figures 31A, 31B, 31C:
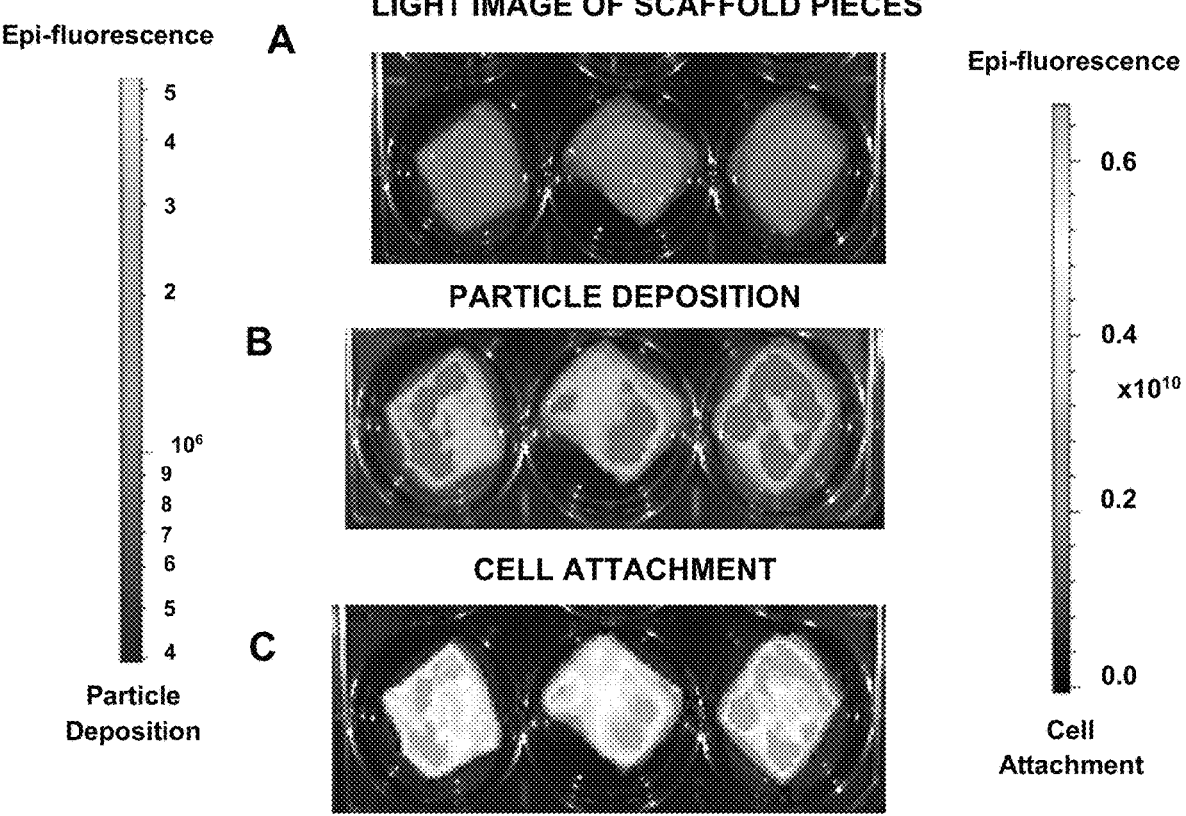
Figures 32A, 32B, 32C, 32D, 32E, 32F:
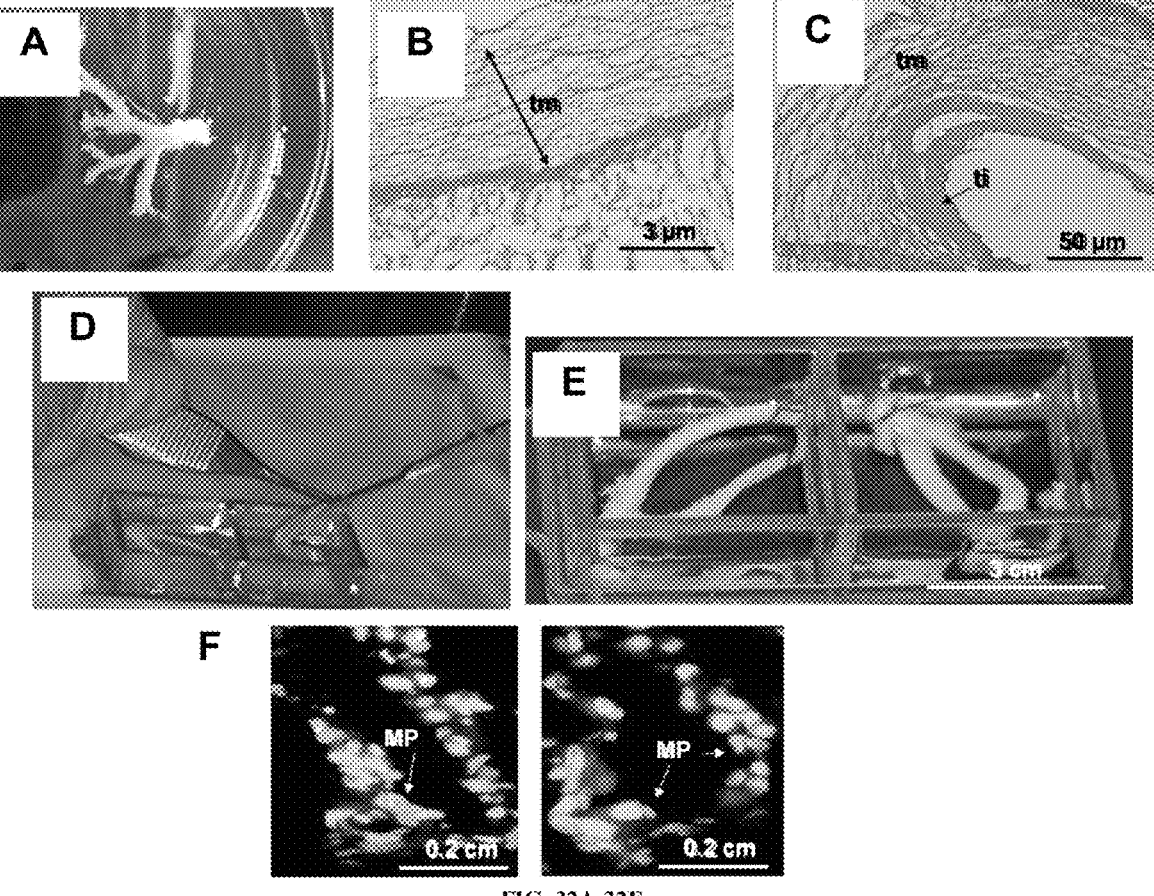

We were interested in knowing how dispersal of the location of MPs influenced cell attachment. In order to examine particle dispersal and the relationship between MP location and cell attachment we treated scaffolds with VEGF loaded MPs, stained for the presence of VEGF using mouse anti-human VEGF primary antibody and goat anti-mouse rhodamine red secondary antibody. A light image of a set of scaffold pieces treated with a combination of 60 and 30 nm MP are shown in FIG. 31A. IVIS imaging was used to examine dispersal of the rhodamine red stained MPs on the scaffold surface (FIG. 5B) prior to addition of CFSE-labeled cells (FIG. 31C). After 1 hour CFSE (green) tagged primary vascular cells were added to the scaffolds and scaffolds were then placed into a 37° C. incubator for 1 hour. Media was added to each scaffold at the end of 1 hour and cells were allowed to culture for 24 hours. IVIS imaging was done to allow for green CFSE fluorescence assessment of cell attachment (FIG. 31C). Although cells attached across the entire surface of the scaffold, highest numbers of cells were located in areas where particle deposition was the highest (FIG. 31B compared to C). Although good primary vascular cell attachment was achieved using VEGF-MPs on flat scaffolds we needed to determine if similar results would occur in whole vessels. Pieces of acellular blood vessels (FIG. 32A) were used to examine particle dispersal and cell attachment in a three-dimensional (3D) vessel. H & E stained sections of vascular scaffold show the extracellular matrix remaining after decellularization of the tunica intima and tunica media regions of the vessel (FIGS. 32B and C). It is difficult to distinguish the elastica interna in these sections. Ends of each vessel were tied off using suture material and MPs were delivered by injecting 0.1 ml of MP suspension into each vessel (FIG. 32D). Vessels were then incubated for an hour prior to addition of CFSE labeled vascular cells. Vessels were placed into a rotary bioreactor chamber overnight in a 37° C. incubator. After 24 hours vessels were fixed in 2% PAF and prepared for sectioning. Histological sections of the vessels were stained for VEGF using mouse anti-human VEGF antibody. MPs (red) and primary vascular cells (green) were dispersed throughout the vessels and lined the walls of the vascular scaffolds (FIG. 32F). MPs were retained within the mesh network of the acellular vascular scaffold and remained positive for VEGF after 24 hours of culture (FIG. 32F).

Supplementation of Whole Lung Scaffolds

Figures 33A, 33B, 33C:
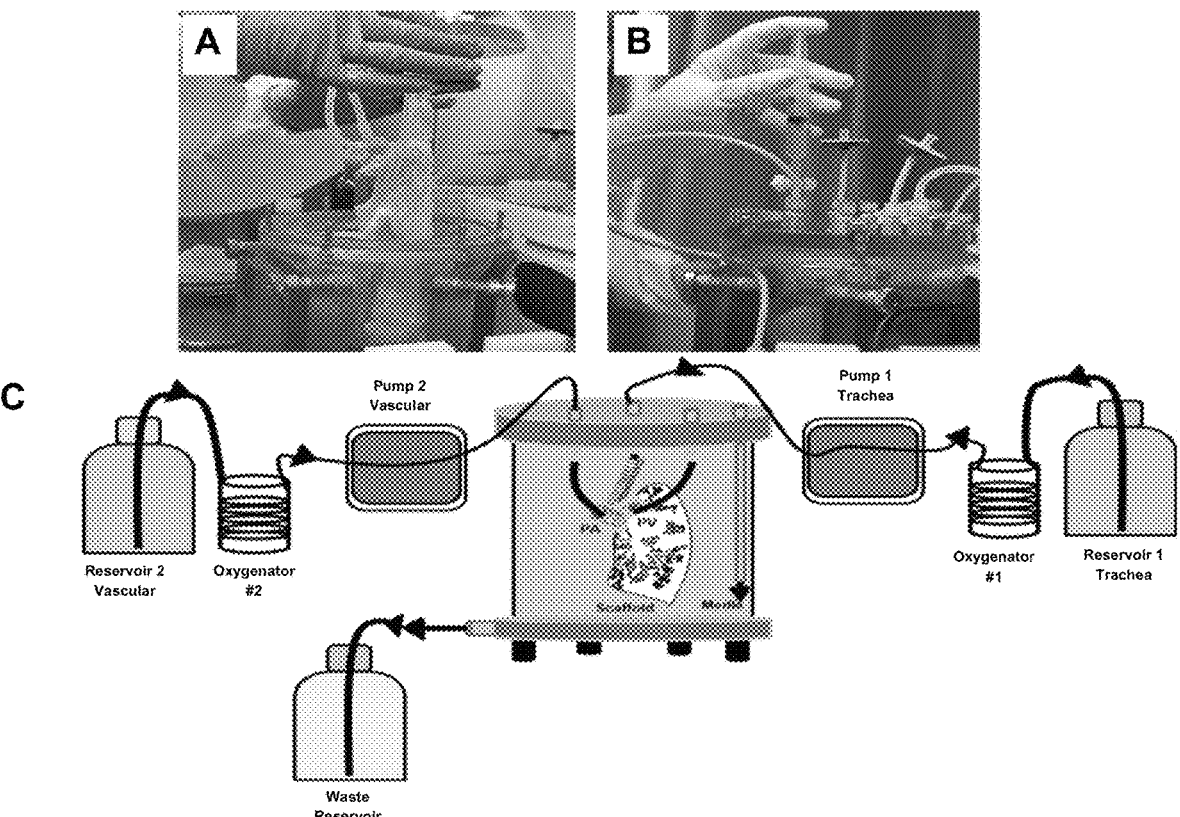
Figures 34A, 34B, 34C, 34D, 34E, 34F, 34G:
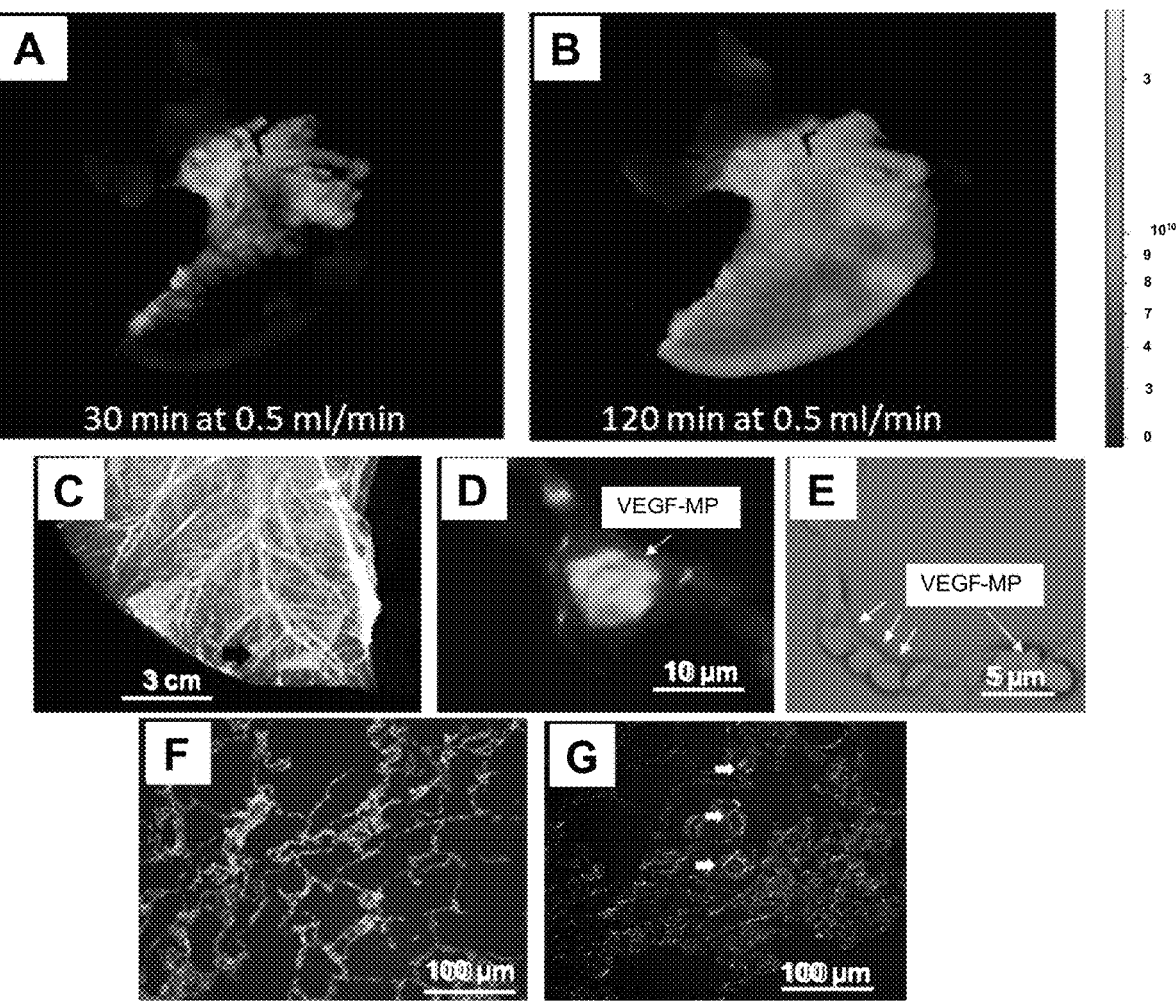

Whole left lung scaffolds were placed into the bioreactor chamber (FIG. 33A). The pulmonary artery, pulmonary vein and trachea were cannulated to allow for MP installation and media flow. MPs were installed by injection into the pulmonary artery and flushed through the vascular system at 0.5 ml/min (FIG. 33B). Installation of cells was done at a flow rate of 0.25 ml/min. A diagram of the fluidics system for the bioreactor (Harvard Apparatus) shows the flow of media into the trachea of the scaffold or the pulmonary artery (FIG. 33C). Instillation of the MP into the pulmonary artery allowed particle distribution throughout the whole lung scaffold even to distal sites of the lung vasculature (FIG. 34). MPs were visualized by staining for the presence of VEGF by immuno staining. In order to examine particle dispersal and the relationship between MP location of cell attachment we treated scaffolds with VEGF loaded MP, stained for the presence of VEGF using mouse anti-human VEGF primary antibody and goat anti-mouse rhodamine red secondary antibody. IVIS imaging was then used to examine dispersal of the rhodamine red stained MPs on the scaffold surface (FIGS. 34A and B). CT images of whole lung scaffold allow for visualization of the vascular tree within the scaffold (FIG. 34C). Even at the distal most regions of the lung small capillaries 3-4 um in size contained MPs (FIGS. 34D and E). In sections of native lung stained for the presence of CD31+ endothelial cells the location and amount of vascular tissue can be visualized (FIG. 34F). Similar distribution of MPs in vascular regions of the lung are seen in scaffolds following 120 minutes if MP dispersal (FIG. 34G).

Figures 35A, 35B, 35C, 35D, 35E, 35F:
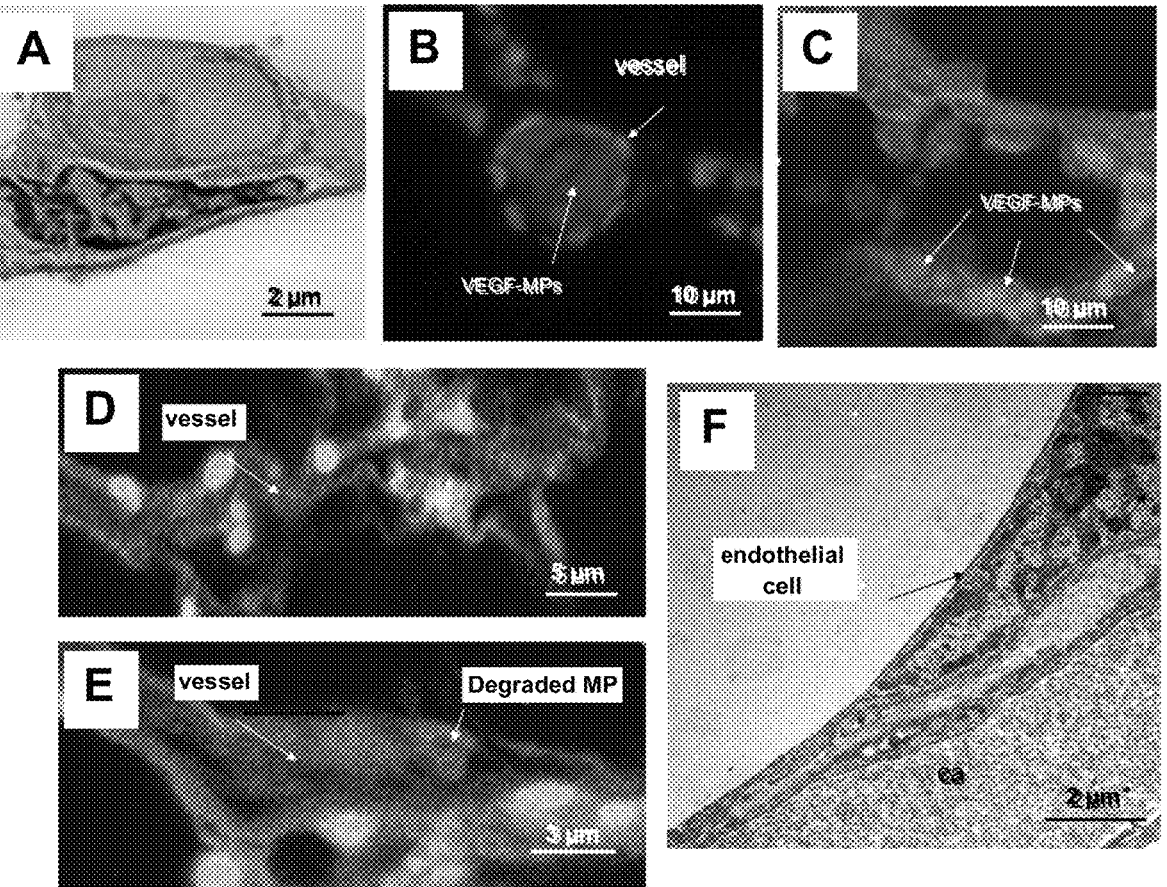

Vascular tissue development in whole lung scaffolds were examined after 10 days of in vitro bioreactor culture. The vascular system was maintained at a slow flow rate 0.5 ml/hour. A few MPs remained in the vascular regions of the lung scaffold although there were indications of particle breakdown (FIG. 35A-C). Degraded MPs remained positive for VEGF after 10 days of culture and aggregates of particles could be found in small (FIGS. 35A and B) as well as large blood vessels (FIG. 35C). Endothelial cells were always found in close proximity to VEGF+ MPs or particle aggregates and the lining of vessels was positive for the presence of VEGF but the growth factor was restricted to within the vascular scaffold (FIGS. 35D and E). MPs supported attachment of vascular cells to scaffolds and development of thin walled vessels and formation of capillaries in whole lung scaffolds (FIG. 35F).

Discussion

The inability to produce whole bioengineered organs with perfusable microvasculature networks and macrovascular vessels capable of supporting tissue survival and of withstanding physiological pressures without leakage has been a fundamental problem facing the field of tissue engineering. This is of critical importance in development of bioengineered lung due to the highly vascularized nature of lung tissue. In past studies we used pluronic F-127 hydrogel loaded with VEGF to support production of human bioengineered lung with variable results (1, 78). VEGFs and receptors (VEGFRs) regulate both vasculogenesis, the development of blood vessels from precursor cells during early embryogenesis, and angiogenesis, the formation of blood vessels from pre-existing vessels (20, 32, 73, 75, 81, 80). In our recent publication, we describe the ability to produce patent vascular tissue in most of the lung although some areas remained undeveloped (78). We attributed the lack of development of vascular tissue in these studies to the limited dispersal of VEGF in the whole organ scaffold combined with failure of the hydrogel growth factor mixture to be retained within the vascular scaffold framework. Because of this we initiated evaluation of a variety of delivery mechanisms which would allow for better retention of factors such as VEGF within the vascular scaffold and also allow extended release of VEGF over time.

One mechanism for growth factor delivery relies on use of particulates to facilitate controlled release of factors. Particulate delivery systems have become important in clinical medicine as potential drug carriers and controlled drug release devices (74, 79). Porous silicon MPs, developed as drug carriers, have many potential uses in the field of tissue engineering to control temporospatial release of growth factors during the process of tissue development. Our recent success developing whole bioengineered lung suitable for transplantation relied on the adequate development of the vascular system pre transplantation. This vascular development was supported by use of silicon MPs to aid in release of VEGF within the vascular portions of the scaffold (78). Although we knew that the particles supported tissue development, in this study we undertook a detailed evaluation of MP dispersal and influence of VEGF release on cell attachment in support of vascular development in the bioreactor. To this end we carefully compared MP dispersal and cell attachment in both small 2.5 cm pieces of lung scaffold and in whole acellular vascular scaffolds. We found that particles were easily delivered to vascular scaffolds by pumping MPs dispersed in EGM through the pulmonary artery of the scaffold. The size and shape of the MPs facilitated retention in the mesh like scaffold structure following installation and did not hinder dispersal. VEGF was not released outside of the vascular scaffold and particles could be distributed throughout whole left lung scaffolds including small capillary regions. VEGF was found in slowly degrading MPs and vascular development in vitro allowed for appropriate endothelial attachment and microvascular formation out to 10 days following cell installation.

In conclusion, we were able to show the importance of utilizing VEGF-MPs to enhance vascular development in a bioengineered lung. We took advantage of the different pore size MPs (60-30 nm) in order to deliver a precise and constant concentration of our growth factor to targeted areas in whole lung scaffolds. We showed that unlike thermosensitive hydrogels that do not provide a constant flow of growth factors, the MPs could be engineered to provide a steady state (time-release) concentration to an area where tissue production is necessary. We found that the ability to control release of VEGF over time was an important component in developing an intact barrier function in blood vessels pre transplantation that would most likely be capable of withstanding an increase in vascular pressure post transplantation. In future studies our focus will be developing and testing MP capabilities in the delivery of a variety of growth factors playing a role in tissue formation. At present our studies have shown that this technology is capable of making an important contribution in the process of establishing vascular support in any complex tissue or organ engineering.

One skilled in the art will readily appreciate that the present invention is adapted to carry out the objects and obtain the ends and advantages mentioned, as well as those inherent therein. The prior examples along with the methods, procedures, treatments, molecules, and specific compounds described herein are presently representative of preferred embodiments, are examples, and are not intended as limitations on the scope of the invention. Changes therein and other uses will occur to those skilled in the art which are encompassed within the spirit of the invention as defined by the scope of the claims.

The contents of the following references and all other references which are cited in this application are incorporated by reference in their entirety.

REFERENCES

1. J. E. Nichols, S. La Francesca, S. P. Vega, J. E. Niles, L. B. Argueta, M. Riddle, J. Sakamoto, G. Vargas, R. Pal, L. Woodson, J. Rhudy, D. Lee, D. Seanor, G. Campbell, V. Schnadig, J. Cortiella, Giving new life to old lungs: methods to produce and assess whole human paediatric bioengineered lungs. *J. Tissue Eng. Regen. Med.* 11, 2136-2152 (2017).

2. H. C. Ott, B. Clippinger, C. Conrad, C. Schuetz, I. Pomerantseva, L. Ikonomou, D. Kotton, J. P. Vacanti, Regeneration and orthotopic transplantation of a bioartificial lung. *Nat. Med.* 16, 927-933 (2010).

3. T. H. Petersen, E. A. Calle, L. Zhao, E. J. Lee, L. Gui, M. B. Raredon, K. Gavrilov, T. Yi, Z. W. Zhuang, C. Breuer, E. Herzog, L. E. Niklason, Tissue-engineered lungs for in vivo implantation. *Science* 329, 538-541 (2010).

4. R. W. Bonvillin, S. Danchuk, D. E. Sulllivan, A. M. Betancourt, J. A. Semon, M. E. Eagle, J. P. Mayeux, A. N. Gregory, G. Wang, I. K. Townley, Z. D. Borg, D. J. Weiss, B. A. Bunnell, A nonhuman primate model of lung regeneration: detergent-mediated decellularization and initial in vitro recellularization with messenchymal stem cells. *Tissue Eng. Part A* 18, 2437-2452 (2012).

5. X. Ren, P. T. Moser, S. E. Gilpin, T. Okamoto, T. Wu, L. F. Tapias, F. E. Mercier, L. Xiong, R. Ghawi, D. T. Scadden, D. J. Mathisen, H. C. Ott, Engineering pulmonary vasculature in decellularized rat and human lungs. *Nat. Biotechnol.* 33, 1097-1102 (2015).

6. S. Dimitrievska, L. E. Niklason, Historical perspective and future direction of blood vessel development. *Cold Spring Harb. Perspect. Med.* A025742 (2017).

7. M. J. Mondrinos, S. H. Koutzaki, H. M. Poblete, M. C. Crisanti, P. I. Lelkes, C. M. Finck, In vivo pulmonary tissue engineering: contribution of donor-derived endothelial cells to construct vascularization. *Tissue Eng. Part A* 14, 361-368 (2008).

8. C. T. Stabler, L. C. Caires, M. J. Mondrinos, C. Marcinkiewicz, P. Lazarovici, M. R. Wolfson, P. I. Lelkes, Enhanced re-endothelialization of decellularized rat lungs. *Tissue Eng. Part C Methods* 22, 439-450 (2016).

9. J. J. Song, S. S. Kim, Z. Liu, J. C. Madsen, D. J. Mathisen, J. P. Vacanti, H. C. Ott, Enhanced in vivo function of bioartificial lungs in rats. *Ann. Thorac. Surg.* 92, 998-1005 (2011).

10. S. Kaur, J. Cortiella, C. A. Vacanti, Identifying a site for maximum delivery of oxygen to transplanted cells. *Tissue Eng.* 6, 229-232 (2000).

11. A. P. Fishman, The clinical significance of the pulmonary collateral circulation. *Circulation* 24, 677-690 (1961).

12. J. Remy, F. Deschildre, D. Artaud, M. Remy-Jardin, M. C. Capin, R. Bordet, B. Gosselin, Bronchial arteries in the pig before and after permanent pulmonary artery occlusion. *Invest. Radiol.* 32, 218-224 (1997).

13. S. M. Kelly, J. H. T. Bates, R. P. Michel, Respiratory mechanics and gas exchange in postobstructive pulmonary vasculopathy. *Eur. Respir. J.* 8, 202-208 (1995).

14. J. E. Nichols, J. Niles, M. Riddle, G. Vargas, T. Schilagard, L. Ma, K. Edward, S. La Francesca, J. Sakamoto, S. Vega, M. Ogadegbe, R. Mlcak, D. Deyo, L. Woodson, C. McQuitty, S. Lick, D. Beckles, E. Melo, J. Cortiella, Production and assessment of decellularized pig and human lung scaffolds. *Tissue Eng. Part A* 19, 2045-2062 (2013).

15. M. Auton, D. W. Bolen, Predicting the energetics of osmolyte-induced protein folding/unfolding. *Proc. Natl. Acad. Sci. U.S.A* 102, 15065-15068 (2005).

16. F. Machi, M. Eisenkolb, H. Kiefer, D. E. Otzen, The effect of osmolytes on protein fibrillation. *Int J. Mol. Sci.* 13, 3801-3819 (2012).

17. X. Jiang, Q. Xiong, G. Lin, D. Cui, M. Xu, F. Chen, H. Geng, VEGF-loaded nanoparticle modified BAMAS enhance angiogenesis and inhibit graft shrinkage in tissue-engineered bladder. *Ann. Biomed. Eng.* 10, 2577-2586 (2015).

18. S. T. Robinson, A. M. Douglas, T. Chadid, K. Kuo, A. Rajabalan, H. Li, I. B. Copland, T. H. Barker, J. Galipeau, L. P. Brewster, A novel platelet lysate hydrogel for endothelial cell and mesenchymal stem cell-directed neovascularization. *Acta Biomater.* 36, 86-98 (2016).

19. A. Des Rieux, P. De Berdt, E. Ansorena, B. Ucakar, D. Jacobs, O. Schakman, E. Audouard, C. Bouzin, D. Auhl, T. Simon-Yarza, O. Feron, M. J. Blanco-Prieto, P. Carmeliet, C. Bailly, F. Clotman, V. Preat, Vascular endothelial growth-factor-loaded injectable hydrogel enhances plasticity in the injured spinal cord. *J. Biomed. Mater. Res. Part A* 102, 2345-2355 (2014).

20. B. Godin, C. Chiappini, S. Srinivasan, J. F. Alexander, K. Yokoi, M. Ferrari, P. Decuzzi, X. Liu, Discoidal porous silicon particles: fabrication and biodistribution in breast cancer bearing mice. *Adv. Funct. Mater.* 22, 4225-4235 (2012).

21. R. Thakker, P. Yang, Mesenchymal stem cell therapy for cardiac repair. *Curr. Treat. Options Cardiovasc. Med.* 16, 323 (2014).

22. M. Khatri, T. D. O'Brien, K. S. Chattha, L. J. Saif, Porcine lung mesenchymal stromal cells possess differentiation and immunoregulatory properties. *Stem Cell Res. Ther.* 6, 222-232 (2015).

23. H. Tao, Z. Han, Z. C. Han, Z. Li, Proangiogenic features of mesenchymal stem cells and their therapeutic applications. *Stem Cells Int.* 2016, 1314709 (2016).

24. S. C. Abreu, D. J. Weiss, P. R. M. Rocco, Extracellular vesicles derived from mesenchymal stromal cells: a therapeutic option in respiratory disease? *Stem Cell Res. Ther.* 7, 53 (2016).

25. L. Ionescu, R. N. Byrne, T. van Haaften, A. Vadivel, R. S. Alphonse, G. J. Rey-Parra, G. Weissmann, A. Hall, F. Eaton, B. Thebaud, Stem cell conditioned medium improves acute lung injury in mice: in vivo evidence for stem cell paracrine action. *Am. J. Physiol. Lung Cell. Mol. Physiol.* 303, L967-L977 (2012).

26. K. Guo, S. Ikehara, X. Meng, Mesenchymal stem cells for inducing tolerance in organ transplantation. *Front. Cell Dev. Biol.* 2, 8 (2014).

27. J. W. Lee, X. Fang, A. Krasnodembskaya, J. P. Howard, M. A. Matthay, Concise review: mesenchymal stem cells for acute lung injury: role of paracrine soluble factors. *Stem Cells* 29, 913-919 (2011).

28. D. I. Cho, M. R. Kim, H. Y. Jeong, H. C. Jeong, M. H. Jeong, S. H. Yoon, Y. S. Kim, Y. Ahn, Mesenchymal stem cells reciprocally regulate the m1/m2 balance in mouse bone marrow-derived macrophages. *Exp. Mol. Med.* 46, e70 (2014).

29. C. M. Minutti, J. A. Knipper, J. E. Allen, S. M. W. Zaiss, Tissue-specific contribution of macrophages to wound healing. *Semi. Cell Dev. Biol.* 61, 3-11 (2017).

30. S. Herold, K. Mayer, J. Lohmeyer, Acute lung injury: how macrophages orchestrate resolution of inflammation and tissue repair. *Front. Immunol.* 2, 65 (2011).

31. A. Quillien, J. C. Moore, M. Shin, A. F. Siekmann, T. Smith, L. Pan, C. B. Moens, M. J. Parsons, N. D. Lawson, Distinct notch signaling outputs pattern the developing arterial system. *Development* 141, 1544-1552 (2014).

32. J. E. Fish, J. D. Wythe, The molecular regulation of arteriovenous specification and maintenance. *Dev. Dyn.* 244, 391-409 (2015).

33. N. W. Morrell, S. S. Grieshaber, S. M. Danilov, R. A. Majack, K. R. Stenmark, Developmental regulation of angiotensin converting enzyme and angiotensin type 1 receptor in the rat pulmonary circulation. *Am. J Respir. Cell Mol. Biol.* 14, 526-537 (1996).

34. N. W. Morrell, E. N. Atochina, K. G. Morris, S. M. Danilov, K. R. Stenmark, Angiotensin converting enzyme expression is increased in small pulmonary arteries of rats with hypoxia-induced pulmonary hypertension. *J. Clin. Invest.* 96, 1823-1833 (1995).

35. A. V. Shah, G. M. Birdsey, Regulation of endothelial homeostasis, vascular development and angiogenesis by the transcription factor ERG. *Vascul. Pharmacal.* 86, 3-13 (2016).

36. G. M. Birdsey, A. V. Shah, N. Dufton, L. E. Reynolds, L. O. Almagro, Y. Yang, I. M. Aspalter, S. T. Khan, J. C. Mason, E. Dejana, B. Gottgens, K. Hodivala-Dike, H. Gerhardt, R. H. Adams, A. M. Randi, The endothelial transcription factor ERG promotes vascular stability and growth through wnt/$\beta$-catenin signaling. *Dev. Cell* 32, 82-96 (2015).

37. D. Fukamira, T. Gohongi, A. Kadambi, Y. Izumi, J. Ang, C. Yun, D. Buerk, P. L. Huang, R. K. Jain, Predoninant role of endothelial nitric oxide synthase in vascular endothelial growth factor-induced angiogenesis and vascular permiability. *Proc. Natl. Acad. Sci. U.S.A* 98, 2604-2609 (2001).

38. W. Zuo, T. Zhang, D. Z. A, Wu, S. P. Guan, A. A. Liew, Y. Yamamoto, X. Wang, S. J. Lim, M. Vincent, M. Lessard, C. P. Crum, W. Xian, F. McKeon, P63+ KRT5+ distal airway stem cells are essential for lung regeneration. *Nature* 517, 616-620 (2015).

39. T. Martinu, D. F. Chen, S. M. Palmer, Acute rejection and humoral sensitization in lung transplant recipients. *Proc. Am. Thorac. Soc.* 6, 54-65 (2009).

40. R. P. Dickson, J. R. Erb-Downward, F. J. Martinez, G. B. Huffnagle, The microbiome and the respiratory tract. *Annu. Rev. Physiol.* 78, 481-504 (2016).

41. M. C. Niederwerder, Role of the microbiome in swine respiratory disease. *Vet. Microbiol.* 209, 97-106 (2017).

42. K. Fukuda, K. Yatera, M. Ogawa, T. Kawanami, K. Yamasaki, S. Noguchi, R. S. Murphy, H. Mukae, H. Taniguchi, An unclassified microorganism: novel pathogen candidate lurking in human airways. *PLoS ONE* 9, e103646 (2014).

43. N. F. Friis, *Mycoplasm* suipneumoniae and *mycoplasma* flocculare in comparative pathogenicity studies. *Acta Vet. Scand.* 15, 507-518 (1974).

44. C. Lindskog, L. Fagerberg, B. Hallstrom, K. Edlund, B. Hellwig, J. Rahnenfuhrer, C. Kampf, M. Uhlen, F. Ponten, P. Micke, The lung-specific proteome defined by integration of transcriptomics and antibody-based profiling. *FASEB J* 28, 5184-5196 (2014).

45. L. Brasile, B. M. Stubenitsky, M. H. Booster, C. Haisch, G. Kootstra, NOS: The underlying mechanism preserving vascular integrity and during ex vivo warm kidney perfusion. *Am. J Transplant.* 3, 674-679 (2003).

46. L. M. Crosby, C. M. Waters, Epithelial repair mechanisms in the lung. *Am. J. Physiol. Lung Cell Mol. Physiol.* 298, L715-L731 (2010).

47. E. E. Morrisey, B. L. M. Hogan, Preparing for the first breath: genetic and cellular mechanisms in lung development. *Dev Cell* 18, 8-23 (2010).

48. E. Bernasconi, C. Pattaroni, A. Koutsokera, C. Pisan, R. Kessler, C. Benden, P. M. Soccal, A. Magnan, J. D. Aubert, B. J. Marsland, L. P. Nicod, Sys CLAD Consortium, Airway microbiota determines innate cell inflammatory or tissue remodeling profiles in lung transplantation. *Am. J. Respir. Crit. Care Med.* 194, 1252-1263 (2016).

49. S. Mouraux, E. Bernasconi, C. Pattaroni, A. Koutsokera, J. D. Aubert, J. Claustre, C. Pison, P. J. Royer, A. Magnan, R. Kessler, C. Benden, P. M. Soccal, B. J. Marsland, L. P. Nicod, SysCLAD Consortium, Airway microbiota signals anabolic and catabolic remodeling in the transplanted lung. *J. Allergy Clin. Immunol.* doi.org/10.1016/j.jaci.2017.06.022 (2017).

50. D. L. Willner, P. Hugenholtz, S. T. Yerkovich, M. E. Tan, J. N. Daly, N. Lachner, P. M. Hopkins, D. C. Chambers, Reestablisment of recipient-associated microbiota in the lung allograft is linked to reduced risk of bronchiolitis obliterans syndrome. *Am. J. Clin. Resp. Care Med.* 187, 640-647 (2013).

51. D. J. Gallacher, S. Kotecha, Respiratory microbiome of new-born infants. *Front. Pediatr.* 4, 10 (2016).

52. J. E. Nichols, J. A. Niles, D. DeWitt, D. Prough, M. Parsley, S. Vega, A. Cantu, E. Lee, J. Cortiella, Neurogenic and neuro-protective potential of a novel subpopulation of peripheral blood-derived CD133+ ABCG2+ CXCR4+ mesenchymal stem cells: development of autologous cell-based therapeutics for traumatic brain injury. *Stem Cell Res. Ther.* 4, 3-26 (2013).

53. J. E. Nichols, D. J. Mock, N. J. Roberts Jr, Use of FITC labeled influenza virus and flow cytometry to assess binding and internalization of virus by monocytes-macrophages and lymphocytes. *Arch. Virol.* 130, 441-455 (1992).

54. A. M. Bolger, M. Lohse, B. Usadel, Trimmomatic: a flexible trimmer for Illumina sequence data. *Bioinformatics* 30, 2114-2120 (2014).

55. A. Dobin, C. A. Davis, F. Schlesinger, J. Drenkow, C. Zaleski, S. Jha, P. Batut, M. Chaisson, T. R. Gingeras, Star: ultrafast universal RNA-seq aligner. *Bioinformatics* 29, 15-21 (2013).

56. D. W. Barnett, E. K. Garrison, A. R. Quinlan, M. P. Stromberg, G. T. Marth, BamTools: a c++ api and toolkit for analyzing and managing barn files. *Bioinformatics* 27, 1691-1692 (2011).

57. S. Anders, P. T. Pyl, W. Huber, HTSeq—a python framework to work with high-throughput sequencing data. *Bioinformatics* 31, 166-169 (2015).

58. M. I. Love, W. Huber. S. Anders, Moderate estimation of fold change and dispersion for RNA-seq data with DEeq2. *Genome Biol.* 15, 550-571 (2014).

59. R Core Team, R: A Language and Environment for Statistical Computing. R Foundation for Statistical Computing, Vienna, Austria, (2016).

60. A. Mortazavi, B. A. Williams, K. McCue, L. Schaeffer, B. Wold, Mapping and quantifying mammalian transcriptomes by RNA-Seq. *Nat. Methods* 5, 621-628 (2008).

61. E. P. Judge, J. M. L. Hughes, J. J. Egan, M. Maguire, E. L. Molloy, S. O'Dea, Anatomy and bronchoscopy of the porcine lung: a model for translational respiratory medicine. *Am. J. Respir. Cell Mol. Biol.* 51, 334-343 (2014).

62. R. A. Haugland, S. C. Siefring, L. I. Wymer, K. P. Brenner, A. P. Dufour, Comparison of *enterococcus* measurements in freshwater at two recreational beaches by quantitative polymerase chain reaction and membrane filter culture analysis. *Water Res.* 39, 559-568 (2005).

63. G. M. Matar, N. Sidani, M. Fayad, U. Hadi, Two-step PCR-based assay for identification of bacterial etiology of otitis media with effusion in infected Lebanese children. *J. Clin. Microbiol.* 36, 1185-1188 (1998).

64. C. Turni, M. Pyke, P. J. Blackall, Validation of a real-time PCR for *Haemophilus parasuis*. *J. Appl. Microbiol.* 108, 1323-1331 (2010).

65. V. Tocqueville, S. Ferre, N. H. Nguyen, I. Kempf, C. Marois-Crehan, Multilocus sequence typing of *Mycoplasma hyorhinis* strains identified by real-time TaqMan PCR assay. *J. Clin Microbiol.* 52, 1664-1671 (2014).

66. A. M. Guimaraes, R. F. Vieira, R. Poletto, R. Vemulapalli, A. P. Santos, W. de Moraes, Z. S. Cubas, J. N. Marchant-Forde, J. Timenetsky, A. W. Biondo, J. B. Messick, A quantitative TaqMan PCR assay for the detection of *Mycoplasma suis*. *J. Appl. Microbiol.* 111, 417-425 (2011).

67. M. Zozaya-Hinchliffe, R. Lillis, D. H. Martin, M. J. Ferris, Quantitative PCR assessments of bacterial species in women with and without bacterial vaginosis. *J. Clin. Microbial.* 48, 1812-1819 (2010).

68. L. Bergmark, P. H. Poulsen, W. A. Al-Soud, A. Norman, L. H. Hansen, S. J. Sorensen, Assessment of the specificity of *Burkholderia* and *Pseudomonas* qPCR assays for detection of these genera in soil using 454 pyrosequencing. *FEMS Microbial. Lett.* 333, 77-84 (2012).

69. D. M. Wolk, L. B. Blyn, T. A. Hall, R. Sampath, R. Ranken, C. Ivy, R. Melton, H. Matthews, N. White, F. Li, V. Harpin, D. J. Ecker, B. Limbago, L. K. McDougal, V. H. Wysocki, M. Cai, K. C. Carroll, Pathogen profiling: rapid molecular characterization of *Staphylococcus aureus* by PCR/electrospray ionization-mass spectrometry and correlation with phenotype. *J. Clin. Microgiol.* 47, 3129-3137 (2009).

70. T. Mohammadi, H. W. Reesink, C. M. Vandenbroucke-Grauls, P. H. Savelkoul, Optimization of real-time PCR assay for rapid and sensitive detection of eubacterial 16S ribosomal DNA in platelet concentrates. *J. Clin. Microbiol.* 41, 4796-4798 (2003).

71. J. Cortiella, J. A. Niles, A. Cantu, A. Brettler, A. Pham, G. Vargas, S. Winston, J. Wang J, S. Walls, J. E. Nichols, Influence of Acellular Natural Lung Matrix on Murine Embryonic Stem Cell Differentiation and Tissue Formation. Tissue Eng Part A. 16, 2565, (2010)

72. J. S. Fernandez-Moure, J. L. Van Eps, J. R. Rhudy, J, Cabrera, G. S. Acharya, E. Tasciott, J. Sakamotos, J. E. Nichols, Porcine acellular lung matrix for wound healing and abdominal wall reconstruction: a pilot study. Tissue Engineering and Regenerative Medicine 7, 1, (2016)

73. N. Ferrara, R. S. Kerbel, Angiogenesis as a therapeutic target. Nature. 438, 967, (2005)

74. K. K. Kyeong, P. Hongsuk, J. M. Lee, K. Na, E. S. Lee, pH-responsive starch MPs for a tumor-targeting implant. Polymers for Advanced Technologies, 29, 1372, (2018)

75. S. Lee, T. T. Chen, C. L. Barber, M. C. Jordan, J. Murdock, S. Desai, N. Ferrara, A. Nagy, K. P. Roos, M. L. Iruela-Arispe, Autocrine VEGF signaling is required for vascular homeostasis. Cell, 130, 691, (2007)

76. T. Luque, E. Melo, E. Garreta, J. Cortiella, J. E. Nichols, R. Farré, D. Navajas, Local micromechanical properties of decellularized lung scaffolds measured with atomic force microscopy. Acta Biomater. 9 (6), 6852, (2013)

77. E. Melo, E. Garreta, T. Luque, J. Cortiella, J. E. Nichols, D. Navajas, R. Farré, Effects of the Decellularization Method on the Local Stiffness of Acellular Lungs. Tissue Eng Part C Methods. (2013)

78. J. E. Nichols, S. LaFrancesca, J. A. Niles, S. P. Vega, L. B. Argueta, L. Frank, D. C. Christiani, R. Pyles, B. Hynes, R. Zhang, A. Miller, J. Sakamoto, J. Jessica Rhudy, G. Hendricks, F. Begarani, X. Liu, G. Vargas, R. Pal, I. Patrikeev, L. Woodson, A. Wacher, M. Grimaldo, D.

Weaver, R. Mlcak, J. Cortiella, The Next Step in the Production of Bioengineered Lungs for Clinical Application: Transplantation of Bioengineered Lung into a Large Animal Model. Science Translational Medicine 10, (2018)

79. A. A. S. Rizvi, A. M, Saleh, Applications of nanoparticle systems in drug delivery technology. Saudi Pharmaceutical Journal, 26, 64, (2018)

80. M. Shibuya, Vascular Endothelial Growth Factor (VEGF) and Its Receptor (VEGFR) Signaling in Angiogenesis Genes Cancer. 2, 1097, (2011)

81. E. Tasciotti, X. Liu, R. Bhavane, K. Plant, A. D. Leonard, B. K. Price, M. M. Cheng, P. Decuzzi, J. M. Tour, F. Robertson, M. Ferrari, Mesoporous silicon particles as a multistage delivery system for imaging and therapeutic applications. Nat Nanotechnol. 3, 151, (2008)

The invention claimed is:

1. A method for producing a bioengineered lung (BEL) comprising:
   (a) obtaining an acellular (AC) lung scaffold from lungs perfused with a dextrose solution prior to decellularization;
   (b) treating the AC lung scaffold with one or more growth factors, wherein the growth factors are delivered by porous nanoparticles or porous microparticles;
   (c) seeding the treated AC lung scaffold with primary lung cells; and
   (d) culturing the seeded AC lung scaffold in a bioreactor to produce a functional BEL.

2. The method of claim 1, wherein step (d) comprises adding immune cells to the BEL during culturing to reconstitute the immune system of the BEL.

3. The method of claim 1, wherein step (c) comprises seeding the treated AC lung scaffold with vascular cells isolated from peripheral blood.

4. The method of claim 1, wherein the primary lung cells are derived from a large mammal.

5. The method of claim 1, wherein the primary lung cells are derived from a pig, sheep, goat or other ungulate or bovine, or are derived from a human or non-human primate.

6. The method of claim 1, wherein the primary lung cells are of porcine origin.

7. The method of claim 1, wherein said primary lung cells are obtained from a biopsy or pneumonectomy of lung which biopsy or pneumonectomy optionally is pretreated with dextrose prior to decellularization wherein decellularization optionally is effected using sodium dodecyl sulfate (SDS).

8. The method of claim 1, wherein step (b) comprises treating the AC lung scaffold with VEGF, FGF2, KGR, or any combination thereof.

9. The method of claim 1, wherein step (b) comprises treating the AC lung scaffold with VEGF and FGF2.

10. The method of claim 1, wherein step (b) comprises treating the AC lung scaffold with microparticles or nanoparticles comprising VEGF and a hydrogel comprising FGF2.

11. The method of claim 1, wherein step (b) comprises treating the AC lung scaffold with microparticles or nanoparticles comprising VEGF and a hydrogel comprising FGF2, a hydrogel comprising KGR, and a hydrogel comprising platelet rich plasma.

12. The method of claim 1, wherein the microparticles or nanoparticles used to deliver one or more growth factors comprise non-spherical microparticles or nanoparticles comprising pores optionally of different sizes, further optionally 30 or 60 nm size pores.

13. The method of claim 1, wherein the primary lung cells comprise primary vascular cells.

14. The method of claim 1, wherein the immune system of the BEL is reconstituted by the addition of mononuclear leukocytes (MNLs), optionally autologous, to the bioreactor culture optionally at about day 11 of culture.

15. The method of claim 2, wherein the immune cells comprise one or more of mesenchymal stem cells, macrophages, or mononuclear leucocytes.

16. The method of claim 2, wherein the immune cells are introduced at day 5 or later of bioreactor culture.

17. The method of claim 1, wherein step (d) further comprises adding a culture supernatant from mesenchymal stem cells, macrophages, or mononuclear leucocytes.

18. The method of claim 1, wherein step (b) comprises adding immune cells to the AC lung scaffold.

19. The method of claim 18, wherein the immune cells comprise one or more of mesenchymal stem cells, macrophages, or mononuclear leucocytes.

20. The method of claim 1, wherein step (b) further comprises adding a culture supernatant from mesenchymal stem cells, macrophages, or mononuclear leucocytes.

* * * * *